US009937252B2

(12) United States Patent
McLean et al.

(10) Patent No.: US 9,937,252 B2
(45) Date of Patent: Apr. 10, 2018

(54) INDUCTION OF CROSS-REACTIVE CELLULAR RESPONSE AGAINST RHINOVIRUS ANTIGENS

(71) Applicants: SANOFI PASTEUR, Lyons (FR); IMPERIAL INNOVATIONS LIMITED, London (GB)

(72) Inventors: Gary McLean, London (GB); Walton Ross, Stratford upon Avon Warwickshire (GB); Sebastian Johnston, London (GB); Nathan Wylie Bartlett, Newcastle (GB); Bruno Guy, Lyons (FR); Yves Girerd-Chambaz, Messimy (FR); Valerie Lecouturier, Chazay d'Azergues (FR); Jeffrey Almond, Reading (GB); Nicholas Glanville, London (GB); Nicolas Burdin, Saint Genis les Ollieres (FR)

( * ) Notice: Subject to any disclaimer, the term of this patent is extended or adjusted under 35 U.S.C. 154(b) by 0 days.

(21) Appl. No.: 14/766,268

(22) PCT Filed: Feb. 6, 2014

(86) PCT No.: PCT/EP2014/052349
§ 371 (c)(1),
(2) Date: Aug. 6, 2015

(87) PCT Pub. No.: WO2014/122220
PCT Pub. Date: Aug. 14, 2014

(65) Prior Publication Data

US 2016/0095916 A1 Apr. 7, 2016

(30) Foreign Application Priority Data

Feb. 7, 2013 (EP) .................................... 13305152

(51) Int. Cl.

| | |
|---|---|
| ***A61K 39/125*** | (2006.01) |
| ***C07K 14/005*** | (2006.01) |
| ***C12N 9/12*** | (2006.01) |
| ***A61K 39/12*** | (2006.01) |
| *A61K 39/00* | (2006.01) |

(52) U.S. Cl.
CPC ............ *A61K 39/125* (2013.01); *A61K 39/12* (2013.01); *C07K 14/005* (2013.01); *C12N 9/127* (2013.01); *A61K 2039/53* (2013.01); *A61K 2039/55561* (2013.01); *A61K 2039/55566* (2013.01); *A61K 2039/57* (2013.01); *C07K 2319/00* (2013.01); *C12N 2770/32722* (2013.01); *C12N 2770/32734* (2013.01)

(58) Field of Classification Search
None
See application file for complete search history.

(56) References Cited

U.S. PATENT DOCUMENTS

| | | | | |
|---|---|---|---|---|
| 2005/0255121 A1* | 11/2005 | Campbell | ............ | A61K 9/0021 424/184.1 |
| 2010/0233677 A1* | 9/2010 | Liggett | .................... | C12Q 1/70 435/5 |

FOREIGN PATENT DOCUMENTS

| | | |
|---|---|---|
| WO | 2006/078648 | 7/2006 |
| WO | 2011/050384 | 5/2011 |

OTHER PUBLICATIONS

Palmenberg et al. (Science. 2009; 324 (3): 55-59).*
Sequence alignment of instant SEQ ID No. 5 AYJ77291 of Liggett et al in USPgPub 2010233677 Sep. 2010.*
Megremis et al. (PLoS One. Sep. 2012. 7(9): e44557. doi:10.1371/journal.pone.0044557).*
Poch et al. (The EMBO Journal. 1989; 8 (12): 3867-3874).*
Crowder et al. (Structure. 2004; 12 (8): 1336-339).*
The sequence alignment of instant SEQ ID Nos. 1 with Geneseq database accession No. AYJ77291 of Liggett et al in USPgPub 2010233677 Sep. 2010.*
The sequence alignment of instant SEQ ID Nos. 3 with Geneseq database accession No. AYJ77291 of Liggett et al in USPgPub 2010233677 Sep. 2010.*
The sequence alignment of instant SEQ ID Nos. 6 with Geneseq database accession No. AYJ77291 of Liggett et al in USPgPub 2010233677 Sep. 2010.*
The sequence alignment of instant SEQ ID Nos. 13 with Geneseq database accession No. AYJ77291 of Liggett et al in USPgPub 2010233677 Sep. 2010.*
Hastings et al. (European Journal of Immunology. 1993; 23: 2300-2305).*
Katpally et al. "Antibodies to the Buried N Terminus of Rhinovirus VP4 Exhibit Cross-Serotypic Neutralization", Journal of Virology, vol. 83, No. 14, pp. 7040-7048, 2009.
Glanville et al. "Cross-Serotype Immunity Induced by Immunization with a Conserved Rhinovirus Capsid Protein", Plos Pathogens, vol. 9, No. 9, p. e1003669, 2013.
Love et al. "The Crystal Structure of the RNA-Dependent RNA Polymerase from Human Rhinovirus", Structure, vol. 12, No. 8, pp. 1533-1544, 2004.

(Continued)

*Primary Examiner* — Shanon A. Foley
(74) *Attorney, Agent, or Firm* — Gates & Cooper LLP

(57) ABSTRACT

The present invention concerns: a) an isolated peptide comprising an amino acid sequence which is at least 90% identical to the VP4 amino acid sequence of a rhinovirus, or an isolated polynucleotide comprising a nucleic acid sequence encoding said peptide, placed under the control of the elements necessary for its expression in a mammalian cell; and/or b) an isolated peptide comprising an amino acid sequence of at least 100 amino acids which is at least 90% identical to an amino acid sequence located in the last 363 C-terminal amino acids of the RNA polymerase of a rhinovirus, or an isolated polynucleotide comprising a nucleic acid sequence encoding said peptide, placed under the control of the elements necessary for its expression in a mammalian cell; and c) a Th1 adjuvant when said immunogenic composition comprises one or more of said isolated peptides.

15 Claims, 29 Drawing Sheets

(56) References Cited

OTHER PUBLICATIONS

Palmenberg et al. "Sequencing and Analyses of All Known Human Rhinovirus Genomes Reveal Structure and Evolution", Science, vol. 324, No. 5923, pp. 55-59, 2009.

Shibaki et al. "Induction of skewed Th1/Th2 T-cell differentiation via subcutaneous immunization with Freund's adjuvant", Experimental Dermatology, vol. 11, No. 2, pp. 126-134, 2002.

PCT International Search Report and Written Opinion from PCT/EP2014/052349 dated Jul. 2, 2014.

European Search Report from EP Patent Application No. 13305152.4 dated Jun. 24, 2013.

* cited by examiner

INDUCTION OF CROSS-REACTIVE CELLULAR RESPONSE AGAINST RHINOVIRUS ANTIGENS

SEQUENCE LISTING

The instant application contains a Sequence Listing which has been submitted electronically in ASCII format and is hereby incorporated by reference in its entirety. Said ASCII copy, created on Dec. 8, 2015, is named 272.2-US-WO_SL.txt and is 61,515 bytes in size.

The present invention concerns immunogenic compositions enabling inducing a cross-reactive immune response in a subject against rhinovirus antigens.

Human rhinovirus (HRV) infections are the most frequent cause of the common cold and are highly associated with exacerbations of asthma and chronic obstructive pulmonary disease (COPD) in individuals at risk. Despite the great disease burden and healthcare costs therefore attributable to HRV infections, there is currently neither a vaccine nor specific anti-viral therapy available.

The requirements for immunity to HRV are poorly understood. Both experimental and natural infections do induce antibodies which provide some protection against re-infection with the same HRV type. There are however greater than 100 serotypes of HRV, a number which is likely to increase further with the identification and characterization of new serotypes. Currently the main efforts to develop a candidate vaccine against HRV are focusing on the identification of antigens that induce a broad neutralizing antibody response. This approach is described in the international application WO 2011/050384, whereby it is shown that antibodies raised against a recombinant rhinovirus capsid protein, VP1, show cross-protection against distantly related HRV strains. Another study (Katpally et al. (2009) *J. Virol.* 83:7040-7048) shows that antibodies directed to the buried N-terminus of the rhinovirus capsid protein, VP4, exhibit cross-serotypic neutralization. However, there is no certainty that a vaccine strategy based only on generating neutralizing antibodies could provide a sufficient and broad protection to prevent the frequent HRV infections which occur throughout life.

There is therefore an important need to develop alternative vaccine strategies that could be more successful.

Vaccination strategies based on inducing T cell responses to conserved antigens have been explored in a number of infectious diseases, including respiratory virus infections. The advantage of such a strategy lies in the ability of T cells to recognize internal regions of the virus, which are frequently more conserved than surface exposed antibody epitopes. T cells are therefore potentially cross-reactive against different virus strains, as has been shown with influenza viruses (Lee et al. (2008) *J. Clin. Invest.* 118:3478-3490; Richards et al. (2010) *J. Immunol.* 185:4998-5002) for which surface antigenic variability is a major barrier to effective vaccine design.

For HRVs, naturally occurring memory T cells have been shown to be cross-serotype responsive (Gern et al. (1997) *J. Infect. Dis.* 175:1108-1114; Wimalasundera et al. (1997) *J. Infect. Dis.* 176:755-759) and immunization of mice with peptides from VP1 and VP3 capsid proteins of HRV has been suggested to be capable of inducing cross-serotype reactive T cells (Hastings et al. (1993) *Eur. J. Immunol.* 23:2300-2305). However, it has not been shown that a T cell mediated immune response against HRV is protective against rhinovirus infection.

The inventors have now featured new immunogenic compositions that are able to induce a broad cross-reactive cellular immune response among rhinoviruses, and which have been shown to also accelerate rhinovirus clearance in rhinovirus infected subjects.

Based on linear sequence conservation among HRVs, the inventors identified antigens which were able to induce antigen-specific, cross-reactive, type I-orientated T cell responses and enhanced neutralizing antibody responses following infection in mice. Said antigens correspond to conserved domains in the HRV P1 polyprotein and the HRV RNA polymerase.

Specifically, the inventors identified as a particularly useful antigen:

- an isolated peptide comprising, or consisting of, an amino acid sequence which is at least 90% identical to the VP4 amino acid sequence of a rhinovirus;
- a fusion peptide comprising an amino acid sequence which is at least 90% identical to the VP4 amino acid sequence of a rhinovirus, covalently linked to another conserved amino acid sequence of the "large" polyprotein of the rhinovirus, including in particular all or part of the VP2 amino acid sequence and/or conserved domains of the RNA polymerase; or
- an isolated peptide comprising, or consisting of, an amino acid sequence of at least 100 amino acids which is at least 90% identical to an amino acid sequence located in the last 363 C-terminal amino acids of the RNA polymerase of a rhinovirus.

In particular, administering to mice a peptide comprising the HRV16 VP4 peptide, more particularly a peptide consisting of the HRV16 VP0 polyprotein, or a peptide, the amino acid sequence of which is located within the last 363 C-terminal amino acids of the HRV16 RNA polymerase, enabled inducing a cross-reactive immune response against HRV16, but also against other HRV serotypes, such as HRV14, HRV1B or HRV29.

The present invention therefore concerns an immunogenic composition comprising:

a) an isolated peptide or a fusion peptide as described above comprising an amino acid sequence which is at least 90% identical to the VP4 amino acid sequence of a rhinovirus, or an isolated polynucleotide comprising a nucleic acid sequence encoding said peptide, placed under the control of the elements necessary for its expression in a mammalian cell; and/or b) an isolated peptide comprising an amino acid sequence of at least 100 amino acids which is at least 90% identical to an amino acid sequence located in the last 363 C-terminal amino acids of the RNA polymerase of a rhinovirus, or an isolated polynucleotide comprising a nucleic acid sequence encoding said peptide, placed under the control of the elements necessary for its expression in a mammalian cell; and c) a Th1 adjuvant when said immunogenic composition comprises one or more of said isolated peptides or fusion peptides.

The present invention also concerns an immunogenic composition as defined above for use in a mammal to induce a specific cross-reactive cell-mediated immune response against at least two serotypes of rhinoviruses.

The present invention is further drawn to an immunogenic composition as defined above for use in a mammal to induce a specific neutralizing antibody response when infected by a rhinovirus.

The present invention also concerns an immunogenic composition as defined above for use in a mammal to shorten or prevent an infection by a rhinovirus, and/or to reduce or prevent the clinical symptoms associated with the infection. Therefore, the immunogenic composition as defined above can be used as a vaccine to protect against rhinovirus infection.

DETAILED DESCRIPTION OF THE INVENTION

Rhinoviruses

In the context of the invention, the term “rhinovirus” or “HRV” (Human rhinovirus) refers to any member of the family Picornaviridae genus Enterovirus according to the recent taxonomy. There are 3 different groups of rhinoviruses: Human rhinovirus A (HRV-A) also called type A rhinovirus, Human rhinovirus B (HRV-B) also called type B rhinovirus and Human rhinovirus C (HRV-C) also called type C rhinovirus.

HRVs are further classified according to their serotype, of which more than 100 have been reported until now.

As used herein, the term “serotype” refers to a subdivision within a group of rhinoviruses and relies on the VP1 gene sequence of the rhinovirus. A given serotype of rhinovirus may contain one or several strains that are distinguished by secondary characteristics. HRVs have been classified according to several other parameters, including receptor specificity, antiviral susceptibility and nucleotide sequence homologies. The HRV-A species includes in particular the following serotypes: HRV1A, HRV1B, HRV2, HRV7, HRV8, HRV9, HRV10, HRV11, HRV12, HRV13, HRV15, HRV16, HRV18, HRV19, HRV20, HRV21, HRV22, HRV23, HRV24, HRV25, HRV28, HRV29, HRV30, HRV31, HRV32, HRV33, HRV34, HRV36, HRV38, HRV39, HRV40, HRV41, HRV43, HRV44, HRV45, HRV46, HRV47, HRV49, HRV50, HRV51, HRV53, HRV54, HRV55, HRV56, HRV57, HRV58, HRV59, HRV60, HRV61, HRV62, HRV63, HRV64, HRV65, HRV66, HRV67, HRV68, HRV71, HRV73, HRV74, HRV75, HRV76, HRV77, HRV78, HRV80, HRV81, HRV82, HRV85, HRV88, HRV89, HRV90, HRV94, HRV95, HRV96, HRV98, HRV100, HRV101, HRV102 and HRV103; the HRV-B species includes in particular the following serotypes: HRV3, HRV4, HRV5, HRV6, HRV14, HRV17, HRV26, HRV27, HRV35, HRV37, HRV42, HRV48, HRV52, HRV69, HRV70, HRV72, HRV79, HRV83, HRV84, HRV86, HRV91, HRV92, HRV93, HRV97 and HRV99; and the HRV-C species includes in particular the following serotypes: HRVC-1, HRVC-2, HRVC-3, HRVC-4, HRVC-5, HRVC-6, HRVC-7, HRVC-8, HRVC-9, HRVC-10, HRVC-11, HRVC-12, HRVC-13, HRVC-14, HRVC-15, HRVC-16, HRVC-17, HRVC-18, HRVC-19, HRVC-20, HRVC-21, HRVC-22, HRVC-23, HRVC-24, HRVC-25, HRVC-26, HRVC-27, HRVC-28, HRVC-29, HRVC-30, HRVC-31, HRVC-32, HRVC-33, HRVC-34, HRVC-35, HRVC-36, HRVC-37, HRVC-38, HRVC-39, HRVC-40, HRVC-41, HRVC-42, HRVC-43, HRVC-44, HRVC-45, HRVC-46, HRVC-47, HRVC-48 and HRVC-49.

HRV serotypes may also be grouped according to receptor usage into minor-group viruses and major-group viruses.

Minor-group viruses, such as HRV2, use the low-density lipoprotein receptor family as receptor. They are acid labile and have an absolute dependence on low pH for uncoating. Major-group viruses, such as HRV14 and HRV16, use intercellular adhesion molecule 1 (ICAM-1) as receptor.

They are also generally acid labile but, unlike the minor-group viruses, do not have an absolute dependence on low pH for uncoating.

As well-known from the skilled person, minor-group HRVs include 11 serotypes, including HRV1A, HRV1B, HRV2, HRV23, HRV25, HRV29, HRV30, HRV31, HRV44, HRV47, HRV49 and HRV62, and major-group HRVs include the remaining serotypes.

HRVs have a 25 nm capsid of icosahedral symmetry, made up of 60 copies of each of four virus-coded proteins (VP1, VP2, VP3 and VP4) and enclosing a single-stranded RNA genome of approximately 7,500 nucleotides. The RNA is of positive polarity, is polyadenylated at its 3' terminus and is covalently bound at its 5' terminal end to a small protein, VPg. The primary translational product of this RNA is a single, “large” polyprotein, divided into three smaller polyproteins called, P1, P2 and P3, which are subsequently processed by proteolytic cleavage to yield the mature virus proteins. The P1 polyprotein is composed of four peptides (1A or VP4, 1B or VP2, 1C or VP3, and 1D or VP1), the P2 polyprotein is composed of three peptides (2A, 2B and 2C) and the P3 polyprotein is composed of four peptides (3A, 3B, 3C and 3D, which corresponds to the RNA polymerase). The P1 polyprotein is the precursor that gives rise to the four structural proteins of the nucleocapsid. The P1 polyprotein is first cleaved to produce the VP0 polyprotein, which contains the amino acid sequence of VP4 and VP2 peptides, the VP3 peptide and the VP1 peptide. The VP0 polyprotein is then cleaved into the VP4 peptide and the VP2 peptide once the virus has assembled.

In the context of the invention, the term “VP0 polyprotein”, “VP0 peptide” or “peptide 1AB” therefore refers to the protein precursor derived from the HRV P1 polyprotein and which consists of the amino acid sequence of VP4 and VP2 peptides. VP0 polyprotein is typically about 330 amino acids long. As known from the skilled person, the amino acid sequence of the VP0 polyprotein may slightly vary according to the HRV serotype or group.

In the context of the invention the term “about” as used herein when referring to a measurable value, such as an amount, duration or a number, such as the number of amino acids in an amino acid sequence, is meant to encompass variations of ±5%.

In the context of the invention the term “a” or “an” entity refers to one or more of that entity. For example “a polynucleotide”, “an isolated peptide”, “a fusion peptide”, “an isolated polynucleotide” is understood to represent respectively at least one or more “polynucleotide”, at least one or more “isolated peptide”, at least one or more “fusion peptide”, at least one or more “isolated polynucleotide”.

In the context of the invention, the terms “comprising”, “having”, “including” and “containing” are to be construed as open-ended terms (i.e., meaning “including, but not limited to,”) unless otherwise noted. Additionally, the term “comprising” encompasses “consisting” (e.g., a composition “comprising” X may consist exclusively of X or may include something additional, e.g., X+Y).

In an embodiment, the amino acid sequence of the VP0 polyprotein is the amino acid sequence of the VP0 polyprotein of the HRV16 serotype, which consists typically in the sequence:

(SEQ ID NO: 6)
MGAQVSRQNVGTHSTQNMVSNGSSLNYFNINYFKDAASSGASRLDFSQDP

SKFTDPVKDVLEKGIPTLQSPSVEACGYSDRIIQITRGDSTITSQDVANA

VVGYGVWPHYLTPQDATAIDKPTQPDTSSNRFYTLDSKMWNSTSKGWWWK

LPDALKDMGIFGENMFYHFLGRSGYTVHVQCNASKFHQGTLLVVMIPEHQ

LATVNKGNVNAGYKYTHPGEAGREVGTQVENEKQPSDDNWLNFDGTLLGN

LLIFPHQFINLRSNNSATLIVPYVNAVPMDSMVRHNNWSLVIIPVCQLQS

NNISNIVPITVSISPMCAEFSGARAKTVV.

In another embodiment, the amino acid sequence of the VP0 polyprotein is the amino acid sequence of the VP0 polyprotein of the HRV14 serotype, which consists typically in the sequence:

(SEQ ID NO: 8)
MGAQVSTQKSGSHENQNILTNGSNQTFTVINYYKDAASTSSAGQSLSMDP

SKFTEPVKDLMLKGAPALNSPNVEACGYSDRVQQITLGNSTITTQEAANA

VVCYAEWPEYLPDVDASDVNKTSKPDTSVCRFYTLDSKTWTTGSKGWCWK

LPDALKDMGVFGQNMFFHSLGRSGYTVHVQCNATKFHSGCLLVVVIPEHQ

LASHEGGNVSVKYTFTHPGERGIDLSSANEVGGPVKDVIYNMNGTLLGNL

LIFPHQFINLRTNNTATIVIPYINSVPIDSMTRHNNVSLMVIPIAPLTVP

TGATPSLPITVTIAPMCTEFSGIRSKSIV.

The corresponding VP0 polyprotein amino acid sequence from other HRV serotypes may easily be determined by the skilled person, typically by sequence alignment, such as global pairwise alignment.

In the context of the invention, the term "VP4 peptide" or "peptide 1A" refers to an HRV protein capsid, derived from the VP0 polyprotein precursor, which lies at the interface between the capsid and the interior genomic RNA. VP4 peptide is about 68 or 69 amino acids long and is generally situated from amino acid 1 to amino acid 69 of the VP0 polyprotein. As known from the skilled person, the length of the amino acid sequence of the VP4 peptide may slightly vary according to the HRV serotype.

According to an embodiment, the amino acid sequence of the VP4 peptide is the amino acid sequence of the VP4 peptide of the HRV16 serotype, which consists typically in the sequence:

(SEQ ID NO: 1)
MGAQVSRQNVGTHSTQNMVSNGSSLNYFNINYFKDAASSGASRLDFSQDP

SKFTDPVKDVLEKGIPTLQ.

According to another embodiment, the amino acid sequence of the VP4 peptide is the amino acid sequence of the VP4 peptide of the HRV14 serotype, which consists typically in the sequence:

(SEQ ID NO: 2)
MGAQVSTQKSGSHENQNILTNGSNQTFTVINYYKDAASTSSAGQSLSMDP

SKFTEPVKDLMLKGAPALN.

The corresponding VP4 peptide sequence from other HRV serotypes may easily be determined by the skilled person, typically by sequence alignment, such as global pairwise alignment.

In the context of the invention, the term "VP2 peptide" or "peptide 1B" refers to an HRV protein capsid, derived from the VP0 polyprotein precursor, which lies at the external side of the capsid. VP2 peptide is about 270 amino acids long. Generally, the VP2 peptide is situated between amino acids 70 and 339 of the VP0 polyprotein. As known from the skilled person, the length of the amino acid sequence of the VP2 peptide may slightly vary according to the HRV serotype.

According to an embodiment, the amino acid sequence of the VP2 peptide is the amino acid sequence of the VP2 peptide of the HRV16 serotype, which consists typically in the sequence:

(SEQ ID NO: 3)
SPSVEACGYSDRIIQITRGDSTITSQDVANAVVGYGVWPHYLTPQDATAI

DKPTQPDTSSNRFYTLDSKMWNSTSKGWWWKLPDALKDMGIFGENMFYHF

LGRSGYTVHVQCNASKFHQGTLLVVMIPEHQLATVNKGNVNAGYKYTHPG

EAGREVGTQVENEKQPSDDNWLNFDGTLLGNLLIFPHQFINLRSNNSATL

IVPYVNAVPMDSMVRHNNWSLVIIPVCQLQSNNISNIVPITVSISPMCAE

FSGARAKTVV.

According to another embodiment, the amino acid sequence of the VP2 peptide is the amino acid sequence of VP2 peptide of the HRV14 serotype, which consists typically in the sequence:

(SEQ ID NO: 4)
SPNVEACGYSDRVQQITLGNSTITTQEAANAVVCYAEWPEYLPDVDASDV

NKTSKPDTSVCRFYTLDSKTWTTGSKGWCWKLPDALKDMGVFGQNMFFHS

LGRSGYTVHVQCNATKFHSGCLLVVVIPEHQLASHEGGNVSVKYTFTHPG

ERGIDLSSANEVGGPVKDVIYNMNGTLLGNLLIFPHQFINLRTNNTATIV

IPYINSVPIDSMTRHNNVSLMVIPIAPLTVPTGATPSLPITVTIAPMCTE

FSGIRSKSIV.

The corresponding VP2 peptide sequence from other HRV serotypes may easily be determined by the skilled person, typically by sequence alignment, such as global pairwise alignment.

In the context of the invention, the term "RNA polymerase" or "peptide 3D" refers to the HRV RNA-dependent RNA polymerase, located at the carboxy-terminal end of the precursor "large" polyprotein, within the P3 protein, and which is the core enzyme utilized for both negative-strand RNA synthesis and reiterative synthesis of multiple copies of positive strand RNA for packaging into progeny virions. HRV RNA polymerase is typically described in Appleby et al. (2005) *J. Virol.* 79:277-288. HRV RNA polymerase is typically about 460 amino acids long. As known from the skilled person, the length of the amino acid sequence of the RNA polymerase may slightly vary according to the HRV serotype.

According to an embodiment, the amino acid sequence of the RNA polymerase is the amino acid sequence of the RNA polymerase of the HRV16 serotype, which consists typically in the sequence:

(SEQ ID NO: 15)
GQIQISKHVKDVGLPSIHTPTKTKLQPSVFYDIFPGSKEPAVLTEKDPRL
KVDFDSALFSKYKGNTECSLNEHIQVAVAHYSAQLATLDIDPQPIAMEDS
VFGMDGLEALDLNTSAGYPYVTLGIKKKDLINNKTKDISKLKLALDKYDV
DLPMITFLKDELRKKDKIAAGKTRVIEASSINDTILFRTVYGNLFSKFHL
NPGVVTGCAVGCDPETFWSKIPLMLDGDCIMAFDYTNYDGSIHPIWFKAL
GMVLDNLSFNPTLINRLCNSKHIFKSTYYEVEGGVPSGCSGTSIFNSMIN
NIIIRTLVLDAYKHIDLDKLKIIAYGDDVIFSYKYKLDMEAIAKEGQKYG
LTITPADKSSEFKELDYGNVTFLKRGFRQDDKYKFLIHPTFPVEEIYESI
RWTKKPSQMQEHVLSLCHLMWHNGPEIYKDFETKIRSVSAGRALYIPPYE
LLRHEWYEKF.

According to another embodiment, the amino acid sequence of the RNA polymerase is the amino acid sequence of the RNA polymerase of the HRV14 serotype, which consists typically in the sequence:

(SEQ ID NO: 16)
GQVIARHKVREFNINPVNTPTKSKLHPSVFYDVFPGDKEPAVLSDNDPRL
EVKLTESLFSKYKGNVNTEPTENMLVAVDHYAGQLLSLDIPTSELTLKEA
LYGVDGLEPIDITTSAGFPYVSLGIKKRDILNKETQDTEKMKFYLDKYGI
DLPLVTYIKDELRSVDKVRLGKSRLIEASSLNDSVNMRMKLGNLYKAFHQ
NPGVLTGSAVGCDPDVFWSVIPCLMDGHLMAFDYSNFDASLSPVWFVCLE
KVLTKLGFAGSSLIQSICNTHHIFRDEIYVVEGGMPSGCSGTSIFNSMIN
NIIIRTLILDAYKGIDLDKLKILAYGDDLIVSYPYELDPQVLATLGKNYG
LTITPPDKSETFTKMTWENLTFLKRYFKPDQQFPFLVHPVMPMKDIHESI
RWTKDPKNTQDHVRSLCMLAWHSGEKEYNEFIQKIRTTDIGKCLILPEYS
VLRRRWLDLF.

The corresponding RNA polymerase sequence from other HRV serotypes may easily be determined by the skilled person, typically by sequence alignment, such as global pairwise alignment.

In the context of the invention, the term "C-terminal domain of the RNA polymerase of a rhinovirus" refers to the C-terminal end of the HRV RNA polymerase as defined above, in particular to the last 363 C-terminal amino acids of the HRV RNA polymerase as defined above. As known from the skilled person, the length of the amino acid sequence of the C-terminal domain of the HRV RNA polymerase may slightly vary according to the HRV serotype.

According to an embodiment, the amino acid sequence of the C-terminal domain of the RNA polymerase is the amino acid sequence of the C-terminal domain of the RNA polymerase of the HRV16 serotype, which consists typically in the sequence:

(SEQ ID NO: 13)
EDSVFGMDGLEALDLNTSAGYPYVTLGIKKKDLINNKTKDISKLKLALDK
YDVDLPMITFLKDELRKKDKIAAGKTRVIEASSINDTILFRTVYGNLFSK
FHLNPGVVTGCAVGCDPETFWSKIPLMLDGDCIMAFDYTNYDGSIHPIWF

-continued
KALGMVLDNLSFNPTLINRLCNSKHIFKSTYYEVEGGVPSGCSGTSIFNS
MINNIIIRTLVLDAYKHIDLDKLKIIAYGDDVIFSYKYKLDMEAIAKEGQ
KYGLTITPADKSSEFKELDYGNVTFLKRGFRQDDKYKFLIHPTFPVEEIY
ESIRWTKKPSQMQEHVLSLCHLMWHNGPEIYKDFETKIRSVSAGRALYIP
PYELLRHEWYEKF.

According to another embodiment, the amino acid sequence of the C-terminal domain of the RNA polymerase is the amino acid sequence of the C-terminal domain of the RNA polymerase of the HRV14 serotype, which consists typically in the sequence:

(SEQ ID NO: 14)
KEALYGVDGLEPIDITTSAGFPYVSLGIKKRDILNKETQDTEKMKFYLDK
YGIDLPLVTYIKDELRSVDKVRLGKSRLIEASSLNDSVNMRMKLGNLYKA
FHQNPGVLTGSAVGCDPDVFWSVIPCLMDGHLMAFDYSNFDASLSPVWFV
CLEKVLTKLGFAGSSLIQSICNTHHIFRDEIYVVEGGMPSGCSGTSIFNS
MINNIIIRTLILDAYKGIDLDKLKILAYGDDLIVSYPYELDPQVLATLGK
NYGLTITPPDKSETFTKMTWENLTFLKRYFKPDQQFPFLVHPVMPMKDIH
ESIRWTKDPKNTQDHVRSLCMLAWHSGEKEYNEFIQKIRTTDIGKCLILP
EYSVLRRRWLDLF.

The corresponding RNA polymerase C-terminal domain sequence from other HRV serotypes may easily be determined by the skilled person, typically by sequence alignment, such as global pairwise alignment.

Peptides

Based on linear sequence conservation among HRVs, the present inventors identified antigens which were able to induce a cross-reactive immune response against different serotypes of rhinoviruses and even more unexpectedly against rhinoviruses belonging to different groups of rhinoviruses (cross-serotype and/or inter-group reactive immune response). Said antigens correspond to conserved domains in the HRV VP0 polyprotein and the HRV RNA polymerase, as defined in the section "Rhinoviruses" herein above. In particular, the inventors demonstrated that administering to mice a peptide comprising the HRV16 VP4 peptide, more particularly a peptide consisting of the HRV16 VP0 polyprotein, enabled inducing a cross-reactive immune response against HRV16, but also against other HRV serotypes, such as HRV14, HRV1B or HRV29.

Specifically, the inventors identified as a particularly useful antigen:

- an isolated peptide a) comprising, or consisting of, an amino acid sequence which is at least 90% identical to the VP4 amino acid sequence of a rhinovirus, as defined in the section "Rhinoviruses" herein above, or
- a fusion peptide comprising an amino acid sequence which is at least 90% identical to the VP4 amino acid sequence of a rhinovirus, as defined in the section "Rhinoviruses" herein above, covalently linked to another conserved amino acid sequence located in the "large" polyprotein, as defined in the section "Rhinoviruses" herein above, of a rhinovirus.

The inventors also identified as another particularly useful antigen, an isolated peptide b) comprising, or consisting of, an amino acid sequence of at least 100 amino acids which is at least 90% identical to an amino acid sequence located in the last 363 C-terminal amino acids of the RNA polymerase of a rhinovirus, as defined in the section "Rhinoviruses" herein above.

By "an amino acid sequence located in the last 363 C-terminal amino acids of the RNA polymerase" is meant an amino acid sequence which consists of a chain of contiguous amino acids found in the region defined by the last 363 C-terminal amino acids of the RNA polymerase, i.e a fragment of said region.

As used herein, the term "isolated" means removed from the natural environment, i.e. from rhinoviruses or cells infected by a rhinovirus. Usually, it refers to a peptide, a fusion peptide or a nucleic acid substantially free of cellular material, bacterial material, viral material, or culture medium when produced by recombinant DNA techniques, or chemical precursors, or other chemicals when chemically synthesized.

The term "substantially" encompasses "completely" or "nearly" (e.g., a composition which is "substantially free" from Y may be completely free from Y or may contain residual amount of Y).

According to the invention, a polypeptide, peptide or fusion peptide consists of at least about 60 amino acids, in particular at least about 68 amino acids, at least 69 amino acids, at least 120 amino acids, at least 140 amino acids, at least 160 amino acids, at least 180 amino acids, at least 200 amino acids, at least 220 amino acids, at least 240 amino acids, at least 260 amino acids, at least 280 amino acids, at least 300 amino acids, at least 320 amino acids, at least 340 amino acids, or even at least 370 amino acids.

According to the invention, a polypeptide, peptide or fusion peptide consists of less than 500 amino acids, in particular of less than 450, less than 400, or even less than 380 amino acids.

Accordingly, the size of a polypeptide, peptide or fusion peptide is typically between 60 and 500 amino acids long, in particular between 68 and 500 amino acids long, more particularly between 100 and 500 amino acids long, still particularly between 100 and 400 amino acids long, the bounds being included.

As used herein, the term "amino acid" is understood to include the 20 naturally occurring amino acids.

As used herein, a first amino acid sequence is at least x % identical to a second amino acid sequence means that x % represents the number of amino acids in the first sequence which are identical to their matched amino acids of the second sequence when both sequences are optimally aligned, relative to the total length of the second amino acid sequence. Both sequences are optimally aligned when x is maximum. The alignment and the determination of the percentage of identity may be carried out manually or automatically using for instance the Needleman and Wunsch algorithm, described in Needleman and Wunsch (1970) *J. Mol Biol.* 48:443-453, with for example the following parameters for polypeptide sequence comparison:

comparison matrix: BLOSSUM62 from Henikoff and Henikoff (1992) *Proc. Natl. Acad. Sci. USA.* 89:10915-10919, gap penalty: 8 and gap length penalty: 2;

and the following parameters for polynucleotide sequence comparison:

comparison matrix: matches=+10, mismatch=0; gap penalty: 50 and gap length penalty: 3.

A program useful with the above parameters is publicly available as the "gap" program from Genetics Computer Group, Madison Wis. The aforementioned parameters are the default parameters respectively for peptide comparisons (along with no penalty for end gaps) and for nucleic acid comparisons.

In particular, the isolated peptide a) of the immunogenic composition according to the invention comprises, or consists of, an amino acid sequence which is at least 90% identical, at least 95% identical, at least 97% identical, at least 98% identical, at least 99% identical or even 100% identical to the VP4 amino acid sequence of a rhinovirus, as defined in the section "Rhinoviruses" herein above. For instance any VP4 amino acid sequence of a rhinovirus strain which is at least 90% identical to the VP4 peptide of the HRV16 serotype (SEQ ID NO: 1) or of the HRV14 serotype (SEQ ID NO: 2) is suitable for the purpose of the invention.

The isolated peptide b) of the immunogenic composition according to the invention comprises, or consists of, an amino acid sequence of at least 100 amino acids, for instance at least 105, no, 120, 130, 140, 150, 160, 170, 180, 190, 200, 210, 220, 230, 240, 250, 260, 270, 280, 290, 300, 320, 330, 340 or 350 amino acids, in particular at least 360 amino acids which is at least 90% identical to an amino acid sequence located in the last 363 C-terminal amino acids of the RNA polymerase of a rhinovirus as defined in the section "Rhinoviruses" herein above. More particularly, the isolated peptide b) of the invention comprises, or consists of an amino acid sequence of at least 100 amino acids which is at least 95% identical, at least 97% identical, at least 98% identical, at least 99%, or even 100% identical to the RNA polymerase amino acid sequence of a rhinovirus, as defined in the section "Rhinoviruses" herein above. For instance any amino acid sequence of at least 100 amino acids located in the last 363 C-terminal amino acids of the RNA polymerase of a rhinovirus strain which is at least 90% identical to the corresponding amino acid sequence located in the last 363 C-terminal amino acids of the RNA polymerase of the HRV16 serotype (SEQ ID NO: 13) or of the HRV14 serotype (SEQ ID NO: 14) is suitable for the purpose of the invention.

In some particular instances, even if not preferred, a natural amino acid may be substituted by an amino acid modified post-translationally in vivo, including for example hydroxyproline, phosphoserine and phosphothreonine; by unusual amino acids including, but not limited to, 2-aminoadipic acid, hydroxylysine, isodesmosine, nor-valine, norleucine and ornithine or by another chemically modified amino acid.

Peptides and fusion peptides of the invention may be synthesized by any method well-known from the skilled person. Such methods include conventional chemical synthesis (in solid phase or in liquid homogenous phase), enzymatic synthesis from constitutive amino acids or derivatives thereof, as well as biological production methods by recombinant technology.

Chemical synthesis can be particularly advantageous because it allows high purity, antigenic specificity, the absence of undesired by-products and ease of production. The peptide obtained by such methods can then optionally be purified using any method known from the skilled person. The method of production can also include one or more steps of chemical or enzymatic modification of the peptide in order to improve its stability or its bioavailability.

Chemical synthesis includes Merrifield type synthesis and Fmoc solid phase peptide synthesis methods (see for example "Fmoc solid Phase peptide synthesis, a practical approach", published by W. C. Chan et P. D. White, Oxford University Press, 2000).

The peptide or fusion peptide of the invention can also be obtained using a biological production process with a recombinant host cell. In such a process, a vector containing a nucleic acid encoding the peptide or fusion peptide of the invention, in particular a nucleic acid as defined in the section "Nucleic acids" herein below, is transferred into a host cell, which is cultured in conditions enabling expression of the corresponding peptide or fusion peptide. The peptide or fusion peptide thereby produced can then be recovered and purified.

Methods of purification that can be used are well-known from the skilled person. The obtained recombinant peptide or fusion peptide can be purified from lysates and cell extracts, from the culture medium supernatant, by methods used individually or in combination, such as fractionation, chromatographic methods, immunoaffinity methods using specific mono- or polyclonal antibodies, etc. . . . .

Fusion Peptides

In the context of the invention, the term "fusion peptide" refers to a peptide composed of all or part of the amino acid sequence of at least two or more individual peptide units of a rhinovirus linked together via a covalent linkage, e.g. via peptide (amide) bonds.

More specifically, the fusion peptide included in the immunogenic composition according to the invention refers to the VP4 amino acid sequence of a rhinovirus, or an amino acid sequence that is at least 90% identical to the VP4 amino acid sequence of a rhinovirus, linked by a covalent linkage to another conserved amino sequence present in the "large" polyprotein of a rhinovirus.

Even if, among all the rhinovirus peptides (VP4, VP1, VP2, VP3, peptides 2A, 2B, 2C, 3A, 3B, 3C, 3D), the VP4 amino acid sequence is considered as being the most conserved amino acid sequence among the rhinoviruses, the inventors have found that when the VP4 amino acid sequence is covalently linked to an amino acid sequence located in the VP2 amino sequence of a rhinovirus and/or an amino acid sequence located in the last 363 C-terminal amino acids of the RNA polymerase, which are domains that the inventors have identified as being conserved among rhinoviruses, such fusion peptides associated with a Th1 adjuvant are able to induce a cross-reactive immune response against different serotypes of rhinoviruses. More unexpectedly, a cross-reactive immune cell response against rhinoviruses belonging to different species of rhinoviruses has been observed. Furthermore the inventors have shown that such fusion peptides can rapidly induce virus clearance in rhinovirus-infected mice.

In a preferred embodiment, the isolated peptide a) of the immunogenic composition according to the invention is a fusion peptide which comprises, or consists of, an amino acid sequence that is at least 90% identical to the VP4 amino acid sequence of a rhinovirus, as defined in the section "Rhinoviruses" herein above, linked, by a covalent linkage, to another amino acid sequence which is at least 90% identical to an amino acid sequence located in the VP2 amino acid sequence of a rhinovirus, as defined in the section "Rhinoviruses" herein above.

The whole amino acid sequence of VP2 is about 270 amino acids long. The amino acid sequence located in the VP2 amino acid sequence which is covalently linked to the VP4 amino acid sequence can be all or part of the VP2 amino acid sequence. When it is only a part of the VP2 amino acid sequence, it can be any portion of the VP2 amino acid sequence. It can be the N-terminal part, the C-terminal part or the central part of the VP2 amino acid sequence. Preferably, the fusion peptide comprises all or part of the most conserved domains of the VP2 amino acid sequence which are located between amino acids 70 and 191 and between amino acids 243 and 297 in the VP0 polyprotein amino acid sequence. In view of the foregoing, the size of the VP2 amino acid sequence that is covalently linked to the VP4 amino acid sequence is at least 30, at least 35, at least 40, at least 50, at least 60, at least 70, at least 100, at least 150, at least 200, at least 250 consecutive amino acids long. The VP4 and VP2 amino acid sequences that are linked together are not necessary contiguous amino acid sequences in the VP0 polyprotein. Preferably the C-terminal end of the VP4 amino acid sequence is covalently linked by a peptide bond to the N-terminal end of the VP2 amino acid sequence.

The different domains of the fusion peptide of the immunogenic composition according to the invention are generally directly coupled to one another. Optionally, in case it facilitates the production process of the fusion peptide, the different domains can be coupled via a linker that may be an amino acid, a peptide of appropriate length, or a different molecule providing the desired features. The skilled person knows how to design appropriate linker molecules, in particular linker peptides based on his common knowledge. For example, peptide linkers can be chosen from the LIP (Loops in Proteins) database (Michalsky et al. (2003) *Prot. Eng.* 56:979-985).

According to an embodiment, the fusion peptide of the immunogenic composition according to the invention comprises, or consists of, an amino acid sequence which is at least 90% identical, at least 95% identical, in particular at least 96% identical, 97%, 98%, 99% or 100% identical to the VP4 amino acid sequence of a rhinovirus, as defined in the section "Rhinoviruses" herein above, linked, by a covalent linkage, in particular a peptide bond, to another amino acid sequence which is at least 90% identical, in particular at least 95%, 96%, 97%, 98%, 99% or 100% identical to an amino acid sequence located in the VP2 amino acid sequence of the same or a different rhinovirus, as defined in the section "Rhinoviruses" herein above. Preferably, the C-terminal end of the VP4 amino acid sequence is covalently linked by a peptide bond to the N-terminal end of the VP2 amino acid sequence.

For instance, a fusion peptide comprising any VP4 amino acid sequence of a rhinovirus strain which is at least 90% identical to the VP4 peptide of the HRV16 serotype (SEQ ID NO: 1) linked to any amino acid sequence located in the VP2 amino acid sequence of a rhinovirus strain which is at least 90% identical to the corresponding amino acid sequence in the VP2 amino acid sequence of the HRV16 serotype rhinovirus (SEQ ID NO: 3) is suitable for the purpose of the invention.

Similarly, a fusion peptide comprising any VP4 amino acid sequence of a rhinovirus strain which is at least 90% identical to the VP4 peptide of the HRV14 serotype (SEQ ID NO: 2) linked to any amino acid sequence located in the VP2 amino acid sequence of a rhinovirus strain which is at least 90% identical to the corresponding amino acid sequence in the VP2 amino acid sequence of the HRV14 serotype rhinovirus (SEQ ID NO: 4) is suitable for the purpose of the invention.

In another embodiment, the fusion peptide of the immunogenic composition according to the invention comprises, or consists of, an amino acid sequence which is at least 80% identical, in particular at least 85%, 90%, 95%, 96%, 97%, 98%, 99%, or 100% identical to an amino acid sequence located in the VP0 polyprotein of a rhinovirus, as defined in the section "Rhinoviruses" herein above.

In particular, said amino acid sequence located in the VP0 polyprotein is an amino acid sequence constituted of from 120 to 370 consecutive amino acids, more particularly from 140 to 340 amino acids, from 160 to 320 amino acids, from 180 to 300 amino acids, from 200 to 280 amino acids or from 220 to 260 amino acids. Preferably the amino acid sequence located in the VP0 polyprotein comprises the whole VP4 amino acid sequence.

As a matter of example, the present inventors demonstrated that a fusion peptide comprising the first 135 N-terminal amino acids of the VP0 polyprotein or the whole VP0 polyprotein of a rhinovirus induces a cross-reactive cell immune response against different serotypes of rhinoviruses, and can also rapidly induces virus clearance in rhinovirus-infected mice.

Accordingly, in a particular embodiment, the fusion peptide of the immunogenic composition according to the invention comprises, or consists of, an amino acid sequence consisting of the first 135 N-terminal amino acids of the VP0 polyprotein of a rhinovirus, as defined in the section "Rhinoviruses" herein above.

More particularly, the fusion peptide of the immunogenic composition according to the invention comprises, or consists of, an amino acid sequence which is at least 80% identical, more particularly at least 90%, 95%, 96%, 97%, 98%, 99% or 100% identical to the amino acid sequence consisting of the first 135 N-terminal amino acids of the VP0 polyprotein of HRV16, said first 135 N-terminal amino acids consisting typically of the sequence (SEQ ID NO: 5)
MGAQVSRQNVGTHSTQNMVSNGSSLNYFNINYFKDAASSGASRLDFSQDP

SKFTDPVKDVLEKGIPTLQSPSVEACGYSDRIIQITRGDSTITSQDVANA

VVGYGVWPHYLTPQDATAIDKPTQPDTSSNRFYTL.

Alternatively, the fusion peptide of the immunogenic composition according to the invention comprises, or consists of, an amino acid sequence which is at least 80% identical, more particularly at least 90%, 95%, 96%, 97%, 98%, 99% or 100% identical to the amino acid sequence consisting of the first 135 N-terminal amino acids of the VP0 polyprotein of HRV14, said first 135 N-terminal amino acids consisting typically of the sequence (SEQ ID NO: 7)
MGAQVSTQKSGSHENQNILTNGSNQTFTVINYYKDAASTSSAGQSLSMDP

SKFTEPVKDLMLKGAPALNSPNVEACGYSDRVQQITLGNSTITTQEAANA

VVCYAEWPEYLPDVDASDVNKTSKPDTSVCRFYTL.

Still particularly, the fusion peptide of the immunogenic composition according to the invention comprises, or consists of, an amino acid sequence which is at least 80% identical, more particularly at least 90%, 95%, 96%, 97%, 98%, 99% or 100% identical to the whole amino acid sequence of the VP0 polyprotein of HRV16 or of the VP0 polyprotein of HRV14, as defined in the section "Rhinoviruses" herein above.

Aiming at reducing the number of antigens, the present inventors also designed fusion peptides between the conserved regions situated in the VP0 polyprotein and the ones situated in the RNA polymerase, which retained a global antigen size easy to express.

Accordingly, in a particular embodiment, the fusion peptide of the immunogenic composition according to the invention comprises, or consists, of (i) an amino acid sequence that is at least 90% identical, more particularly at least 95%, 96%, 97%, 98%, 99% or 100% identical to the VP4 amino acid sequence of one rhinovirus, as defined in the section "Rhinoviruses" herein above, linked, by a covalent linkage, to (ii) an amino acid sequence which is at least 90% identical, in particular at least 95%, 96%, 97%, 98%, 99% or 100% identical to an amino acid sequence located in the last 363 C-terminal amino acids of the RNA polymerase of the same or of a different rhinovirus.

For instance, a fusion peptide comprising any VP4 amino acid sequence of a rhinovirus strain which is at least 90% identical to the VP4 peptide of the HRV16 serotype (SEQ ID NO: 1) or of the HRV14 serotype (SEQ ID NO: 2) linked to any amino acid sequence located in the last 363 C-terminal amino acids of the RNA polymerase of a rhinovirus strain which is at least 90% identical to the corresponding amino acid sequence located in the last 363 C-terminal amino acids of the RNA polymerase of the HRV16 serotype (SEQ ID NO: 13) or of the HRV14 serotype (SEQ ID NO: 14) is suitable for the purpose of the invention. Preferably the C-terminal end of the VP4 amino acid sequence is covalently linked by a peptide bond to the N-terminal end of the C-terminal domain of the RNA polymerase amino acid sequence In particular, said amino acid sequence located in the last 363 C-terminal amino acids of the RNA polymerase of a rhinovirus is an amino acid sequence constituted of about from 100 to 363 consecutive amino acids of the RNA polymerase amino acid sequence, more particularly of from 105 to 350 consecutive amino acids, 110 to 340, 120 to 330, 140 to 320, 160 to 300, 180 to 280, 200 to 260 or 220 to 240 consecutive amino acids.

In particular, the present inventors demonstrated that a fusion peptide comprising the last 105 C-terminal amino acids of the RNA polymerase retained the ability to induce a cross-reactive immune response.

Accordingly, in a particular embodiment, the amino acid sequence located in the last 363 C-terminal amino acids of the RNA polymerase of a rhinovirus included in the fusion peptide of the immunogenic composition according to the invention consists of the last 105 C-terminal amino acids of the RNA polymerase of a rhinovirus, as defined in the section "Rhinoviruses" herein above.

More particularly, the amino acid sequence located in the last 363 C-terminal amino acids of the RNA polymerase of a rhinovirus included in the fusion peptide of the immunogenic composition according to the invention consists of the last 105 C-terminal amino acids of the RNA polymerase of HRV16, said last 105 C-terminal amino acids consisting typically of the sequence:

(SEQ ID NO: 9)
ADKSSEFKELDYGNVTFLKRGFRQDDKYKFLIHPTFPVEEIYESIRWTKK

PSQMQEHVLSLCHLMWHNGPEIYKDFETKIRSVSAGRALYIPPYELLRHE

WYEKF.

In another embodiment, the amino acid sequence located in the last 363 C-terminal amino acids of the RNA polymerase of a rhinovirus included in the fusion peptide of the immunogenic composition according to the invention consists of the last 105 C-terminal amino acids of the RNA polymerase of HRV14, said last 105 C-terminal amino acids consisting typically of the sequence:

(SEQ ID NO: 10)
PDKSETFTKMTWENLTFLKRYFKPDQQFPFLVHPVMPMKDIHESIRWTKD

PKNTQDHVRSLCMLAWHSGEKEYNEFIQKIRTTDIGKCLILPEYSVLRRR

WLDLF.

According to another embodiment, the fusion peptide of the immunogenic composition according to the invention comprises, or consists of, an amino acid sequence which is at least 90% identical, at least 95% identical, in particular at least 96% identical, 97%, 98%, 99% or 100% identical to the VP4 amino acid sequence of a rhinovirus, as defined in the section “Rhinoviruses” herein above, linked, by a covalent linkage, in particular a peptide bond, to (ii) an amino acid sequence which is at least 90% identical, in particular at least 95%, 96%, 97%, 98%, 99% or 100% identical to an amino acid sequence located in the VP2 amino acid sequence of the same or of a different rhinovirus, as defined in the section “Rhinoviruses” herein above, which is linked, by a covalent linkage, in particular a peptide bond, to (iii) an amino acid sequence which is at least 90% identical, in particular at least 95%, 96%, 97%, 98%, 99% or 100% identical to an amino acid sequence located in the last 363 C-terminal amino acids of the RNA polymerase of the same or of a different rhinovirus.

For instance a fusion peptide comprising any VP4 amino acid sequence of a rhinovirus strain which is at least 90% identical to the VP4 peptide of the HRV16 serotype (SEQ ID NO: 1) or of the HRV14 serotype (SEQ ID NO: 2) coupled to any amino acid sequence located in the VP2 amino acid sequence of a rhinovirus strain which is at least 90% identical to the corresponding amino acid sequence located in the VP2 amino acid sequence of the HRV16 serotype (SEQ ID NO: 3) or of the HRV14 serotype (SEQ ID NO: 4), which is coupled to any amino acid sequence located in the last 363 C-terminal amino acids of the RNA polymerase of a rhinovirus strain which is at least 90% identical to the corresponding amino acid sequence located in the last 363 C-terminal amino acids of the RNA polymerase of the HRV16 serotype (SEQ ID NO: 13) or of the HRV14 serotype (SEQ ID NO: 14) is suitable for the purpose of the invention. Preferably the C-terminal end of the VP4 amino acid sequence is covalently linked by a peptide bond to the N-terminal end of the VP2 amino acid sequence and the C-terminal end of said VP2 amino acid sequence is covalently linked by a peptide bond to the N-terminal end of the C-terminal domain of the RNA polymerase sequence.

In particular, the fusion peptide of the immunogenic composition according to the invention comprises, or consists of, an amino acid sequence which is at least 80% identical, more particularly at least 90%, 95%, 96%, 97%, 98%, 99% or 100% identical to the amino acid sequence consisting of the first 135 N-terminal amino acids of the VP0 polyprotein of a rhinovirus, linked, by a covalent linkage, in particular a peptide bond, to (ii) an amino acid sequence which is at least 90% identical, in particular at least 95%, 96%, 97%, 98%, 99% or 100% identical to an amino acid sequence located in the last 363 C-terminal amino acids of the RNA polymerase of the same or a different rhinovirus. More particularly, the fusion peptide of the immunogenic composition according to the invention comprises, or consists, of an amino acid sequence which is at least 80% identical, in particular at least 85% identical, 90%, 95%, 96%, 97%, 98%, 99%, or 100% identical to the amino acid sequence (SEQ ID NO: 11)
MGAQVSRQNVGTHSTQNMVSNGSSLNYFNINYFKDAASSGASRLDFSQDP

SKFTDPVKDVLEKGIPTLQSPSVEACGYSDRIIQITRGDSTITSQDVANA

VVGYGVWPHYLTPQDATAIDKPTQPDTSSNRFYTLADKSSEFKELDYGNV

TFLKRGFRQDDKYKFLIHPTFPVEEIYESIRWTKKPSQMQEHVLSLCHLM

WHNGPEIYKDFETKIRSVSAGRALYIPPYELLRHEWYEKF.

In another particular embodiment of the invention, the fusion peptide of the immunogenic composition of the invention comprises, or consists, of an amino acid sequence which is at least 80% identical, in particular at least 85% identical, 90%, 95%, 96%, 97%, 98%, 99% or 100% identical to the amino acid sequence (SEQ ID NO: 12)
MGAQVSTQKSGSHENQNILTNGSNQTFTVINYYKDAASTSSAGQSLSMDP

SKFTEPVKDLMLKGAPALNSPNVEACGYSDRVQQITLGNSTITTQEAANA

VVCYAEWPEYLPDVDASDVNKTSKPDTSVCRFYTLPDKSETFTKMTWENL

TFLKRYFKPDQQFPFLVHPVMPMKDIHESIRWTKDPKNTQDHVRSLCMLA

WHSGEKEYNEFIQKIRTTDIGKCLILPEYSVLRRRWLDLF.

Nucleic Acids

The present invention also relates to an immunogenic composition comprising an isolated polynucleotide comprising a nucleic acid sequence corresponding to (i.e. encoding) at least one of the peptide a) or b) defined in the section “Peptides” herein above, or fusion peptide defined in the section “Fusion peptides” herein above and designed such that it can be administered to mammals, in particular to human beings. Usually the nucleic acid sequence placed under the control of the elements necessary for its expression in a mammalian cell, in particular in human cells, is incorporated in a plasmid, which can be further formulated in a delivery vehicle such as liposomes to facilitate its introduction into the host cell.

As used herein, the term “nucleic acid” includes DNA and RNA and can be either double stranded or single stranded.

In the context of the invention, the expression “elements necessary for expression in a mammalian cell” is understood to mean all the elements which allow the transcription of a DNA or DNA fragment into mRNA and the translation of the latter into protein, inside a mammalian cell, such as a human cell. Typically, the elements necessary for the expression of a nucleic acid in a mammalian cell include a promoter that is functional in the selected mammalian cell and can be constitutive or inducible; a ribosome binding site; a start codon (ATG) if necessary; a region encoding a signal peptide (e.g., a lipidation signal peptide); a stop codon; and a 3' terminal region (translation and/or transcription terminator). Other transcription control elements, such as enhancers, operators, and repressors can be also operatively associated with the polynucleotide to direct transcription and/or translation into the cell. The signal peptide-encoding region is preferably adjacent to the nucleic acid included in the immunogenic composition of the invention and placed in proper reading frame. The signal peptide-encoding region can be homologous or heterologous to the DNA molecule encoding the mature peptide or fusion peptide of the invention and can be specific to the secretion apparatus of the host used for expression. The open reading frame constituted by the nucleic acid included in the immunogenic composition of the invention, solely or together with the signal peptide, is placed under the control of the promoter so that transcription and translation occur in the host system. Promoters, (and signal peptide encoding regions) are widely known and available to those skilled in the art.

Lastly, the nucleic acid sequences may be codon optimized such that the transcription of the DNA encoding the peptides and/or the fusion peptides of the invention is enhanced and/or the translation of the mRNA encoding the peptides and/or the fusion peptides is prolonged.

A "codon-optimized DNA or mRNA sequence" means a nucleic acid sequence that has been adapted for a better expression into the host cell, such as a human cell by replacing one or more codons with one or more codons that are more frequently used in the genes of said host cell as described in US 2004/0209241 in the case of codon-optimized DNA sequences or to maximize the G/C content of the mRNA sequence according to the host cell used as described in US 2011/02699950 in the case of codon-optimized mRNA sequences. The codon optimization of the nucleic acid sequences is properly managed such that it does not change significantly the amino acid sequence of the peptides and/or the fusion peptides, as described in the sections "Peptides" and "Fusion peptides" herein above, which are expressed in the host cells.

Immunogenic Composition

In the context of the invention, the expression "immunogenic composition" refers to a composition of matter intended to be administered to a subject that comprises at least one antigen or induces the expression of at least one antigen of a rhinovirus (in the case of nucleic acid immunization) which has the capability to elicit an immunological response in the subject to which it is administered. Such an immune response can be a cellular and/or antibody-mediated immune response directed at least against the antigen of the composition.

More specifically, the immunogenic composition of the invention comprises an isolated peptide as defined in the section "Peptides" herein above, a fusion peptide as defined in the section "Fusion peptides" herein above and/or an isolated polynucleotide as defined in the section "Nucleic acids" herein above.

When the immunogenic composition of the invention comprises at least one peptide as defined in the section "Peptides" herein above and/or at least one fusion peptide as defined in the section "Fusion peptides" herein above, it also comprises a Th1 adjuvant.

A "Th1 adjuvant" in the meaning of the invention is defined from the ratio between IFN-γ and IL-5 cytokines that are produced by the splenocytes of mice that have been previously immunized by subcutaneous route with a peptide or a fusion peptide of the immunogenic composition according to the invention in presence of the tested adjuvant. More specifically, the splenocytes are harvested 28 days after the immunization and restimulated in vitro with a pool of 15 mers peptides (able to be presented by class I and II MHC) overlapping on 11 amino acids, covering the amino acid sequence of the same peptide or fusion peptide in a culture medium according to the protocol described in example 3. After 3 days of stimulation, culture supernatants are harvested for measuring IFN-γ and IL-5 cytokines by Cytometry Bead Array. If the ratio IFN-γ/IL-5 is >5, preferably >10, the tested adjuvant is considered as a Th1 adjuvant.

Examples of Th1 adjuvants promoting a Th1 immune response include TLR-9 agonists such as CpG oligonucleotides, or TLR-4 agonists.

In a particular embodiment, the Th1 adjuvant used in the immunogenic compositions of the invention comprises a CpG oligonucleotide. It can be used in an aqueous solution, formulated in Oil in water Emulsion, for instance with incomplete Freund's adjuvant or delivered by other means. As examples of suitable CpG oligobucleotide sequences mention is made of CpG ODN 1826 (sequence 5'-TCCATGACGTTCCTGACGTT-3' (SEQ ID NO: 38)), CpG ODN 2216 (sequence 5'ggGGGACGATCGTCggggg-3' (SEQ ID NO: 39)), CpG 2336 (sequence 5'-gggGACGACGTCGTGgggggg-3' (SEQ ID NO: 40)), or CpG 7909 (5'-TCGTCGTTTTGTCGTTTTGTCGTT-3' (SEQ ID NO: 41)), but other stimulatory sequences can be used for the purpose of the invention.

The immunogenic compositions of the invention can further comprise a pharmaceutically acceptable vehicle.

In the context of the invention, the expression "pharmaceutically acceptable vehicle" refers to a vehicle that is physiologically acceptable to a treated mammal, in particular to humans, while retaining the prophylactic or therapeutic properties of the compound with which it is administered. One exemplary pharmaceutically acceptable vehicle is physiological saline. Other physiologically acceptable vehicles and their formulations are known to those skilled in the art and examples are described, for example, in Remington's Pharmaceutical Sciences, ($18^{th}$ edition), ed. A. Gennaro, 1990, Mack Publishing Company, Easton, Pa.

The compositions can be formulated for use in a variety of drug delivery systems. One or more physiologically acceptable excipients or carriers can also be included in the compositions for proper formulation.

The immunogenic compositions can be administered intranasally (e.g., by aerosol inhalation or nose drops), parenterally (e.g., by intramuscular, subcutaneous, intravenous route, intradermally, transcutaneously, transdermally or percutaneously), cutaneously, orally, mucosally, intrapulmonary and/or by intratracheal delivery, or by topical application. Sustained release administration is also encompassed in the invention, by such means as depot injections or erodible implants or components. Thus, the invention provides immunogenic compositions for mucosal or parenteral administration that include the peptides as defined in the section "Peptides" herein above, the fusion peptides as defined in the section "Fusion peptides" in the presence of the Th1 adjuvant as defined above, and/or the polynucleotides as defined in the section "Nucleic acids" herein above, dissolved or suspended in an acceptable vehicle, preferably an aqueous carrier, e.g., water, buffered water, saline, PBS, and the like. The immunogenic compositions may contain pharmaceutically acceptable auxiliary substances as required to approximate physiological conditions, such as pH adjusting and buffering agents, tonicity adjusting agents, wetting agents, detergents and the like. The invention also provides immunogenic compositions for oral delivery, which may contain inert ingredients such as binders or fillers for the formulation of a tablet, a capsule, and the like. Further, this invention provides immunogenic compositions for cutaneous or local administration, which may contain inert ingredients such as solvents or emulsifiers suitable for penetration through the skin, for the formulation of a cream, an ointment, or incorporation in a patch.

For oral administration, the immunogenic composition may be of any of several forms including, for example, a capsule, a tablet, a suspension, or liquid, among others.

Injectable preparations, under the form of sterile injectable aqueous solutions or suspensions, such as liposomes, or emulsions such as Oil in Water emulsions, may be formulated according to known methods using suitable dispersing, wetting agents, suspending agents, emulsifying agents and the like. Suitable vehicles and solvents that may be employed are water, Ringer's solution, isotonic sodium chloride solution, phosphate or Tris buffer among others. In addition, sterile, fixed oils are conventionally employed for the preparation of emulsions. For this purpose, any bland fixed oil may be employed, including synthetic mono- or diglycerides, squalene.

The immunogenic compositions may also be prepared in a solid form (including granules, powders or suppositories).

These immunogenic compositions may be sterilized by conventional sterilization techniques, or may be sterile filtered. The resulting aqueous solutions may be packaged and stored under liquid form or lyophilized, the lyophilized preparation being reconstituted with a sterile aqueous carrier prior to administration. The pH of the preparations typically will be between 3 and 11, e.g., between 5 and 9, 6 and 8, or 7 and 8, such as 7 to 7.5. The resulting compositions in solid form may be packaged in multiple single dose units, each containing an effective amount of peptides as defined in the section "Peptides" herein above, fusion peptides as defined in the section "Fusion peptides", and a Th1 adjuvant, and/or polynucleotides as defined in the section "Nucleic acids" herein above, such as in a vial. If there is an incompatibility between the Th1 adjuvant and the peptide or fusion peptide, they can be stored in separate packages and mixed extemporaneously before administration to the subject.

The immunogenic composition according to the present invention may be prepared using any conventional method known to those skilled in the art. Conventionally the peptides and/or fusion peptides according to the invention are mixed with a pharmaceutically acceptable diluent or excipient, such as water or phosphate buffered saline solution, wetting agents, fillers, emulsifier and stabilizer. The excipient or diluent will be selected as a function of the pharmaceutical form chosen, of the method and route of administration and also of pharmaceutical practice. Suitable excipients or diluents and also the requirements in terms of pharmaceutical formulation, are described in Remington's Pharmaceutical Sciences, which represents a reference book in this field.

Medical Indications

The present invention also concerns a method for inducing a specific cross-reactive cell-mediated immune response in a mammal directed against at least two serotypes of rhinoviruses, more particularly against at least two serotypes of type A and/or type B rhinoviruses, comprising administering to a mammal an effective amount of an immunogenic composition as defined in the section "Immunogenic composition" herein above.

The present invention further concerns an immunogenic composition as defined in the section "Immunogenic composition" herein above" for use in a mammal to induce a cross-reactive cell-mediated immune response against at least two serotypes of rhinoviruses, in particular against at least two serotypes of type A and/or type B rhinoviruses.

The present invention also concerns the use of a peptide a) or b) as defined in the section "Peptides" herein above or a polynucleotide as defined in the section "Nucleic acids" herein above, for the manufacture of an immunogenic composition intended to induce a cross-reactive cell-mediated immune response against at least two serotypes of rhinoviruses, in particular against at least two serotypes of type A and/or type B rhinoviruses in a mammal.

Primarily the immune response that is induced by an immunogenic composition of the invention is a specific cell-mediated immune response not only directed to the homologous serotype(s) of rhinovirus from which the immunogenic composition is derived but also to other (heterologous) serotypes of rhinoviruses of the same group of rhinoviruses, which can extend to serotypes of rhinoviruses of another group of rhinoviruses. In particular, the cell-mediated immune response induced by an immunogenic composition of the invention overtakes the "inter-group barrier" because it is in particular directed against serotypes of type A and type B rhinoviruses. Such cellular immune response is named specific cross-reactive cellular immune response (or specific cross-reactive cell-mediated immune response), insofar it is not limited to the homologous serotype of rhinovirus against which the subject has been immunized. The cell-mediated immune response induced by the immunogenic composition of the invention is Th1- and/or Tc1-oriented.

In the context of the invention, the expression "inducing a specific cell-mediated immune response" means the generation of a specific T lymphocyte response following the administration of an immunogenic composition in a subject.

The two main cellular effectors of the specific T lymphocyte response are the helper T-cells and the cytototoxic T lymphocytes (CTLs).

CD4+"helper" T-cells or helper T-cells, are immune response mediators, and play an important role in establishing and maximizing the capabilities of the adaptive immune response. These cells can have to some extent a direct cytotoxic activity, but, in essence "manage" the immune response, by directing other cells involved in the protection of organisms against pathogens. The activation of a naive helper T-cell causes it to release cytokines, which influences the activity of many cell types such as B lymphocytes, CTLs, and APCs (Antigen Presenting Cells) that activated it. Helper T-cells require a much milder activation stimulus than cytotoxic T-cells. Helper T-cells can provide extra signals that "help" activate cytotoxic cells. Two types of effector CD4+ helper T cell responses can be induced by a professional APC, designated Th1 and Th2. The measure of cytokines associated with Th1 or Th2 responses will give a measure of successful immunization. This can be achieved by specific ELISA or ELISPOT designed for measurement of Th1-cytokines such as IFN-γ, IL-2, and others, or Th2-cytokines such as IL-4, IL-5, IL-13 among others.

As used herein, the expression "helper T-cell-mediated immune response" refers to an immune response wherein $CD4^+$ T-cells or helper T-cells are activated and secrete lymphokines to stimulate both cell-mediated and antibody-mediated branches of the immune system. As known from the skilled person, helper T-cell activation promotes lymphokine secretion, immunoglobulin isotype switching, affinity maturation of the antibody response, macrophage activation and/or enhanced activity of natural killer and cytotoxic T-cells. Lymphokines are proteins secreted by lymphocytes that affect their own activity and/or the activity of other cells. Lymphokines include, but are not limited to, interleukins and cytokines, e.g., IL-2, IL-4, IL-5, IL-6, IL-10, IL-12, or IFN-γ.

As well-known from the skilled person, helper T-cells differentiate into two major subtypes of cells known as Th1 and Th2 cells (also known as Type 1 and Type 2 helper T cells, respectively).

As known from the skilled person, Th1 cells mainly secrete IL-2 and IFN-γ. They promote cellular immune response by maximizing the killing efficacy of macrophages and the proliferation of cytotoxic $CD8^+$ T-cells. Additionally, the type 1 cytokine IFN-γ increases the production of IL-12 by dendritic cells and macrophages, and, via positive feedback, IL-12 stimulates the production of IFN-γ in helper T-cells, thereby promoting the Th1 profile. IFN-γ also inhibits the production of cytokines such as IL-4, an important cytokine associated with the Type 2 response, and thus it also acts to preserve its own response.

On the contrary, Th2 cells mainly secrete IL-4, IL-5 and IL-13, and promote humoral immune response by stimulating B cells into proliferation, inducing B-cell antibody class switching. The Type 2 response further promotes its own profile using two different cytokines. IL-4 acts on helper T-cells to promote the production of Th2 cytokines (including itself), while IL-10 inhibits a variety of cytokines including IL-2 and IFN-γ in helper T-cells and IL-12 in dendritic cells and macrophages.

Preferably, said cell-mediated immune response induced by the immunogenic composition of the invention is primarily a Th1 cell-mediated immune response.

The induction of a Th1 oriented cell-mediated immune response by the immunogenic composition of the invention may be determined from the ratio between IFN-γ and IL-5 cytokines that are produced by the splenocytes of mice that have been previously immunized by subcutaneous route with the immunogenic composition according to the invention. More specifically, the splenocytes are harvested 28 days after the immunization and stimulated in vitro with a pool of 15 mers peptides overlapping on 11 amino acids covering the amino acid sequence of the peptide or fusion peptide included in the immunogenic composition or encoded by a nucleic acid included in the immunogenic composition, in a culture medium according to the protocol described in example 3. After 3 days of stimulation, culture supernatants are harvested for measuring IFN-γ and IL-5 cytokines by Cytometry Bead Array. If the ratio IFN-γ/IL-5 is >5, preferably >10, the immune response induced is a Th1 oriented cell-mediated immune response. Furthermore, since the Th1 oriented cell-mediated immune response is a cross-reactive cell-mediated immune response, the splenocytes harvested 28 days after immunization can also be stimulated in vitro with a pool of 15 mers peptides overlapping on 11 amino acids, covering the amino acid sequence of a corresponding peptide or fusion peptide from at least one other serotype of type A and/or type B rhinovirus and produce in the cell culture supernatant amounts of IFN-γ and IL-5 cytokines such that the ratio IFN-γ/IL-5 is >5, preferably >10 after dosing by Cytometry Bead Array.

In the context of the invention, a Tc1 response may also be observed in addition to the Th1 cell-mediated immune response.

Cytotoxic T cells (also known as Tc, killer T cell, or cytotoxic T-lymphocyte (CTL)), which express generally the CD8 marker, are a sub-group of T cells and may also be involved in the T cell-mediated immune response. They induce the death of cells that are infected with viruses (and other pathogens). These CTLs directly attack other cells carrying certain foreign or abnormal molecules on their surface. The ability of such cellular cytotoxicity can be detected using in vitro cytolytic assays (chromium release assay). Thus, induction of a specific cellular immunity can be demonstrated by the presence of such cytotoxic T cells, when antigen-loaded target cells are lysed by specific CTLs that are generated in vivo following vaccination or infection.

Similarly to helper T-cells, $CD8^+$ T-cells include distinct subsets, which were termed, analogously to the Th1/Th2 terminology, Tc1 and Tc2.

The Tc1 immune response involves specific IFN-γ-producing $CD8^+$ T-cells which are activated, proliferate and produce IFN-γ upon specific antigen stimulation. The level of IFN-γ-producing $CD8^+$ T-cells can be measured by ELISPOT and by flow cytometry measurement of intracellular IFN-γ in these cells.

Naive cytotoxic T cells are activated when their T-cell receptor (TCR) strongly interacts with a peptide-bound MHC class I molecule. This affinity depends on the type and orientation of the antigen/MHC complex, and is what keeps the CTL and infected cell bound together. Once activated the CTL undergoes a process called clonal expansion in which it gains functionality, and divides rapidly, to produce an army of “armed” effector cells. Activated CTL will then travel throughout the body in search of cells bearing that unique MHC Class I+ peptide. This could be used to identify such CTLs in vitro by using peptide-MHC Class I tetramers in flow cytometric assays.

When exposed to these infected cells, effector CTL release perforin and granulysin, cytotoxins which form pores in the target cell’s plasma membrane, allowing ions and water to flow into the infected cell, and causing it to burst or lyse. CTL release granzyme, a serine protease that enters cells via pores to induce apoptosis (cell death). Release of these molecules from CTL can be used as a measure of successful induction of cellular immune response following vaccination. This can be done by enzyme linked immunosorbant assay (ELISA) or enzyme linked immunospot assay (ELISPOT) where CTLs can be quantitatively measured. Since CTLs are also capable of producing important cytokines such as IFN-γ, quantitative measurement of IFN-γ-producing CD8 cells can be achieved by ELISPOT and by flow cytometric measurement of intracellular IFN-γ in these cells.

In particular, the induction of a Tc1 immune response by the immunogenic composition of the invention may be determined from the level of IFN-γ cytokine that is produced in $CD8^+$ T-cells of mice that have been previously immunized by subcutaneous route with the immunogenic composition according to the invention. More specifically, the splenocytes are harvested 28 days after the immunization and stimulated in vitro with a pool of 15 mers peptides overlapping on 11 amino acids covering the amino acid sequence of the peptide or fusion peptide included in the immunogenic composition or encoded by a nucleic acid included in the immunogenic composition, in a culture medium. Brefeldin A (BFA) is added to inhibit cytokine secretion, and cells are stimulated for 5 h, followed by overnight storage. The following day, cells are permeabilized, fixed, stained, and the percentage of $CD8^+$ IFN-$\gamma^+$ and $CD8^+$ $IL5^+$ cells in the splenocyte population is measured by flow cytometry after intracellular cytokine staining (ICS). If the ratio $CD8^+$ IFN-$\gamma^+$/$CD8^+$ $IL5^+$ is higher than 1, the immune response is considered as a Tc1 immune response.

In the context of the invention, the expression “inducing a cross-reactive immune response” means that an immune response is induced both against the HRV serotype from which the peptide, fusion peptide or nucleic acid included in the immunogenic composition of the invention is derived (i.e. "cellular immune response to the homologous serotype"), and against at least a second HRV serotype different from the HRV serotype from which the peptide, fusion peptide or nucleic acid included in the immunogenic composition of the invention is derived (i.e. "cellular immune response to the heterologous serotype").

Therefore, in an embodiment, the peptide, fusion peptide and/or nucleic acid of the immunogenic composition of the invention induce a cellular immune response to both homologous and heterologous serotypes of rhinoviruses, as defined above.

More particularly, an immune response may be induced both against the HRV serotype from which the peptide, fusion peptide or nucleic acid included in the immunogenic composition of the invention is derived, and against at least a second HRV serotype which is of a different group from the HRV serotype from which the peptide, fusion peptide or nucleic acid included in the immunogenic composition of the invention is derived. In other words, an inter-group reactive immune response may be induced by the immunogenic composition of the invention.

In a particular embodiment, the peptide, fusion peptide and/or nucleic acid of the immunogenic composition of the invention are derived from a serotype of type A rhinoviruses, in particular from HRV16, HRV29 or HRV1B, and an immune response is induced against the same serotype of type A rhinoviruses and at least another serotype of type A and/or type B rhinoviruses, in particular HRV14.

In another particular embodiment, the peptide, fusion peptide and/or nucleic acid of the immunogenic composition of the invention are derived from a strain of type B rhinoviruses, in particular from HRV14, and an immune response is induced against the same serotype of type B rhinoviruses and at least another serotype of type B and/or type A rhinoviruses, in particular HRV16, HRV29 and/or HRV1B.

In another particular embodiment, the peptide, fusion peptide and/or nucleic acid of the immunogenic composition of the invention are from a strain of major-group type A or type B rhinoviruses, in particular from HRV16 or HRV14, and an immune response is induced against the same strain of major-group type A or type B rhinoviruses and at least another strain of minor-group type B or type A rhinoviruses, in particular HRV1B and/or HRV29, and/or at least another strain of major-group type A or type B rhinoviruses.

Therefore, the cellular immune response induced by an immunogenic composition of the invention overtakes the "inter-group barrier" among rhinoviruses since it is at least directed against serotypes of type A Human rhinoviruses and type B Human rhinoviruses.

The immunogenic compositions according to the invention are therefore able to induce a cross-reactive cell-mediated immune response against several HRV serotypes which can also be considered as an inter-group cell-mediated immune response.

In a particular embodiment, the cell-mediated immune response induced by the administration of the immunogenic compositions of the invention is boosted after infection by a rhinovirus.

In the context of the invention, the phrase "cell-mediated immune response is boosted after infection by a rhinovirus" means the induction of a cross-reactive specific cell-mediated immune response after rhinovirus infection of subjects already immunized with an immunogenic composition of the invention.

Although the peptide, fusion peptide and nucleic acid included in the immunogenic composition according to the invention were designed by the inventors to induce T cell-mediated immune response, T cell help may also contribute to the development of an effective humoral immune responses. The effect of immunization with the immunogenic composition of the invention on the humoral immune response to subsequent infection with a rhinovirus was also studied by the inventors to determine if immunization-induced T cell-mediated immune responses could indirectly enhance this aspect of immunity.

The present inventors demonstrated that, while only administering the immunogenic compositions of the invention to a subject induced a cross-reactive non neutralizing antibody response, it advantageously enabled inducing a specific neutralizing antibody response when a rhinovirus infection occurred in said subject. Furthermore, the clearance of rhinovirus infection was very fast.

The present invention therefore also concerns a method for inducing a specific neutralizing antibody response in a mammal when said mammal is infected by a rhinovirus, comprising administering to a mammal an effective amount of an immunogenic composition as defined in the section "Immunogenic composition" herein above.

The present invention further concerns an immunogenic composition as defined in the section "Immunogenic compositions" herein above, for use in a mammal (i.e. in humans) to induce a specific neutralizing antibody response when said mammal is infected by a rhinovirus.

The present invention also concerns the use of a peptide as defined in the section "Peptides" herein above or a nucleic acid as defined in the section "Nucleic acids" herein above, for the manufacture of an immunogenic composition intended to induce a specific neutralizing antibody response in a mammal when said mammal is infected by a rhinovirus.

In the context of the invention, a "neutralizing antibody" refers to an antibody which prevents the replication cycle of rhinoviruses to occur in permissive cells of a subject. Permissive cells are cells that allow the penetration and the multiplication of the virus. In the context of the invention, lung cells are highly permissive to rhinovirus infection.

In a particular embodiment, the immunogenic composition as defined in the section "Immunogenic compositions" herein above, is therefore for use in a mammal to induce a specific cross-reactive cell-mediated immune response against at least two serotypes of rhinoviruses followed by a specific neutralizing antibody response when said mammal is infected by said rhinoviruses.

The immunogenic compositions of the invention can thus be administered for prophylactic ("cross-protective") treatments. In prophylactic applications, immunogenic compositions can be administered to a subject (e.g. a human subject) with increased susceptibility to HRV infection. Immunogenic compositions of the invention will be administered to a subject in an amount sufficient to accelerate virus clearance, to reduce or prevent the onset of clinical or subclinical disease or avoid viral complications associated with the infectious virus in the body, in particular in the lungs.

The present invention therefore also concerns a method to shorten or prevent rhinovirus infection in a mammal, and/or to reduce or prevent the clinical symptoms associated with the infection in a mammal, comprising administering to a mammal an effective amount of an immunogenic composition as defined in the section "Immunogenic composition" herein above.

The present invention further concerns an immunogenic composition as defined in the section "Immunogenic composition" herein above for use to shorten or prevent rhinovirus infection in a mammal and/or to reduce or prevent the clinical symptoms associated with the infection.

The present invention also concerns the use of a peptide as defined in the section "Peptides" herein above or a nucleic acid as defined in the section "Nucleic acids" herein above, for the manufacture of an immunogenic composition intended to shorten or prevent rhinovirus infection in a mammal and/or to reduce or prevent the clinical symptoms associated with the infection.

Since the immunogenic composition of the invention protects at least to some extent against infection by rhinoviruses, it is therefore suitable for use as a vaccine to prevent rhinovirus infection.

As used herein, the term "vaccine" refers to as an immunogenic composition intended to elicit an immune response with the aim to establish full or partial protecting immunity to disease, in particular against infective disease.

Determination of an appropriate dosage amount and regimen can readily be determined by those skilled in the art. The immunogenic composition can be only administered once but a prime/boost regimen is generally used. Usually at least one or two boosting doses subsequent to priming dose are given to the subject. Time interval between each immunization may vary according to the subject to be immunized or other factors such as the formulation or the route of administration of the immunogenic composition but usually a time interval of at least 15 days, at least one month, at least two months or at least six months are respected between each immunization.

The effective amount of the immunogenic composition of the invention applied to mammals (e.g., humans) can be determined by those skilled in the art with consideration of individual differences in age, weight, immune system integrity, and the like, such that it produces the desirable effect in the immunized subject, which is at least the shortening of virus infection and/or the lessening of clinical symptoms in the infected individual.

Administration of an immunogenic composition of the present invention to a mammal may be accomplished using any of a variety of techniques known to those of skill in the art. The composition may be processed in accordance with conventional methods of pharmacy to produce medicinal agents for administration to patients, including humans and other mammals.

As mentioned above, the immunogenic composition may be administered intranasally (e.g., by aerosol inhalation or nose drops), parenterally (e.g., by intramuscular, subcutaneous, or intravenous route, intradermally, transcutaneously, transdermally or percutaneously), cutaneously, orally, mucosally, intrapulmonary and/or by intratracheal delivery and/or by topical application, in dosage unit formulations.

While the compositions of the invention can be administered as the sole active pharmaceutical agent, they can also be used in combination with one or more other compositions or agents (i.e., other immunogenic targets, co-stimulatory molecules). When administered as a combination, the individual components can be formulated as separate compositions administered at the same time or different times, or the components can be combined as a single composition.

All of the features described herein (including any accompanying claims, abstract and drawings), and/or all of the steps of any method or process so disclosed, may be combined with any of the above aspects in any combination, except combinations where at least some of such features and/or steps are mutually exclusive.

The present invention will be further illustrated by the following figures and examples.

n=10 mice/group. *: $p<0.001$, : $p<0.01$.

Figure 2:
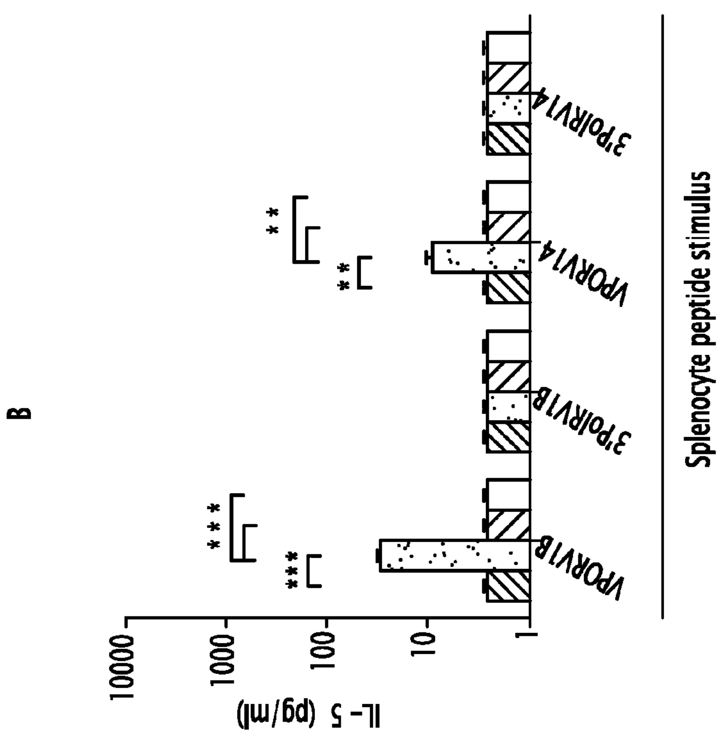
Figure 2:
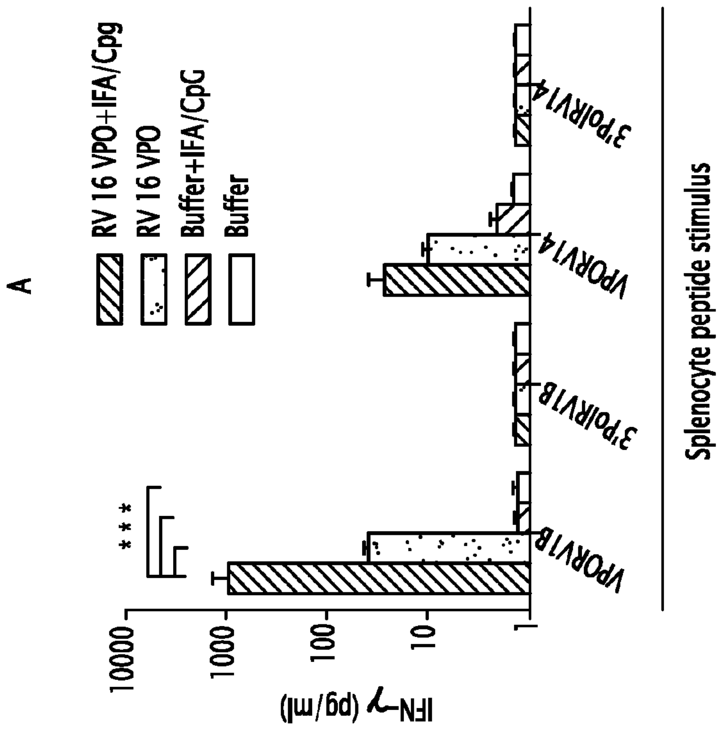

FIG. 2 is a set of histograms representing the supernatant IFN-γ (panel A) and IL-5 (panel B) level (pg/ml), measured by cytometric bead array in splenocytes of mice immunized subcutaneously with HRV16 VP0 protein (RV16 VP0) or buffer, with or without IFA/CpG adjuvant (IFA/Cpg), after stimulation of splenocytes with VP0 from HRV1B (VP0 RV1B) or from HRV14 (VP0 RV14) or 3'Pol peptide pools from HRV1B (3'Pol RV1B) or from HRV14 (3'Pol RV14), the splenocytes being harvested 28 days post-immunization.

n=10 mice/group. *: $p<0.001$, : $p<0.01$.

Figure 3:
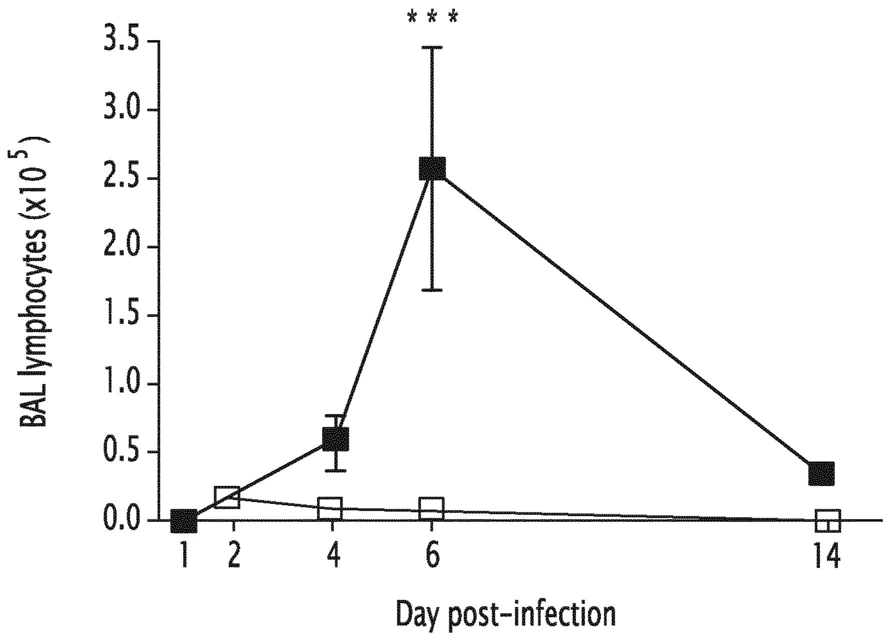

FIG. 3 is a graph representing the number of lymphocytes (×$10^5$) in bronchoalveolar lavage (BAL), in mice immunized subcutaneously with HRV16 VP0 protein plus IFA/CpG adjuvant (immunized), or with IFA/CpG adjuvant only (adjuvant), and challenged intranasally with HRV1B (group RV-immunized (■) and group RV-adjuvant (□)) or mock challenged with PBS (group PBS-immunized (○)), the lymphocytes being counted by cytospin assay. ***: $p<0.001$.

Figure 4:
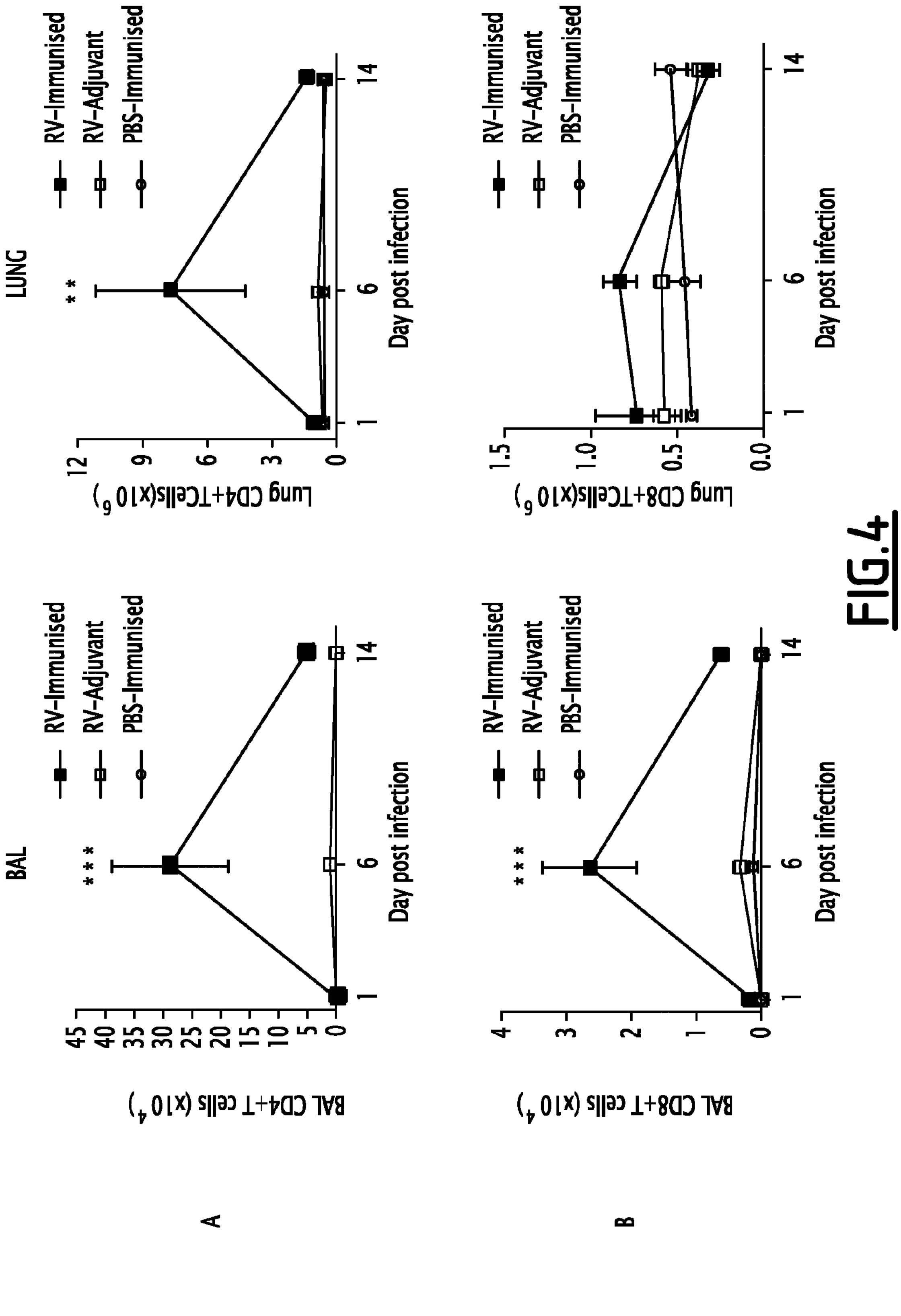

FIG. 4 is a set of graphs representing the number of CD4+ T cells (panel A) (×$10^4$) or CD8+ T cells (panel B) (×$10^6$) in BAL or lung, in mice immunized subcutaneously with HRV16 VP0 protein plus IFA/CpG adjuvant (immunized), or with IFA/CpG adjuvant only (adjuvant), and challenged intranasally with HRV1B (group RV-immunized (■) and group RV-adjuvant (□)) or mock challenged with PBS (group PBS-immunized (o)). *: $p<0.001$; : $p<0.01$.

Figure 5:
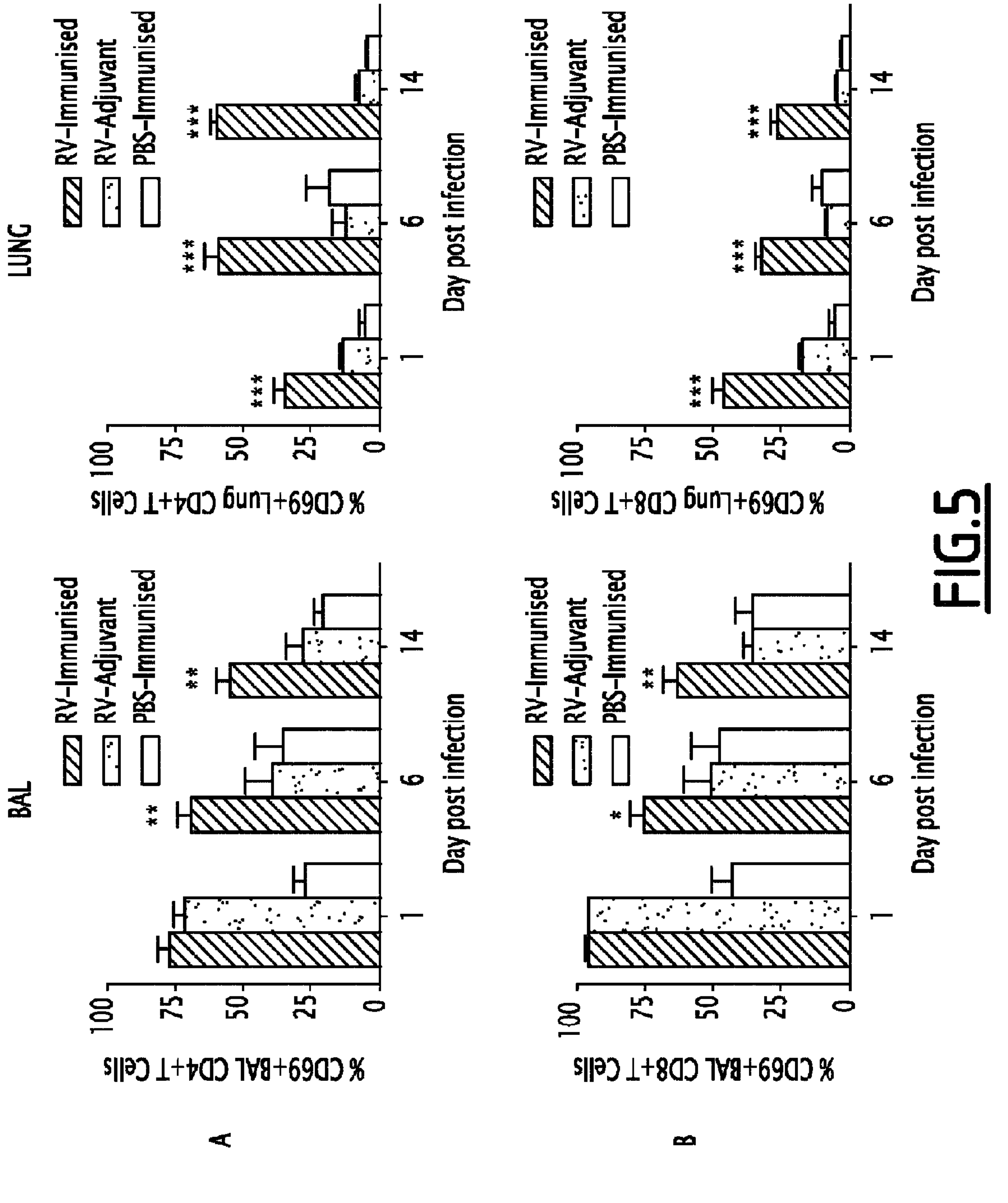

FIG. 5 is a set of histograms representing the percentage of CD4+ T cells (panel A) or CD8+ T cells (panel B) in BAL or lung expressing the early activation marker CD69, in mice immunized subcutaneously with HRV16 VP0 protein plus IFA/CpG adjuvant (immunized), or with IFA/CpG adjuvant only (adjuvant), and challenged intranasally with HRV1B (group RV-immunized and group RV-adjuvant) or mock challenged with PBS (group PBS-immunized). *: $p<0.001$; : $p<0.01$; *: $p<0.05$.

Figure 6:
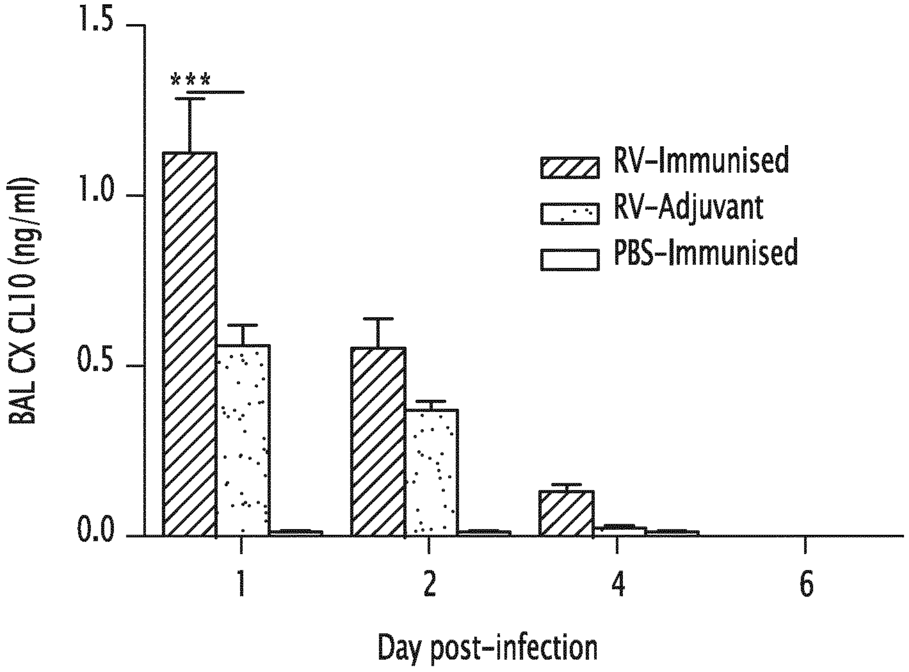

FIG. 6 is a set of histograms representing the level of CXCL10/IP-10 protein (ng/ml) in BAL, in mice immunized subcutaneously with HRV16 VP0 protein plus IFA/CpG adjuvant (immunized), or with IFA/CpG adjuvant only (adjuvant), and challenged intranasally with HRV1B (group RV-immunized and group RV-adjuvant) or mock challenged with PBS (group PBS-immunized). ***: $p<0.001$.

Figure 7:
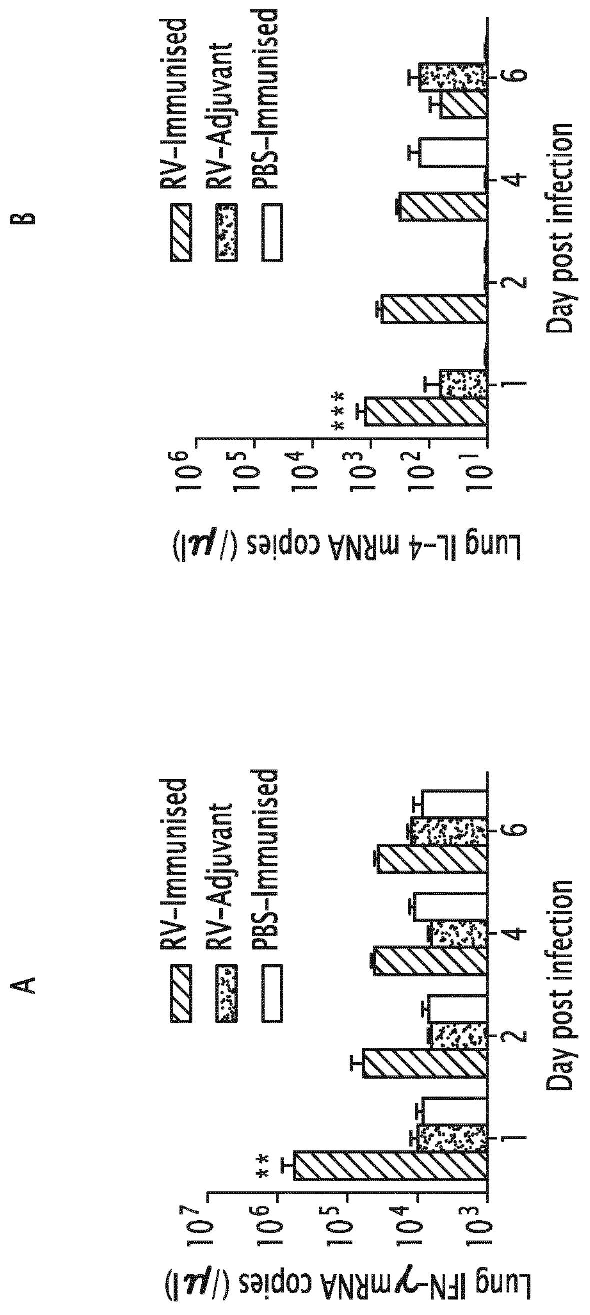

FIG. 7 is a set of histograms representing the levels (copies/μl) of lung tissue IFN-γ (panel A), and IL-4 (panel B) mRNA, measured by Taqman qPCR, in mice immunized subcutaneously with HRV16 VP0 protein plus IFA/CpG (immunized) or with IFA/CpG only (adjuvant) and challenged intranasally with HRV1B (group RV-immunized and group RV-adjuvant) or mock challenged with PBS (group PBS-immunized). *: $p<0.001$; : $p<0.01$.

Figure 8:
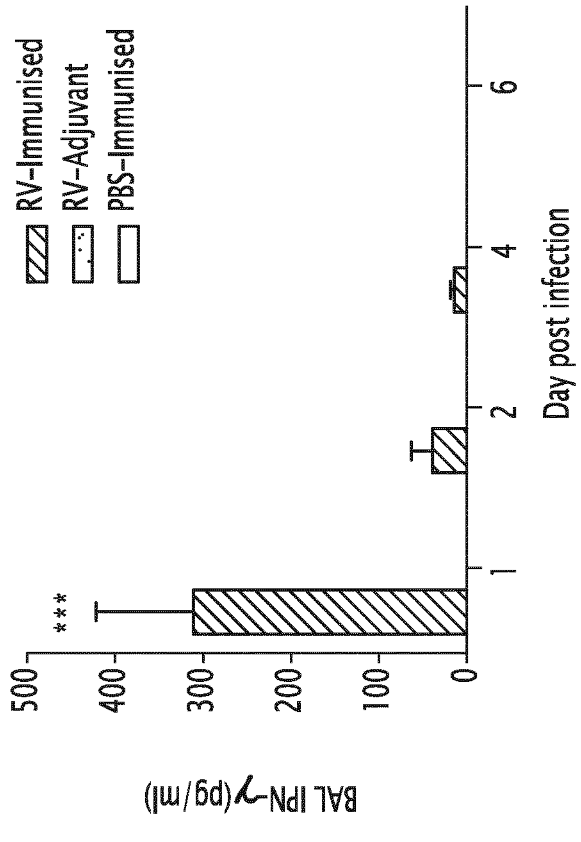

FIG. 8 is a set of histograms representing the levels (pg/ml) of BAL IFN-γ measured by ELISA, in mice immunized subcutaneously with HRV16 VP0 protein plus IFA/CpG (immunized) or with IFA/CpG only (adjuvant) and challenged intranasally with HRV1B (group RV-immunized and group RV-adjuvant) or mock challenged with PBS (group PBS-immunized). ***: $p<0.001$.

Figure 9:
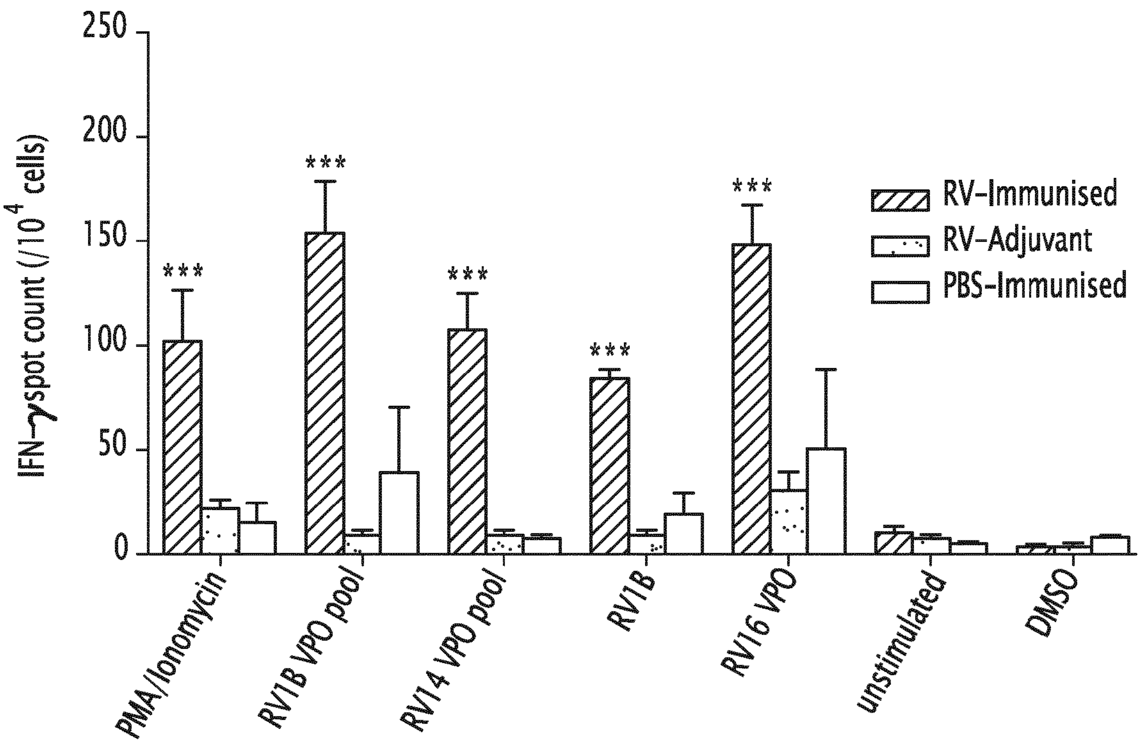

FIG. 9 is a set of histograms representing the number of IFN-γ producing cells (/$10^4$ cells), enumerated by ELISPOT, in mice immunized subcutaneously with HRV16 VP0 protein plus IFA/CpG (immunized) or with IFA/CpG only (adjuvant) and challenged intranasally with HRV1B (group RV-immunized and group RV-adjuvant) or mock challenged with PBS (group PBS-immunized), after incubation of lung cells (harvested 6 days after infection) from the 3 distinct groups of mice with the indicated stimuli. ***: $p<0.001$.

Figure 10:
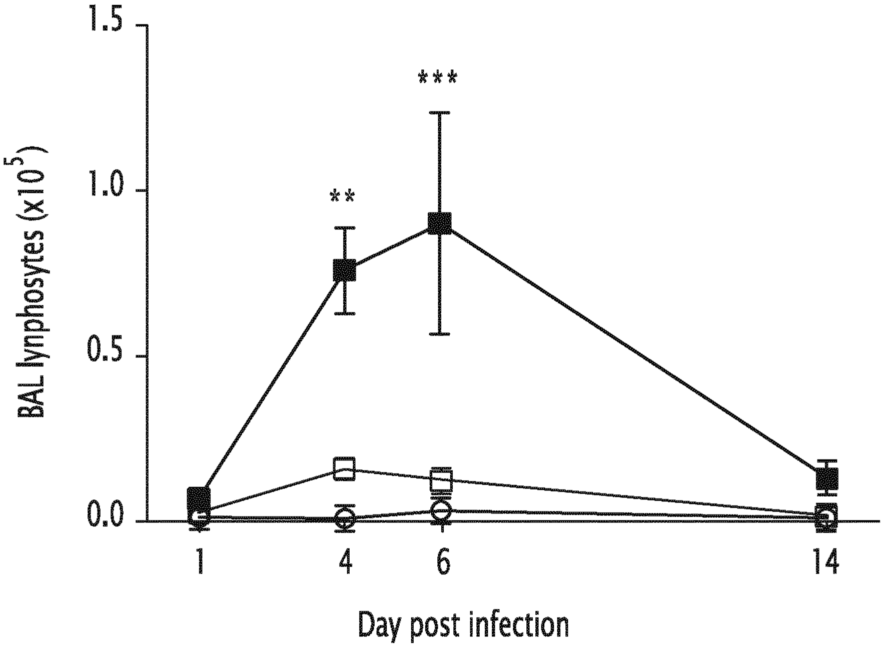

FIG. 10 is a graph representing the number of BAL lymphocytes (×$10^5$), counted by cytospin assay, in mice immunized subcutaneously with HRV16 VP0 protein plus IFA/CpG (immunized) or with IFA/CpG adjuvant only (adjuvant) and challenged intranasally with a more distant HRV, HRV29 (group RV-immunized (■) and group RV-adjuvant (□)) or mock challenged with PBS (group PBS-immunized (○)). *: $p<0.001$; : $p<0.01$.

Figure 11:
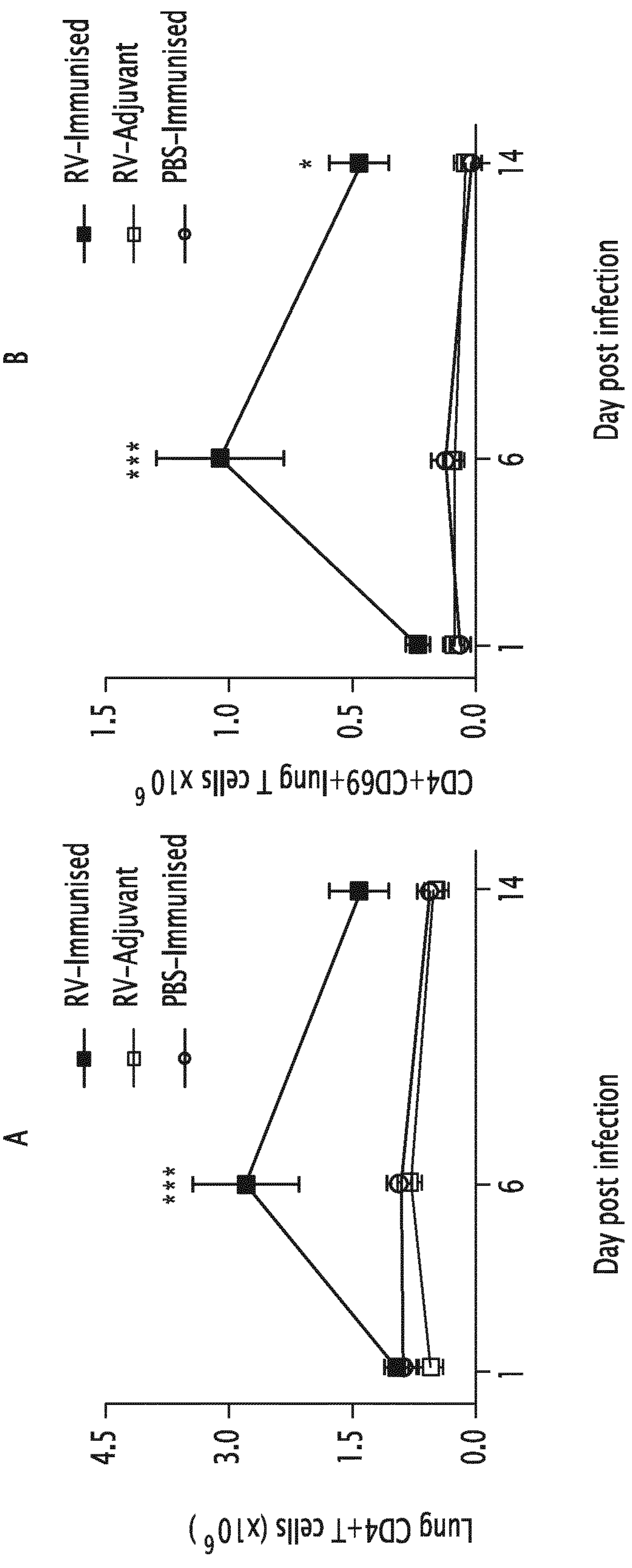

FIG. 11 is a set of graphs representing the number of total CD3+CD4+ T cells (×$10^6$) (panel A) and of CD69 expressing CD3+CD4+ T cells (×$10^6$) (panel B) in lung tissue, counted by flow cytometry, in mice immunized subcutaneously with HRV16 VP0 protein plus IFA/CpG (immunized) or with IFA/CpG adjuvant only (adjuvant) and challenged intranasally with a more distant HRV, HRV29 (group RV-immunized and group RV-adjuvant) or mock challenged with PBS (group PBS-immunized). ***: $p<0.001$; *: $p<0.05$.

Figure 12:
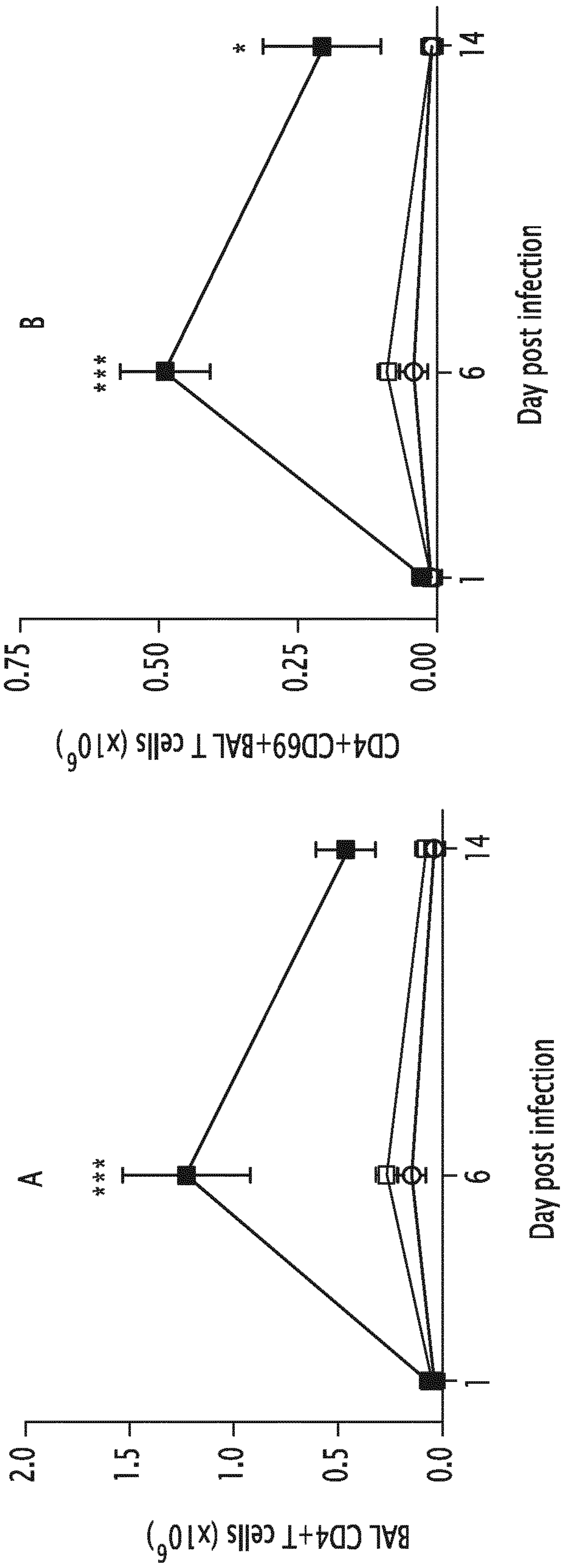

FIG. 12 is a set of graphs representing the number of total CD3+CD4+ T cells (×$10^6$) (panel A) and of CD69 expressing CD3+CD4+ T cells (×$10^5$) (panel B) in BAL, counted by flow cytometry, in mice immunized subcutaneously with HRV16 VP0 protein plus IFA/CpG (immunized) or with IFA/CpG adjuvant only (adjuvant) and challenged intranasally with a more distant HRV, HRV29 (group RV-immunized (■) and group RV-adjuvant (□)) or mock challenged with PBS (group PBS-immunized (○)). ***: $p<0.001$; *: $p<0.05$.

Figure 13:
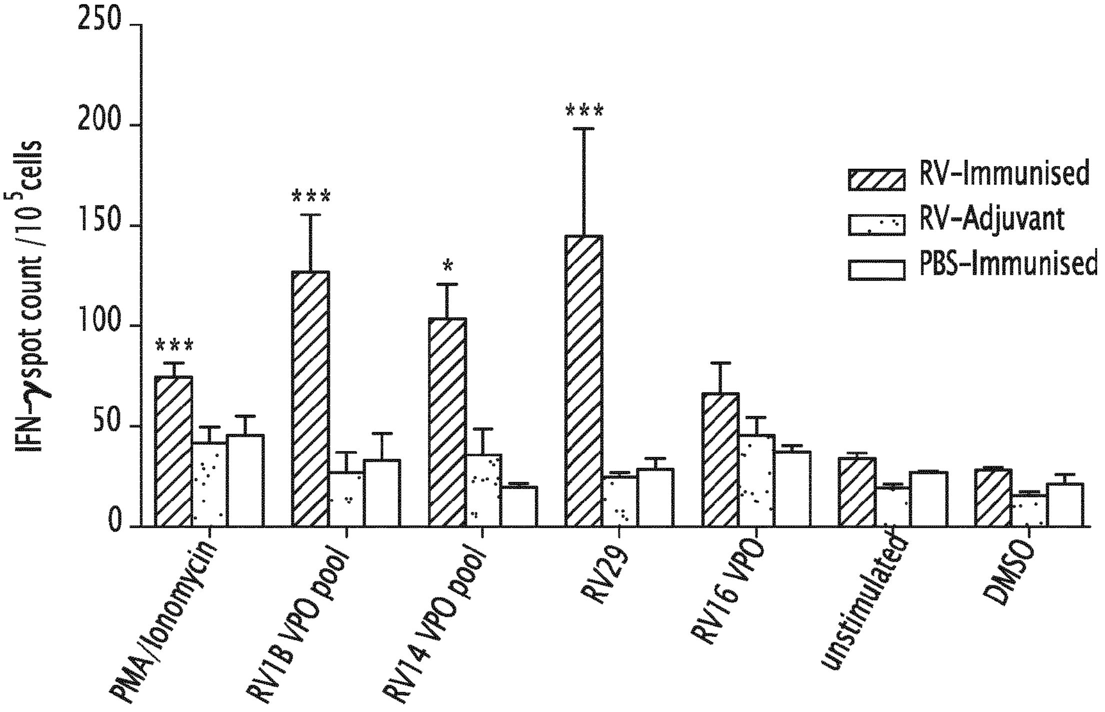

FIG. 13 is a set of histograms representing the number of IFN-γ producing cells (/$10^5$ cells), enumerated by ELISPOT, in mice immunized subcutaneously with HRV16 VP0 protein plus IFA/CpG (immunized) or with IFA/CpG adjuvant only (adjuvant) and challenged intranasally with a more distant HRV, HRV29 (group RV-immunized and group RV-adjuvant) or mock challenged with PBS (group PBS-immunized), after incubation of lung cells (harvested 6 days after infection) from the 3 distinct groups of mice with the indicated stimuli. ***: $p<0.001$; *: $p<0.05$.

Figure 14:
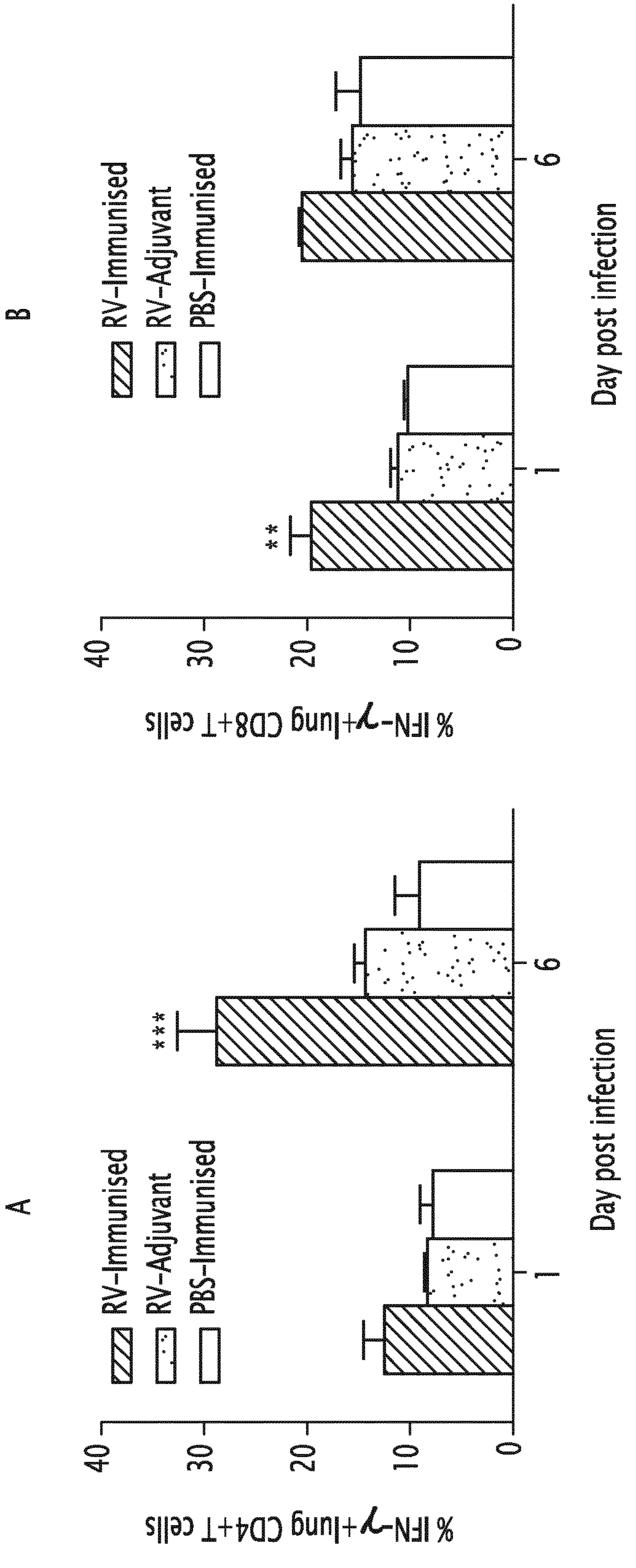

FIG. 14 is a set of histograms representing the percentage of IFN-γ producing CD4+(panel A) or CD8+(panel B) T cells, measured by flow cytometry, in lung cells, in mice immunized subcutaneously with HRV16 VP0 protein plus IFA/CpG (immunized) or with IFA/CpG adjuvant (adjuvant) only and challenged intranasally with a more distant HRV, HRV29 (group RV-immunized and group RV-adjuvant) or mock challenged with PBS (group PBS-immunized), after stimulation of lung cells with PMA and ionomycin. *: $p<0.001$; : $p<0.01$.

Figure 15:
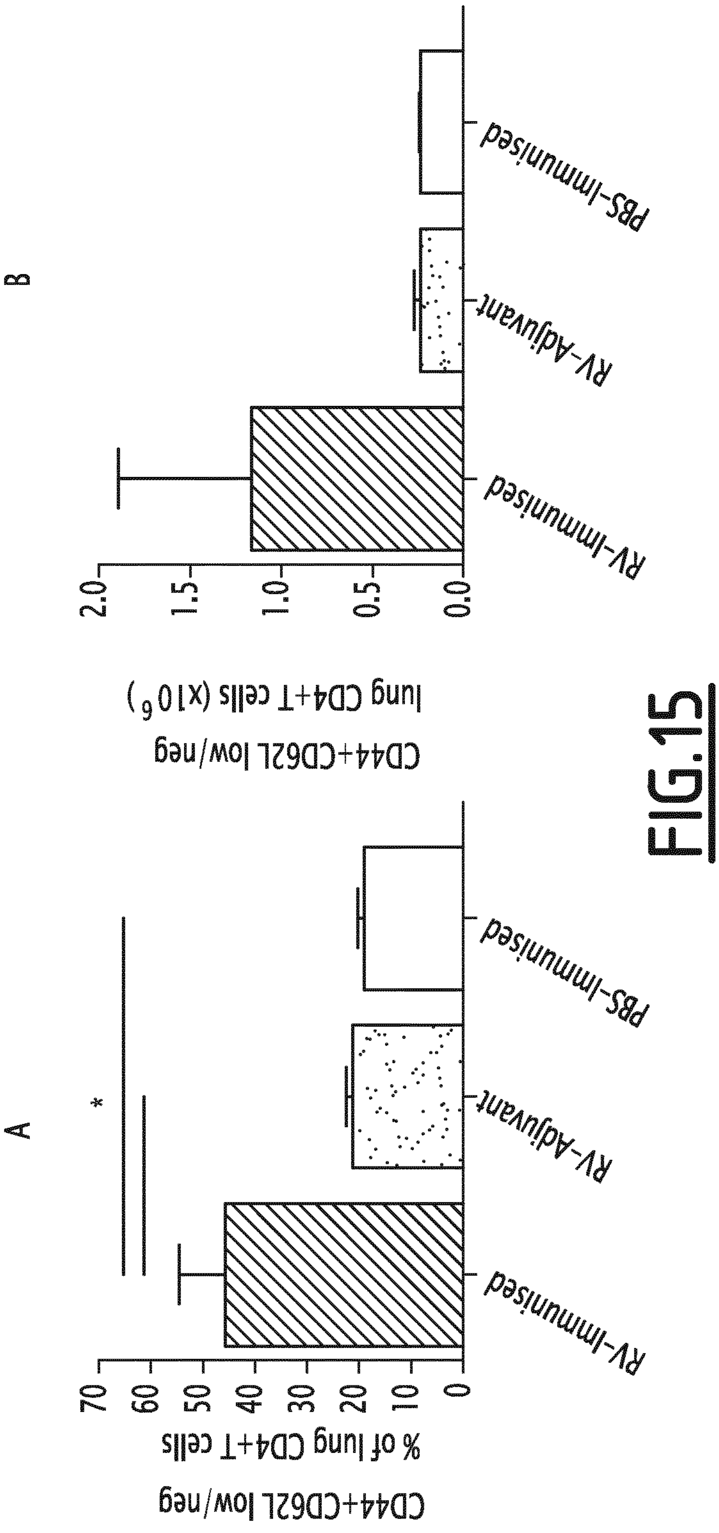

FIG. 15 is a set of histograms representing the percentage of CD44+CD62L low or CD62L− lung CD4+ T cells (panel A) or the number of CD44+CD62L low or CD62L− lung CD4+ T cells (×$10^6$) (panel B), measured by flow cytometry, on day 14 post-infection, in mice immunized subcutaneously with HRV16 VP0 protein plus IFA/CpG (immunized) or with IFA/CpG adjuvant only (adjuvant) and challenged intranasally with HRV29 (group RV-immunized and group RV-adjuvant) or mock challenged with PBS (group PBS-immunized). *: $p<0.05$.

Figure 16:
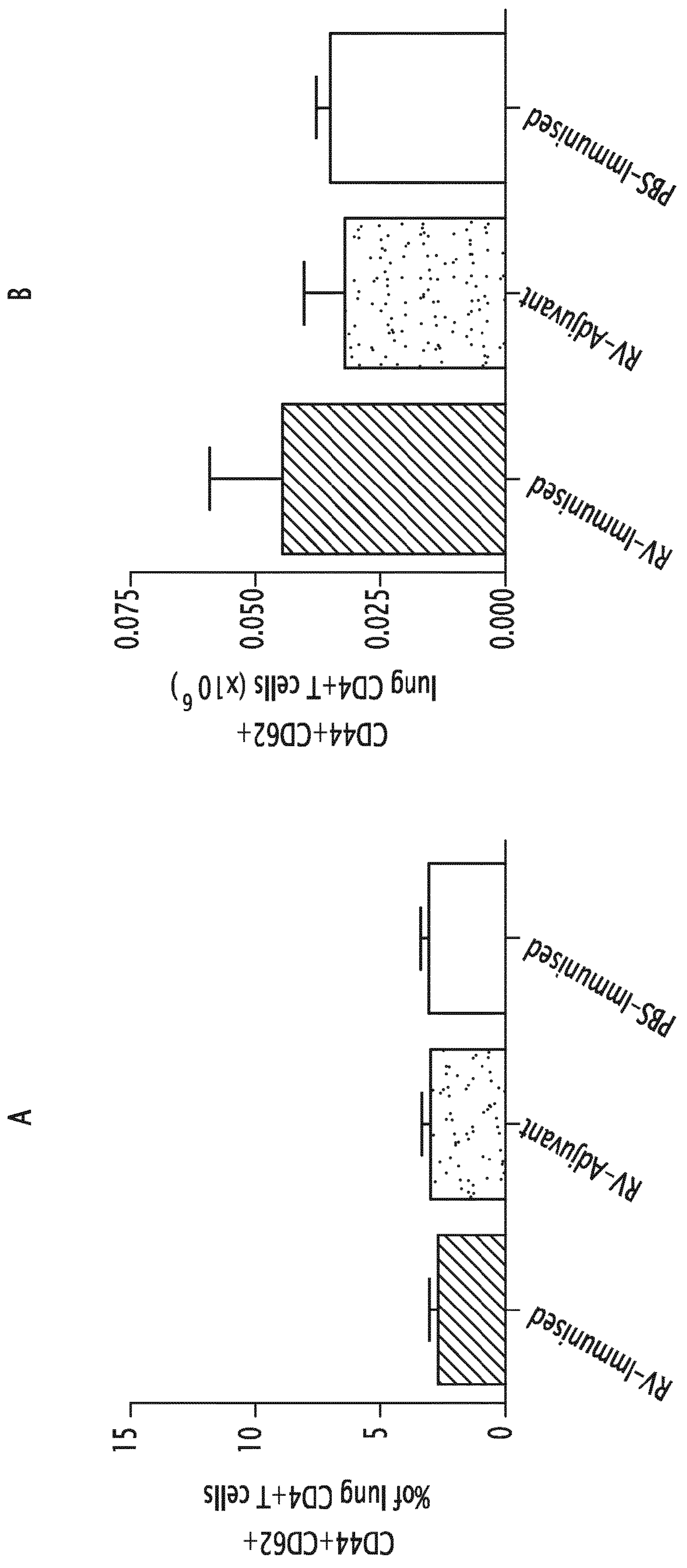

FIG. 16 is a set of histograms representing the percentage of CD44+CD62+ lung CD4+ T cells (panel A) or the number of CD44+CD62+ lung CD4+ T cells (×$10^6$) (panel B), measured by flow cytometry, on day 14 post-infection, in mice immunized subcutaneously with HRV16 VP0 protein plus IFA/CpG (immunized) or with IFA/CpG adjuvant only (adjuvant) and challenged intranasally with a more distant HRV, HRV29 (group RV-immunized RV-immunized and group RV-adjuvant) or mock challenged with PBS (group PBS-immunized). *: $p<0.05$.

Figure 17:
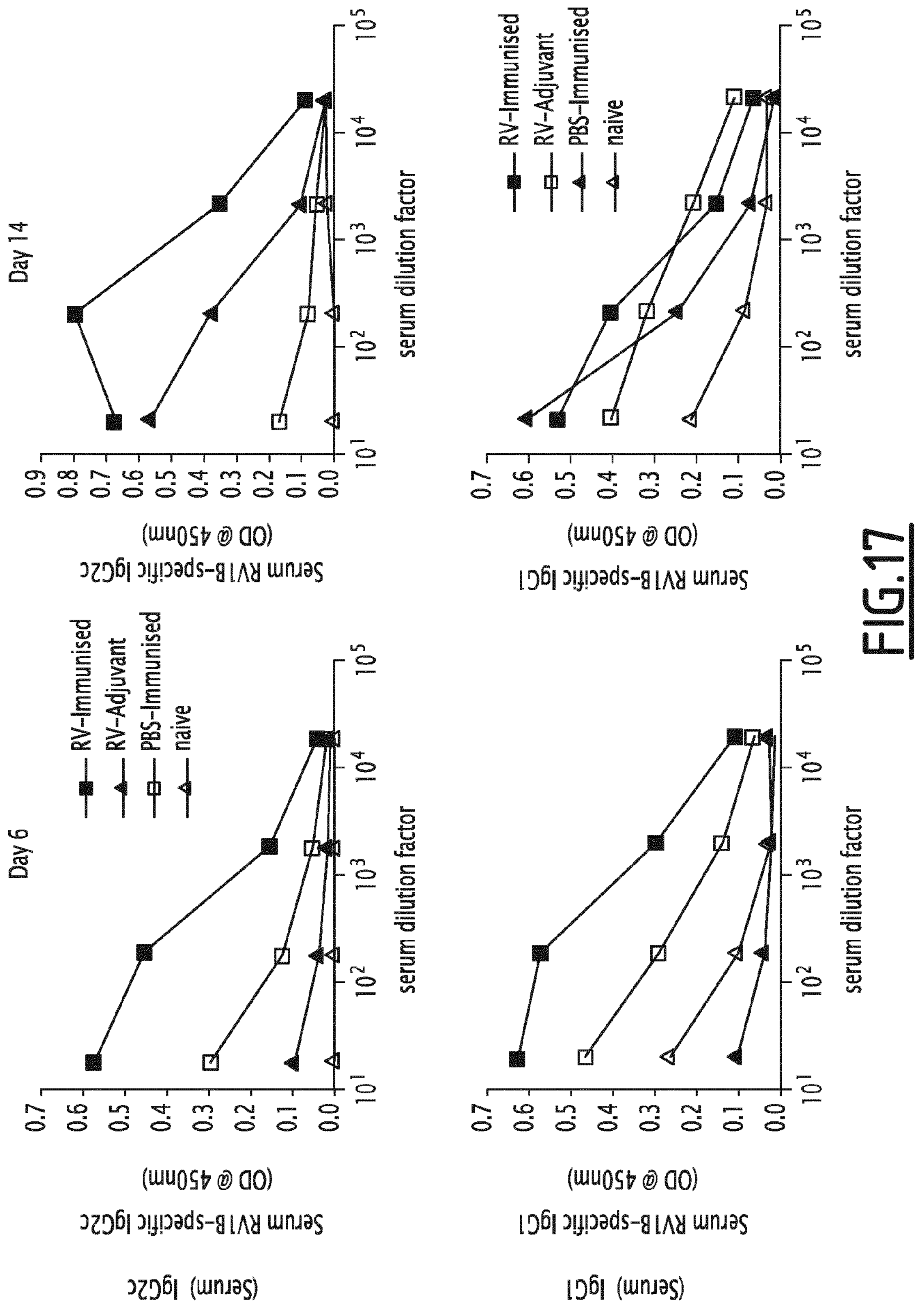

FIG. 17 is a set of graphs representing the levels of IgG2c (upper panel) and IgG1 (lower panel) that bind specifically to HRV1B in the serum of mice immunized subcutaneously either with HRV16 VP0 protein plus IFA/CpG (immunized), or with IFA/CpG adjuvant alone (adjuvant) and challenged with HRV1B (group RV-immunized and group RV-adjuvant) or mock challenged with PBS (group PBS-immunized), measured by ELISA 6 days (left panel) and 14 days (right panel) after the challenge (OD at 450 nm).

Figure 18:
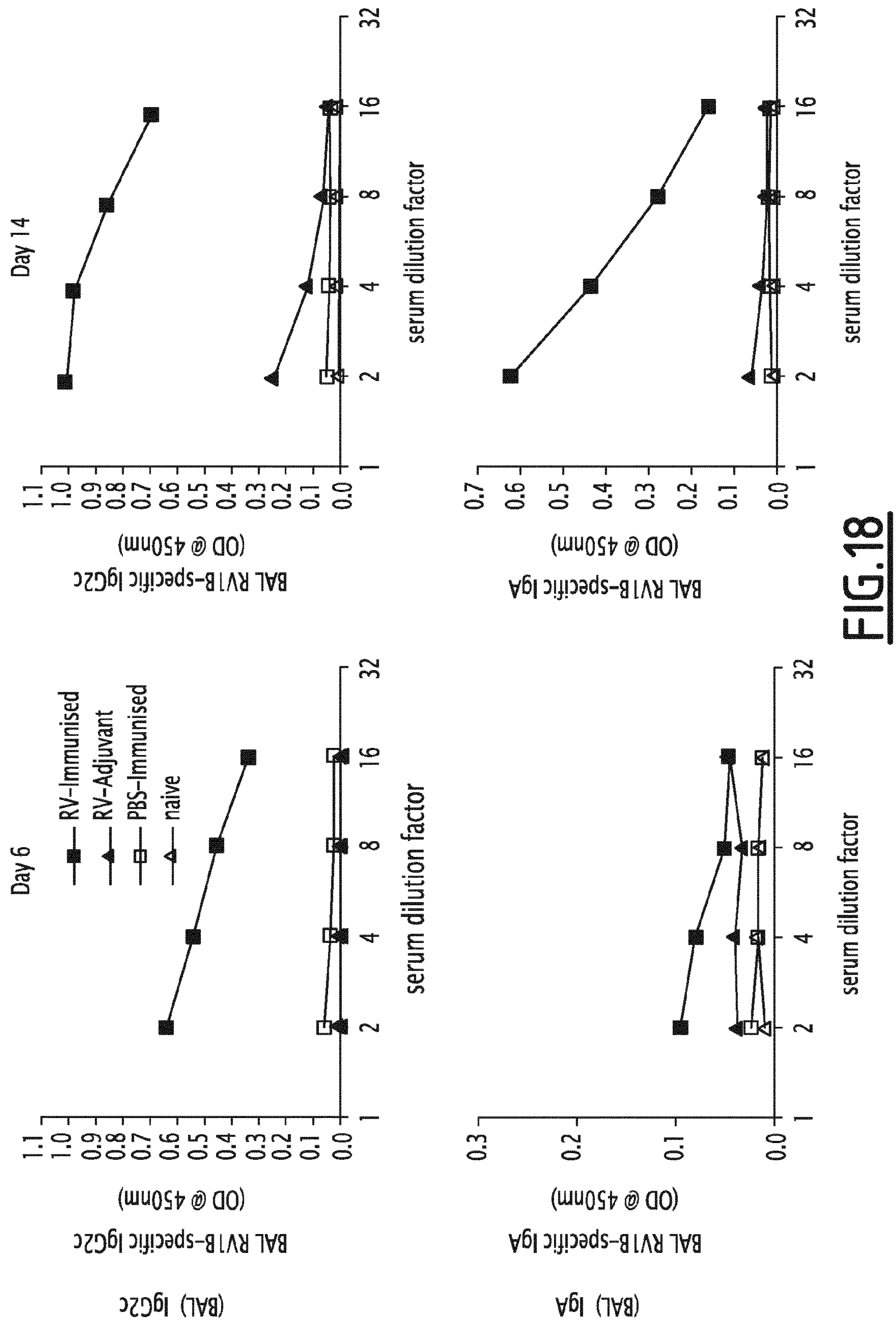

FIG. 18 is a set of graphs representing the levels of IgG2c (upper panel) and IgA (lower panel) that bind specifically to HRV1B in the BAL of mice immunized subcutaneously either with HRV16 VP0 protein plus IFA/CpG (immunized), or with IFA/CpG adjuvant alone (adjuvant) and challenged with HRV1B (group RV-immunized and group RV-adjuvant) or mock challenged with PBS (group PBS-immunized), measured by ELISA 6 days (left panel) and 14 days (right panel) after the challenge (OD at 450 nm).

Figure 19:
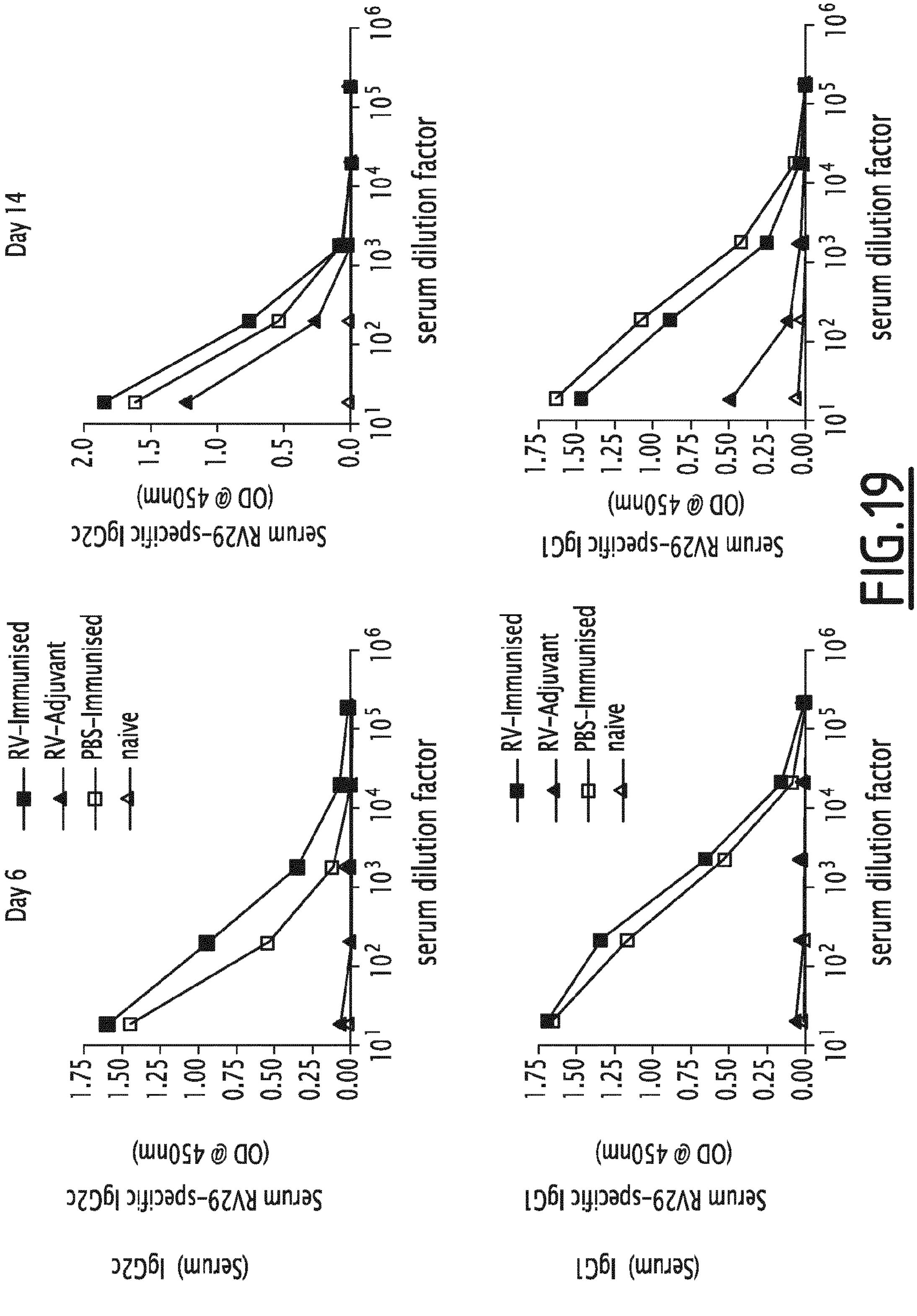

FIG. 19 is a set of graphs representing the levels of IgG2c (upper panel) and IgG1 (lower panel) that bind specifically to HRV29 in the serum of mice immunized subcutaneously either with HRV16 VP0 protein plus IFA/CpG (immunized), or with IFA/CpG adjuvant alone (adjuvant) and challenged with HRV29 (group RV-immunized and group RV-adjuvant) or mock challenged with PBS (group PBS-immunized), measured by ELISA 6 days (left panel) and 14 days (right panel) after the challenge (OD at 450 nm).

Figure 20:
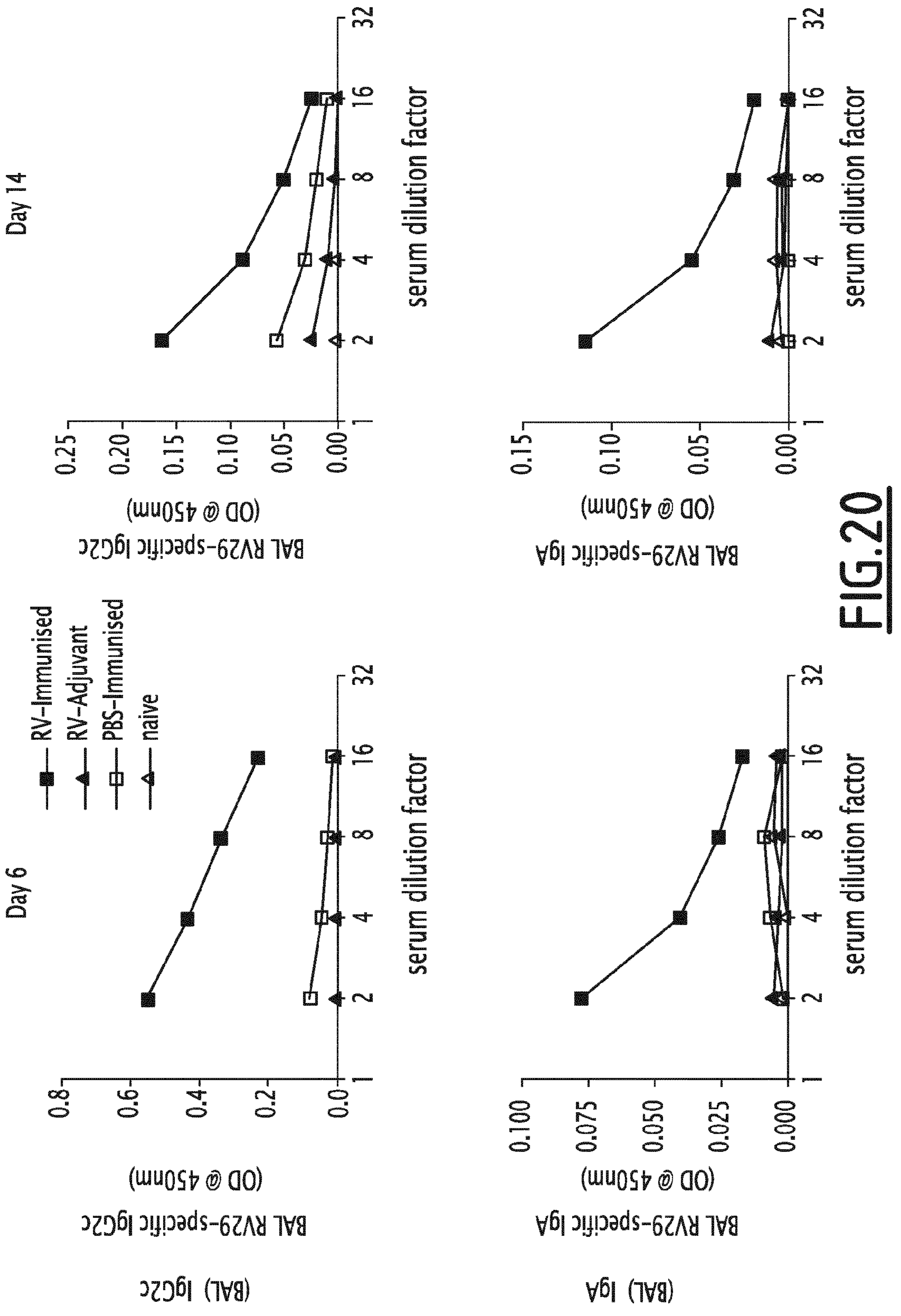

FIG. 20 is a set of graphs representing the levels of IgG2c (upper panel) and IgA (lower panel) that bind specifically to HRV29 binding in the BAL of mice immunized subcutaneously either with HRV16 VP0 protein plus IFA/CpG (immunized), or with IFA/CpG adjuvant alone (adjuvant) and challenged with HRV29 (group RV-immunized and group RV-adjuvant) or mock challenged with PBS (group PBS-immunized), measured by ELISA 6 days (left panel) and 14 days (right panel) after the challenge (OD at 450 nm).

Figure 21:
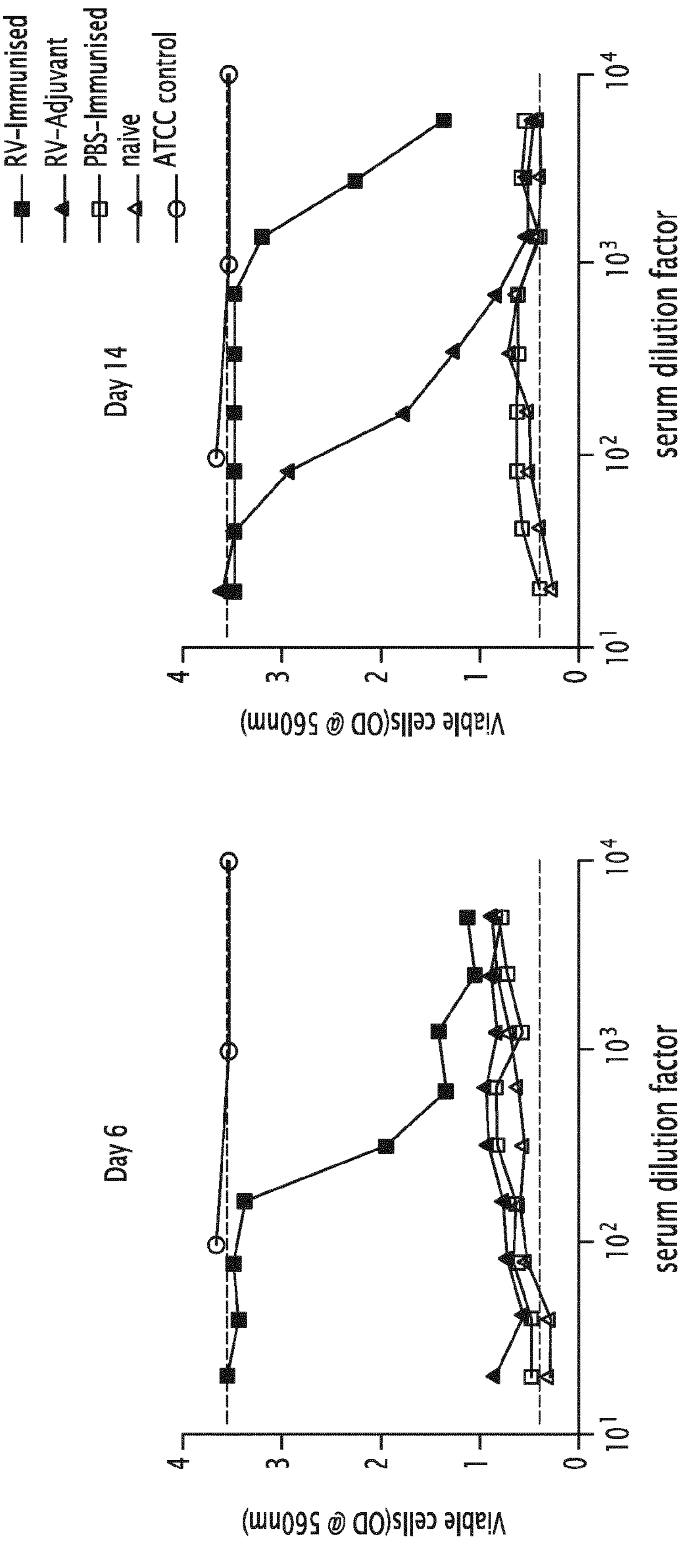

FIG. 21 is a set of graphs representing the level of neutralizing antibodies against HRV1B in pooled sera of mice immunized subcutaneously either with HRV16 VP0 protein plus IFA/CpG (immunized), or with IFA/CpG adjuvant only (adjuvant) and challenged intranasally with HRV1B (group RV-immunized and group RV-adjuvant) or mock challenged with PBS (group PBS-immunized), measured by using a crystal violet cell viability assay 6 days (left panel) and 14 days (right panel) after the challenge.

Top dotted line: cell viability of the non-infected control cells in presence of serum only.

Bottom dotted lines: cell viability of the infected control cells without serum.

ATCC control: guinea pig serum containing neutralizing antibodies against HRV1B (positive reference).

Data points represent sera pooled from 4 mice/treatment group.

Figure 22:
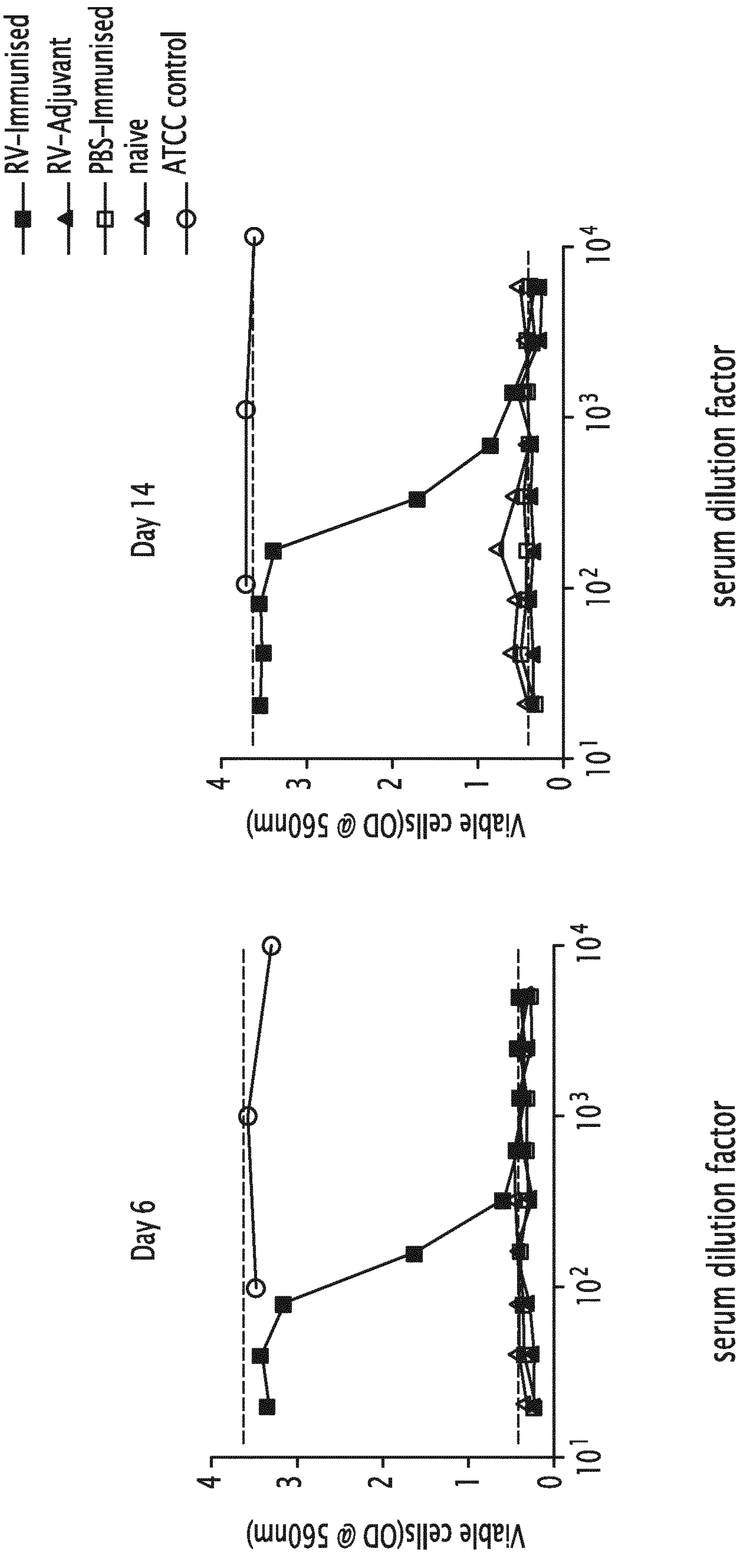

FIG. 22 is a set of graphs representing the level of neutralizing antibodies against HRV29 in pooled sera of mice immunized subcutaneously with HRV16 VP0 protein plus IFA/CpG (immunized), or with IFA/CpG adjuvant only (adjuvant) and challenged intranasally with HRV29 (group RV-immunized and group RV-adjuvant) or mock challenged with PBS (group PBS-immunized), 6 days (left panel) and 14 days (right panel) after the challenge.

Top dotted line: cell viability of the non infected control cells in presence of serum only.

Bottom dotted lines: cell viability of the infected control cells without serum.

ATCC control: guinea pig serum containing neutralizing antibodies against HRV29 (positive reference).

Data points represent sera pooled from 4 mice/treatment group.

Figure 23:
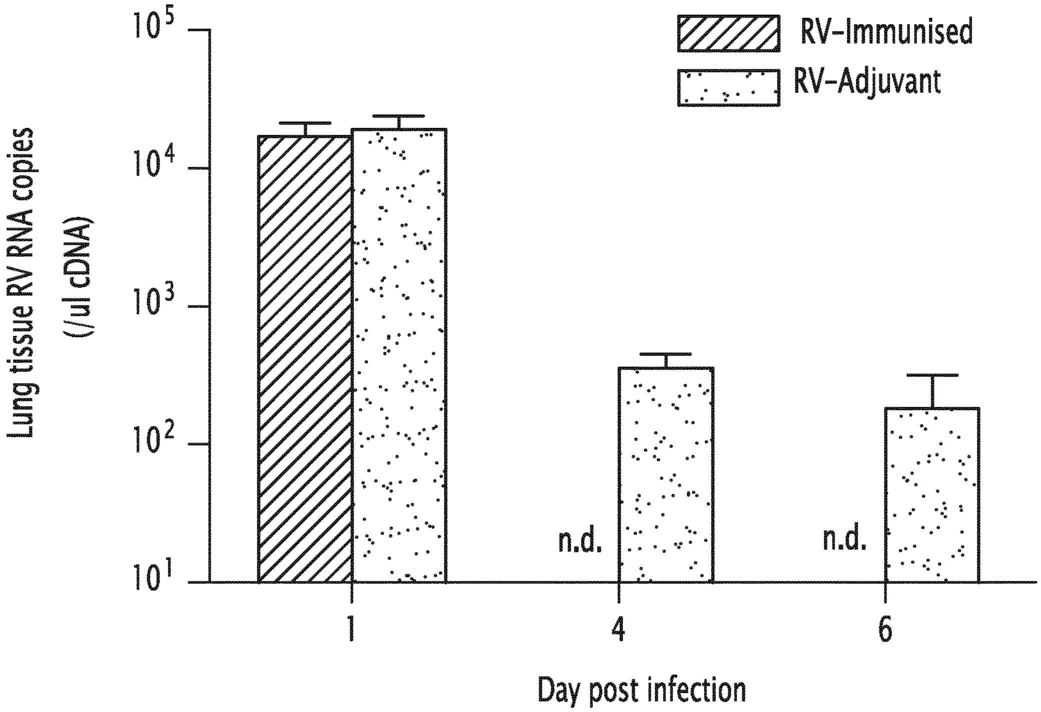

FIG. 23 is a set of histograms representing the number of HRV RNA copies in the lung tissue (/μl cDNA) of mice immunized subcutaneously either with HRV16 VP0 protein plus IFA/CpG (immunized) or with IFA/CpG adjuvant only (adjuvant) and challenged intranasally with HRV1B (group RV-immunized and group RV-adjuvant) on days 1, 4 and 6 after infection. n.d.: not detected.

Figure 24:
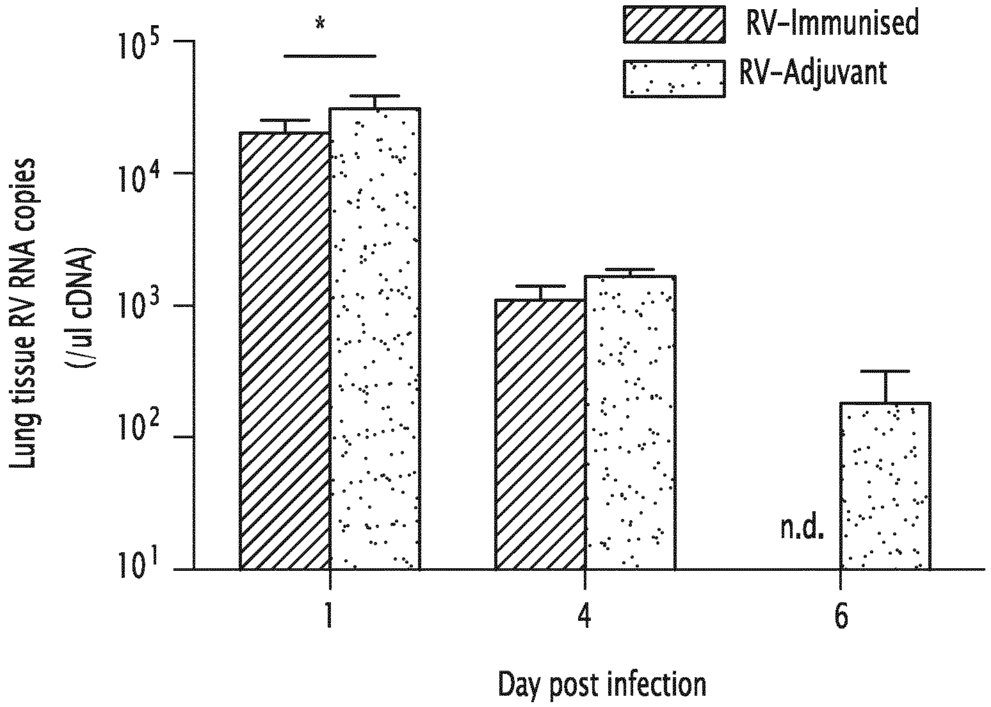

FIG. 24 is a set of histograms representing the number of HRV RNA copies in the lung tissue (/μl cDNA) of mice immunized subcutaneously either with HRV16 VP0 protein plus IFA/CpG (immunized) or with IFA/CpG adjuvant only (adjuvant) and challenged intranasally with HRV29 (group RV-immunized and group RV-adjuvant) on days 1, 4 and 6 after infection. n.d.: not detected. *: $p<0.05$.

Figure 25:
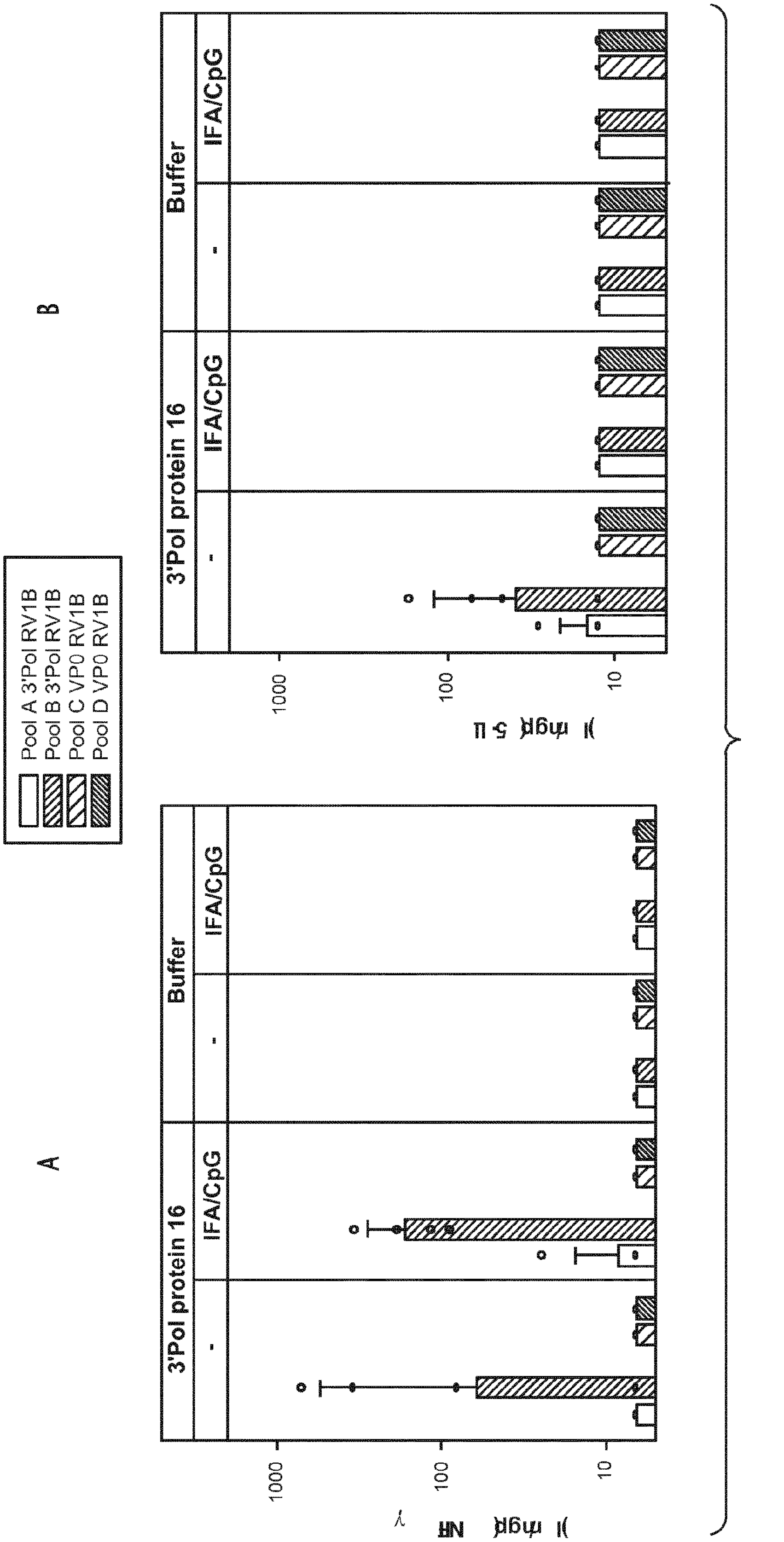

FIG. 25 is a set of histograms representing the supernatant IFN-γ (panel A) and IL-5 (panel B) level (pg/ml), measured by cytometric bead array in splenocytes of mice immunized subcutaneously with HRV16 3'Pol protein (3'Pol protein 16) or buffer, with or without IFA/CpG adjuvant (IFA/CpG), after stimulation of splenocytes with 3'Pol peptide pools from HRV1B (pool A and pool B) or VP0 peptide pools from HRV1B (pool C and pool D) the splenocytes being harvested on day 28.

Figure 26:
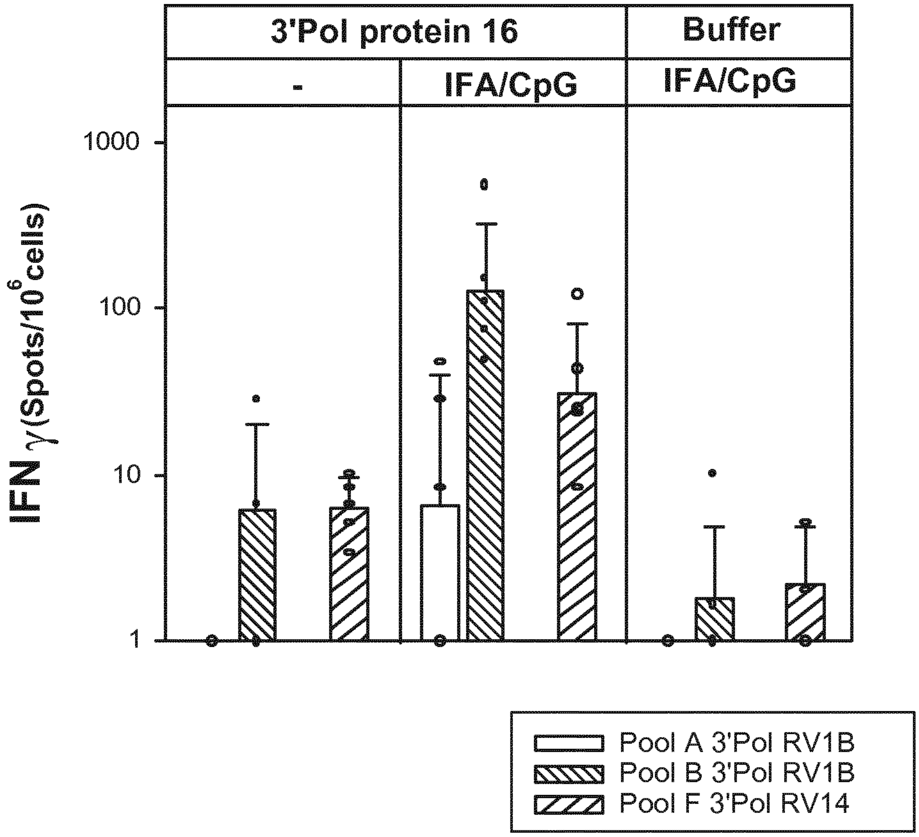

FIG. 26 is a set of histograms representing the number of IFN-γ producing cells (/$10^5$ cells), enumerated by ELISPOT, in splenocytes of mice immunized subcutaneously with HRV16 3'Pol protein (3'Pol protein 16) or buffer, with or without IFA/CpG adjuvant (IFA/CpG), after stimulation of splenocytes with 3'Pol peptide pools from HRV1B (pool A and pool B) or 3'Pol peptide pool from HRV14 (pool F), the splenocytes being harvested on day 28.

Figure 27:
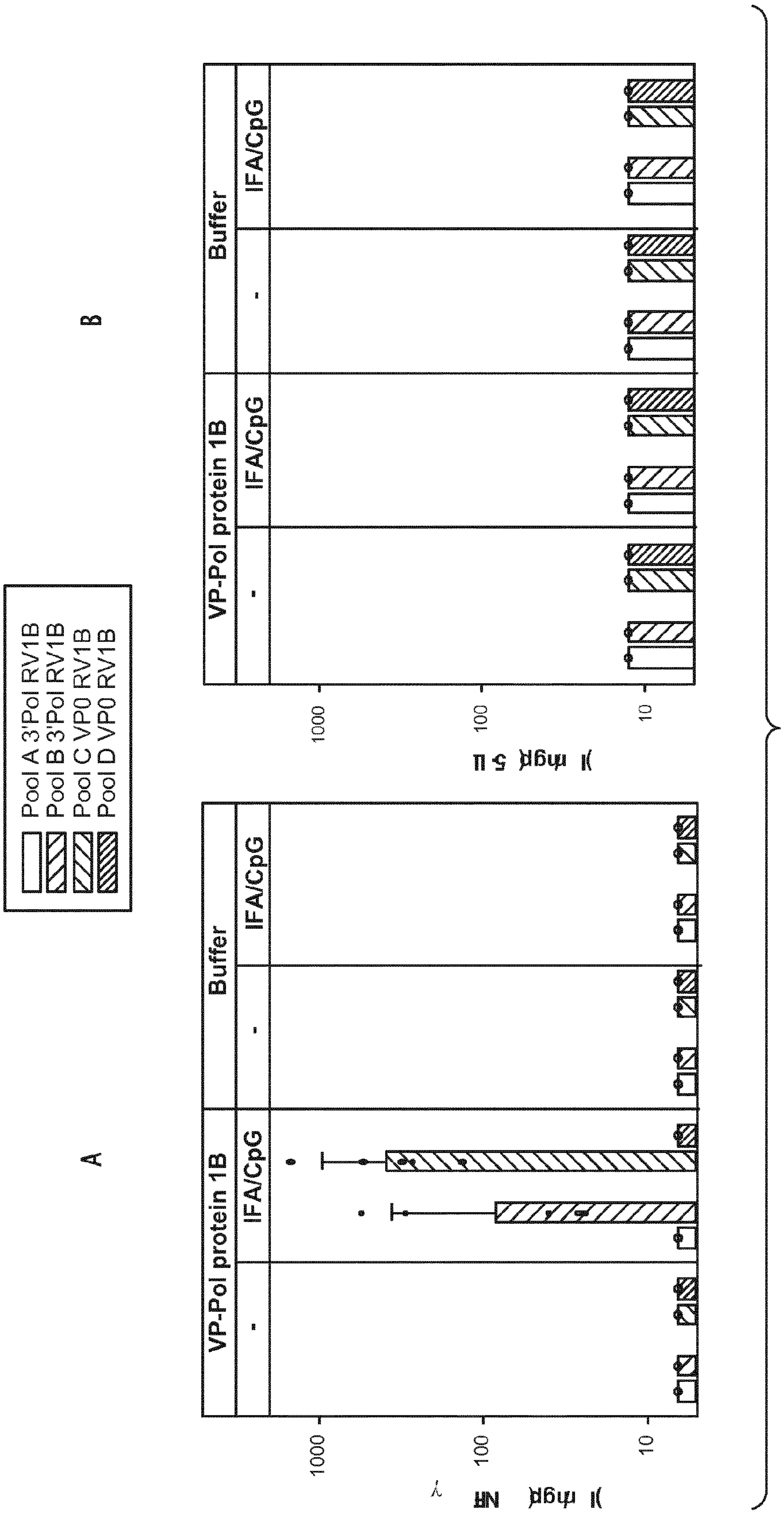

FIG. 27 is a set of histograms representing the supernatant IFN-γ (panel A) and IL-5 (panel B) level (pg/ml), measured by cytometric bead array in splenocytes of mice immunized subcutaneously with HRV1B VP-Pol (VP-Pol protein 1B) or buffer, with or without IFA/CpG adjuvant (IFA/CpG), after stimulation of splenocytes with 3'Pol peptide pools from HRV1B (pool A and pool B) or VP0 peptide pools from HRV1B (pool C and pool D) the splenocytes being harvested on day 28.

Figure 28:
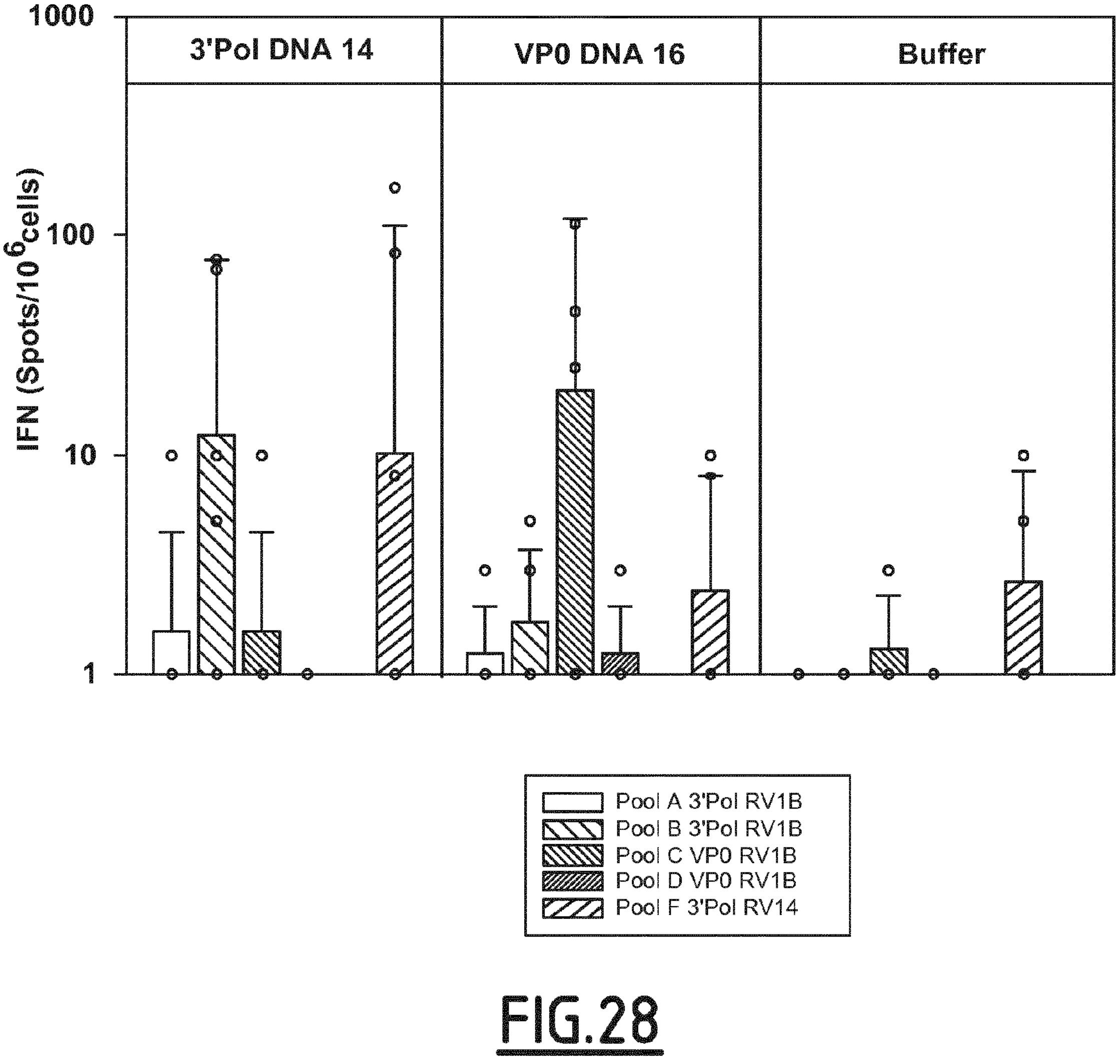

FIG. 28 is a set of histograms representing the number of IFN-γ producing cells (/$10^5$ cells), enumerated by ELISPOT in splenocytes of mice immunized subcutaneously either with HRV14 3'Pol DNA (3'Pol DNA 14), or with HRV16 VP0 DNA (VP0 DNA 16) or with buffer, after stimulation of splenocytes with 3'Pol peptide pools from HRV1B (pool A and pool B) or with 3'Pol peptide pool from HRV14 (pool F), or with VP0 peptide pools from HRV1B (pool C and pool D) the splenocytes being harvested on day 28.

Figure 29:
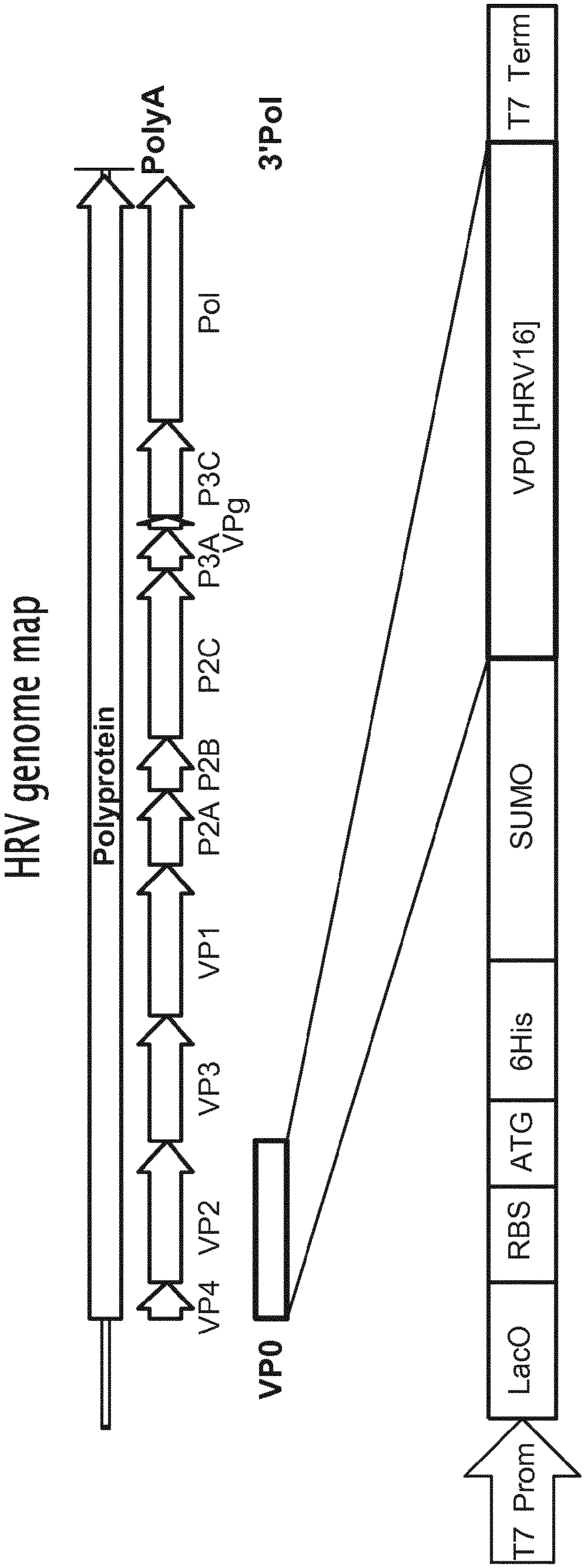

FIG. 29 is a scheme representing, at the top, the nucleic acid encoding the different domains of the HRV polyprotein, in particular the VP0 peptide, and, at the bottom, the pET-SUMO plasmid encoding the HRV16 VP0 gene.

EXAMPLES

Example 1: Identification of the Conserved Sequences

This example describes the methodology developed by the inventors to identify the conserved sequences from rhinovirus polyproteins suitable as antigens inducing a cross-reactive immune response when administered to a mammal.

Material and Methods

The design was essentially based on linear sequence conservation among HRVs. It was possible to find within each group of rhinoviruses, in particular type A rhinoviruses and type B rhinoviruses, two regions which were identified as candidate antigens: VP0 (VP4+VP2) and the C-terminus domain of the RNA polymerase. A fusion protein including the most conserved part from these two regions was also designed, attempting to minimize the number of antigens to be used in the vaccine.

A few HRV strains were selected to assess the immune response of the candidate antigens in mice. They were selected as representative of the different rhinovirus groups, as representative of the different serotypes existing in a given group of rhinoviruses, and as representative of the different receptor usage by the rhinovirus, to assess the cross-reactivity degree of the immune response.

The features of the serotypes selected are indicated in table 1 below:

TABLE 1

Features of the serotypes used

| group | Receptor: Minor | Receptor: Major |
|---|---|---|
| A | 1B, 29 | 16 |
| B | — | 14 |

All sequences were retrieved from the National Center for Biotechnology Information (NCBI) Genbank database on Aug. 23, 2007 (http://www.ncbi.nlm.nih.gov). All available complete polyprotein sequences were retrieved at that time.

All sequences were aligned using the MUSCLE algorithm (Edgar (2004) *Nucleic Acids Res.* 32:1792-7). A phylogenetic tree was elaborated using the maximum likelihood method from the Seaview application (Galtier et al. (1996) *Comput Appl Biosci.* 12:543-8). Bootstrap values were calculated to assess the robustness of the nodes. A global consensus sequence was generated from the alignments using the Jalview application (Clamp et al. (2004) *Bioinformatics* 20:426-7). The frequency of variation was calculated on each amino acid position so as to determine the conservation level all along the polyprotein. A secondary design was elaborated aiming at minimizing the size and number of antigen candidates to be used in the project. The available 3D structures of structural proteins (VP) and polymerase 3D (P3D) were used to define the most appropriate fusion location between VP and P3D, taking into account both the conservation level and the structural conformation of the two subunits.

Sequence alignments were launched for all available complete polyproteins from HRV-A, HRV-B and HRV-A and -B together.

Global consensus sequences were extracted from each alignment and frequency of occurrence for each major amino acid was calculated. The results were presented as a linear sequence of the global consensus under which the frequency of each position was indicated and coloured according to its frequency. That representation provided an easy way to visualize the most conserved regions along consensus polyproteins.

The goal of the present study was to identify the most conserved domains among human rhinoviruses to select subregions to be subcloned for recombinant expression. As only a T-cell cross-reactive response is targeted, any part of the polyprotein can be considered equally.

As T-cell peptides must have at least 8 amino acids (aa) in length (for CD8 responses), selected regions should present identity stretches of at least the same length. CD4 peptides are in the 15 aa long range.

Starting first from the global sequence alignment including both type A and type B viruses, the present inventors demonstrated that variable and conserved domains were almost the same in the two virus types. Accordingly, the selected regions were located in the same regions in both virus types.

Results

Type A Conserved Amino Acid Sequences

HRV-A VPo—

The first selected region was the N-terminus part of the “large” polyprotein. The amino acids [1-191] and amino acids [243-297] in the amino acid sequence of the “large” polyprotein appeared especially well conserved among type A rhinoviruses. As the polyprotein VP0 (including VP4 and VP2), consisting of the amino acid sequence [1-339], includes these two domains, the domain encoding VP0 was selected as a first antigen candidate.

HRV-A 3'pol—

The C-terminus end of the “large” polyprotein also showed large portions of very well conserved sequences among type A rhinoviruses. The last 363 amino acids were retained as a second recombinant antigen candidate. They consisted of the C-terminus part of the RNA polymerase of the virus.

HRV-A VP-Pol Fusion Antigen—

Aiming at reducing the number of antigens, a second design was elaborated as a fusion between VP0 and 3'pol candidates. Both parts were shortened to maintain a global antigen size easy to express, and the junction between the two parts was designed so as to preserve independent folding of the two regions to be fused.

The VP4 protein was entirely included in the new design. The sequence of VP2 was shortened by its C-terminus part. Considering the 3D structure, the selected part of VP2 corresponds to a domain relatively independent from the rest of the VPs, avoiding so major folding constraints that could potentially impair with the recombinant expression and/or folding. The stop in a flexible loop was also selected to facilitate the fusion with the 3'pol domain to be added in C-terminus of the VP sequence.

The designed VP4-2 sequence represented the first N-terminal 135 amino acids of the VP0 polyprotein. Exactly the same region could be selected for type B HRVs.

Considering the 3'pol domain, the same approach was used. Available 3D structures were identified from HRV-1B (type A) and HRV-14 (type B). As for VPs, the 3D structures of the 3'pol domain of HRV-1B and HRV-14 were similar, and led to the design of peptides corresponding to the same region in the RNA polymerase of both serotypes.

From the initial design, the selected C-terminus part of 3'pol was truncated from its N-terminus. Looking at both 3D structure and conservation level, the last 105 C-terminal amino acids were selected.

HRV-A (1B, 16, 29) Sequences Used for Further Cloning and Expression—

Practically, sequences corresponding to each design were retrieved from target strains. Additional sequences were added to build the proper open reading frame including all elements required in the selected recombinant expression system (N-terminus methionine, stop codon when needed, tag and SUMO).

The sequences expressed are listed in Table 2 below. Actual cloned sequences were artificially synthesized introducing several modifications in nucleotide sequences such as codon use optimization for recombinant expression in *Escherichia coli.*

TABLE 2

Sequences expressed

| Strain | Name | SEQ ID |
|---|---|---|
| HRV-1B | VPo | 17 |
| HRV-1B | 3'pol | 18 |
| HRV-1B | VP-pol | 19 |
| HRV-16 | VPo | 6 |
| HRV-16 | 3'pol | 13 |
| HRV-16 | VP-pol | 11 |
| HRV-29 | VPo | 20 |
| HRV-29 | 3'pol | 21 |
| HRV-29 | VP-pol | 22 |

Type B Conserved Amino Acid Sequences

HRV-B VPo—

As observed for type A HRV alignment, the N-terminus region of the “large” polyprotein of HRV-B is also very well conserved. Following the same strategy, the complete VP0 sequence was selected as the first HRV-B antigen candidate.

HRV-B 3'pol—

As observed for type A HRVs, the C-terminus end of the “large” polyprotein showed large portions of very well conserved sequences. The last 365 amino acids were retained as a second recombinant antigen candidate. They consist of the C-terminus part of the RNA polymerase of the virus.

HRV-B VP-Pol Fusion Antigen—

Similarly to the design of the HRV-A VP-Pol fusion antigen, both parts of VP0 and 3'pol candidates were shortened to maintain a global antigen size easy to express, and the junction between the two parts was designed so as to preserve independent folding of the two regions to be fused.

The designed VP4-2 sequence represented the first N-terminal 135 amino acids of the VP0 polyprotein and the last C-terminal 105 amino acids of 3'pol were selected.

HRV-B (14) Sequences Used for Further Cloning and Expression—

The B strain selected in the present study was HRV-14.

The sequences to be expressed are listed in Table 3 below.

TABLE 3

| Sequences expressed | | |
|---|---|---|
| Strain | Name | SEQ ID |
| HRV-14 | VPo | 8 |
| HRV-14 | 3'pol | 14 |
| HRV-14 | VP-pol | 12 |

Example 2: Expression and Purification of the Conserved Antigens

This example describes the protocol used to express and purify the antigens designed in Example 1.

Cloning and Expression

The same cloning strategy has been applied for all recombinant proteins. Briefly, each respective nucleotide sequence was optimized for *E. coli* expression and synthesized (Geneart). Several antigens were also engineered to be expressed as a recombinant fused peptide to the SUMO tag: the synthetic gene cloned in frame with the SUMO sequence in the T/A cloning site of the pET-SUMO vector was then expressed using the pET-SUMO expression system form Invitrogen.

As an example, VP0 peptide of HRV16 was expressed by BL21λDE3 *E. coli* transfected by the pET-SUMO plasmid encoding the HRV-16 VP0 gene. Optimal growth condition for the recombinant protein expression was obtained at 25° C. under agitation (220 rpm) with the Overnight Express Autoinduction System 1 from Novagen (FIG. 29).

For DNA immunization, each respective nucleotide sequence as described in tables 2 and 3 were cloned into the pcDNA3.1 plasmid commercialized by Invitrogen. Protein expression was checked by transfection in CHO cells and analyzed by western blot using an anti-histidin antibody before injection in mice.

Purification

Despite the presence of the SUMO tag located at the N-terminus, the different recombinant peptides were still expressed into the insoluble fractions as inclusion bodies. Their purification was performed according the manufacturer recommendations (Invitrogen) adapted for insoluble peptides.

Briefly, SUMO-fused peptides extracted with Tris/NaCl buffer containing 8M urea were loaded onto Nickel sepharose column (Pharmacia) for Immobilized Metal Affinity chromatography (IMAC). Purification was performed by applying an imidazole gradient to the column. Recombinant peptides eluted into the 250 mM of imidazole fractions were further dialysed against a digestion buffer (Tris 20 mM, NaCl 150 mM pH 8.0 containing 2M Urea) in order to cleave the SUMO moiety by the SUMO ULP-1 protease.

The HRV 16 VP0 obtained after digestion by the SUMO ULP-1 protease was further applied onto a second Nickel sepharose column in order to remove the SUMO moiety, the non-cleaved protein and the protease containing His tag.

The cleaved HRV 16 VP0 obtained after the second purification step was further dialysed against Tris/NaCl buffer (Tris 20 mM, NaCl 150 mM, Arginine 0.5 M, pH 8.0) compatible with animal experimentation.

The purity degree of the isolated peptide measured by monitoring on SDS-PAGE was about 90%

Example 3: Immunogenicity of the Designed Antigens in Mice

This example demonstrates the immunogenicity of the peptides and fusion peptides of the invention in mice.

Materials and Methods

Immunization 7-week-old C57BL/6 mice were immunized by subcutaneous (SC) route in the scapular belt on Day 0 and 21.

Each mouse was given 10 μg of HRV16 VP0 protein (VP16) in a total volume of 200 μl in presence or absence of IFA/CpG adjuvant (10 μg CpG 1826 (MWG Eurofins, Ebersberg, Germany)+100 μL Incomplete Freund's Adjuvant (IFA) per dose injected).

Protein Buffer (Tris 20 mM, NaCl 150 mM, Arginine 0.5 M pH 8.0) in presence or absence of IFA/CpG adjuvant was used as a negative control and administered in control groups of mice according to the same procedure.

Sampling Processing

Blood and spleens were collected on day 49 in Vacutainer Vials (BD Vacutainer SST II Nus plastic serum tube BD, Le Pont-De-Claix, France), kept overnight at 4° C. and centrifuged 20 min at 1660 g in order to separate serum from cells. Sera were conserved at −20° C.

Spleens were collected under sterile conditions after sacrifice.

Western Blots

Anti-HRV16 VP0 IgG responses were analyzed by Western Blot from pooled sera.

HRV16 VP0 protein was mixed with a denaturation buffer containing NUPAGE LDS Sample Buffer at 2× (Invitrogen, Carlsbad, Calif.), 100 mM of Dithiothreitol (DTT) (SIGMA, St. Louis, Mo.) and water; and kept for 20 min at 95° C.

2 μg of protein were loaded on a polyacrylamide SDS gel (NuPAGE Novex 4-12% Bis-Tris Gel 1.0 mm, 12 well (Invitrogen), in NuPAGE MES SDS Running Buffer (Invitrogen)). Migration was performed for 30 min at 200 V. Molecular weight SeeBluePlus2 Pre-Stained Standard (Invitrogen) was used as a marker.

Protein was transferred onto a nitrocellulose membrane (Bio-Rad Laboratories, Hercules, Calif.) by semi-dry blotting in a NuPAGE transfer buffer (Invitrogen) for 1 h at 65 mA and constant voltage. The non-specific sites were blocked with phosphate-buffer saline (PBS, Eurobio, Courtaboeuf, France), 0.05% Tween 20 (VWR Prolabo Fontenay-sous-Bois, France) and 5% of powdered skim milk (DIFCO, Becton Dickinson, Sparks, USA), 1 h at room temperature under gentle agitation. The nitrocellulose membrane was incubated with pooled mouse sera diluted 1:200 in PBS-Tween 0.05% for 1 h under agitation. Horseradish peroxidase (HRP)-conjugated goat anti-mouse IgG (Jackson ImmunoResearch, Suffolk, UK) diluted 1:2000 in PBS-Tween 0.05% were added for 1 h under agitation.

Membranes were washed 3 times (5 min) with PBS Tween 0.05% between each incubation.

Colorimetric revelation was performed with HRP substrate, 4-chloro-1-naphthol Opti-4CN (Bio-Rad) and acquired on GBox (Syngene).

ELISA

Anti-HRV16 VP0 IgG1 and IgG2a (or IgG2c responses in C57Bl/6 mice) responses were measured by ELISA.

Dynex 96-well microplates (Dynex Technologies, Berlin, Germany) were coated with 100 ng per well of VP16 in 0.05 M sodium carbonate buffer, pH 9.6 (SIGMA, Saint Louis, Mo.), overnight at 4° C. Non-specific sites were blocked with 150 μl per well of PBS pH 7.1, 0.05% Tween 20, 1% of powdered skim milk (DIFCO) 1 h at 37° C.

Sera diluted in PBS-Tween 0.05%, milk 1%, were dispensed at 1:100 or 1:1000 in the first well of plates followed by two fold dilutions in the following wells.

After 1 h 30 of incubation at 37° C., plates were washed 3 times with PBS-Tween 0.05%.

HRV16 VP0-specific IgG1 and IgG2a were detected using Goat anti-Mouse IgG1-HRP, Human absorbed (Southern Biotech, Birmingham, Ala.) and Goat anti-Mouse IgG2a- or 2c-HRP, Human absorbed, (Southern Biotech, Birmingham, Ala.) diluted 1:4000 in PBS-Tween 0.05%, milk 1%, 1 h 30 at 37° C.

Nates were washed and incubated with TetraMethylBenzidine TMB (Tebu-bio laboratories, Le Perray-en-Yvelines, France) 30 min in the dark at room temperature. Colorimetric reaction was stopped with 100 μl per well of HCl 1M (VWR Prolabo Fontenay-sous-Bois, France) and measured at 450 and 650 nm on a plate reader Versamax (Molecular Devices).

Blank values (mean negative controls values) were subtracted from the raw data (optical density (OD) 450-650 nm).

Titers were calculated with tendency function and expressed in arbitrary ELISA units (EU), which correspond to the inverse of the serum dilution giving an OD of 1.0.

Peptide Pools Used for Splenocytes Stimulation

Splenocytes were stimulated by peptide pools to monitor cytokines secretion by CBA or ELISPOTs assays. The peptides correspond to the identified cross-reactive domains of HRV1B and HRV14.

Peptides were synthesized and purified by JPT (Berlin, Germany). The peptides were 15mers overlapping on 11 amino acids. Each peptide was solubilized in DMSO (PIERCE, Thermo Fisher Scientific, Rockford, USA). The DMSO concentration had to be adjusted in such a way the final percentage of DMSO in cell cultures was always less than 1% in order to avoid DMSO toxicity on cells. Pools of about 40 peptides were constituted and kept frozen at −80° C. until use.

The content of the respective peptide pools are presented below:

Pool C was composed of 15mers peptides (peptides 1 to 40), overlapping on 11 amino acids, covering amino acids 1 to 171 of the HRV1B VP0 protein of sequence SEQ ID NO: 17, at a concentration of 50 μg/ml/peptide.

Pool D was composed of 15mers peptides (peptides 41 to 81), overlapping on 11 amino acids, covering amino acids 172 to 332 of the HRV1B VP0 protein of sequence SEQ ID NO: 17, at a concentration of 48.8 μg/ml/peptide.

Pool A was composed of 15mers peptides (peptides 1 to 44), overlapping on 11 amino acids, covering amino acids 1 to 187 of the HRV1B 3'pol peptide of sequence SEQ ID NO: 18, at a concentration of 45.5 μg/ml/peptide.

Pool B was composed of 15mers peptides (peptides 45 to 89), overlapping on 11 amino acids, covering amino acids 188 to 365 of the HRV1B 3'pol peptide of sequence SEQ ID NO: 18, at a concentration of 44.4 μg/ml/peptide.

Pool E was composed of 15mers peptides (peptides 41 to 80), overlapping on 11 amino acids, covering amino acids 1 to 171 of the HRV14 VP0 protein of sequence SEQ ID NO: 8, at a concentration of 500 μg/ml/peptide.

Pool F was composed of 15mers peptides (peptides 123 to 164), overlapping on 11 amino acids, covering amino acids 186 to 363 of the HRV14 3'pol peptide of sequence SEQ ID NO: 14, at a concentration of 476.2 μg/ml/peptide.

Measurement of Cytokines by Cytometric Bead Array (CBA)

Spleens were homogenized manually with a syringe plunger through a cell strainer (BD Biosciences, San Jose, Calif.) and treated with Red Blood Cell Lysing Buffer Hybri Max (SIGMA, Saint Louis, Mo.) to lyse red cells. Cells were washed 2 times with RPMI 1640 medium with HEPES (Gibco, Paisley, UK), supplemented with 2% of decomplemented foetal calf serum (FCS) (HYCLONE Hyclone, Logan, Utah), 50 μM of 2-mercaptoethanol (Gibco), 2 mM of L-Glutamine (Gibco) and 100 units/mL of Penicillin-Streptomycin (Gibco). Cells were counted on a Multisizer and resuspended in complete medium with RPMI 1640 medium (Gibco), supplemented with 10% of decomplemented FCS (HYCLONE), 50 μM of 2-mercaptoethanol (Gibco), 2 mM of L-Glutamine (Gibco) and 100 units/mL of Penicillin-Streptomycin (Gibco). $4\times10^5$ cells per well were distributed in Flat-bottom 96 well plate (BD Biosciences, San Jose, Calif.) and stimulated with the pools of peptides corresponding to the different HRV1B or HRV14 antigens tested: HRV1B 3'Pol, HRV14 3'Pol, HRV1B VP0 and HRV14 VP0. Peptide pools were used at 1 μg/ml for each peptide. Concanavalin A (SIGMA) was used at 2.5 μg/mL as a positive stimulation control.

After 3 days of stimulation at 37° C., 5% $CO_2$, supernatants were harvested and frozen at −80° C. until analysis.

IL-2, IL-4, IL-5, TNF-α and IFN-γ concentrations were measured using the cytometric bead array (CBA) mouse Th1/Th2 cytokine kit (BD Biosciences, San Diego, Calif.). The samples were analyzed using Facscalibur (Becton Dickinson) FACS. Data were analyzed using FCAP Array software (Becton Dickinson).

Cytokine ELISPOTs

Splenocytes were collected and prepared as described above.

$2\times10^5$ cells per well were distributed and stimulated with the pools of peptides as described above, and murine IL-2 at 20 U/ml in 96-well multiscreenHTS HA plates Cellulose ester, 0.45 μM (Millipore, Bedford, Mass.). Concanavalin A (SIGMA) was used at 2.5 μg/mL as a positive stimulation control. Nates had been previously coated overnight at 4° C. either with rat anti-mouse IFN-γ antibody (BD Pharmingen, San Diego, Calif.) or with rat anti-mouse IL-5 antibody (BD Pharmingen) at 1 μg per well in sterile PBS 1×, and blocked 1 h at 37° C. in complete medium. Stimulation of splenocytes was performed 18 h at 37° C., 5% of $CO_2$.

Plates were washed 3 times with PBS 1× and then 3 times with PBS-Tween 0.05%. Biotinylated rat anti-mouse IFN-γ or IL-5 antibody (BD PharMingen) were distributed at 100 ng per well in PBS-Tween 0.05%, 2 h at 20° C., in the dark.

Plates were washed 3 times with PBS-Tween 0.05% and incubated with streptavidin-horseradish peroxydase (Southern Biotech) in PBS-Tween 0.05%, 1 h at 20° C., in the dark.

Plates were then washed 3 times with PBS Tween 0.05%, and then 3 times with PBS 1×.

Substrate solution (3-amino-9-ethylcarbazole, AEC) was added 15 min at 20° C. in the dark to reveal spots. Reaction was stopped with water. AEC substrate solution was prepared by mixing 9 ml distilled water, 1 ml acetate buffer, 0.250 ml AEC (SIGMA) and 5 μl $H_2O_2$ then filtering the solution at 0.22 μm. Each spot corresponding to an IFN-γ or IL-5 secreting cell was enumerated with an automatic ELISPOT reader. Negative controls background values were subtracted. Results were expressed as number of IFN-γ or IL-5 spots per $10^6$ splenocytes.

Results

Antibody Response Against HRV16 VP0

The inventors first assessed the immunogenicity of subcutaneously delivered HRV16 VP0 protein. Analysis of antibody responses by Western Blot showed that IgG specific for HRV16 VP0 was detectable in serum 28 days post-immunization. In mice treated with VP0 protein alone, VP0-specific IgG1 and IgG2c, Th2 and Th1 associated IgG isotypes respectively, were detected.

Hypothesizing a Th1 oriented immune response might be beneficial to the outcome of rhinovirus infection, the inventors attempted to induce a Th1 skewed response to HRV16 VP0 using a combination of incomplete freund's (IFA) and CpG adjuvants (IFA/CpG). The addition of IFA/CpG to the immunogen switched the antibody response towards a substantially more prominent IgG2c response.

Cellular Responses Against HRV16 VP0

Having established that HRV16 VP0 is immunogenic in mice, the inventors next assessed the T cell response to immunization by measuring splenocyte cytokine production in response to stimulation with VP0 (or control polymerase) peptides.

Figure 1:
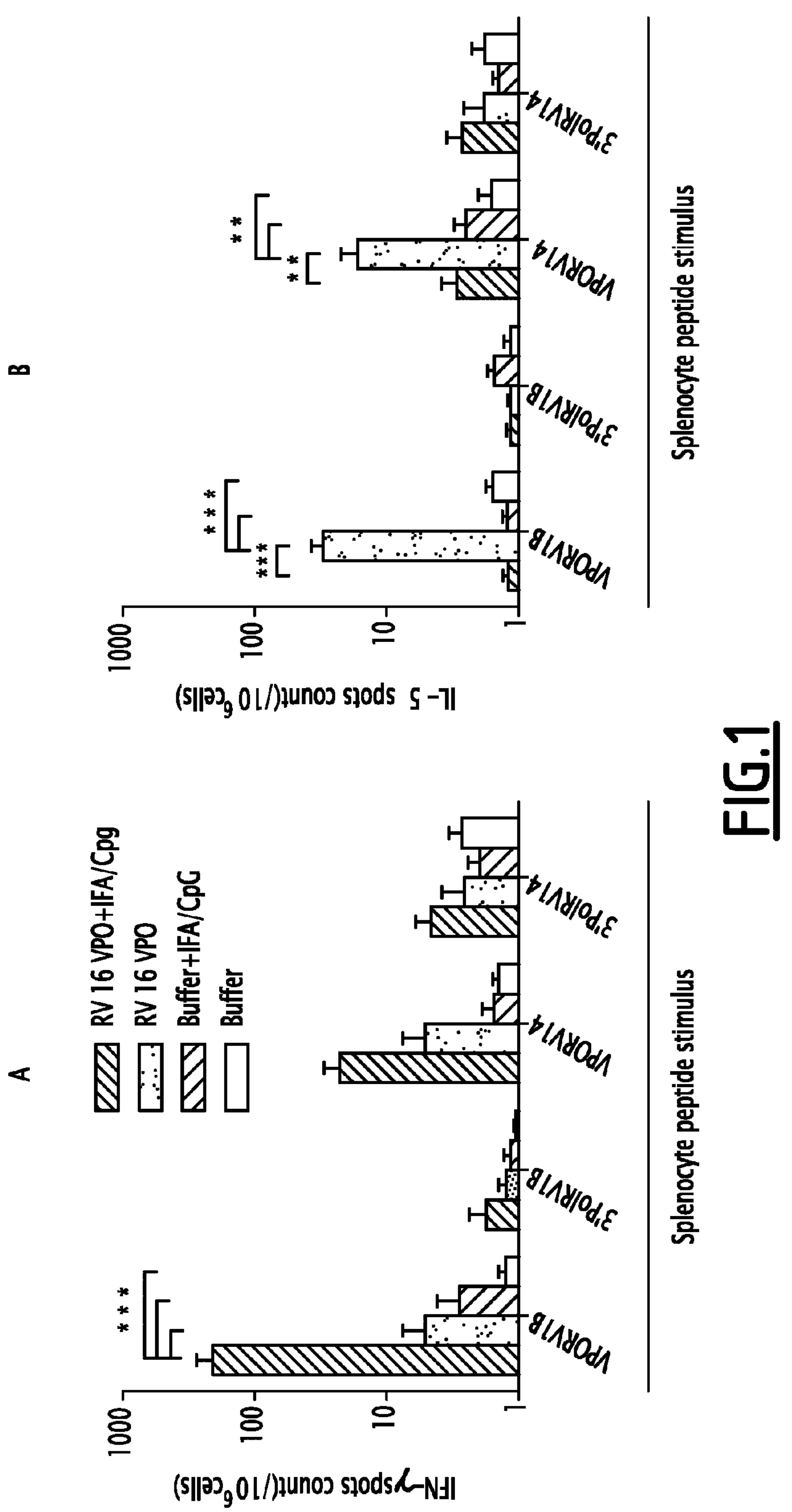
FIG. 1 is a set of histograms representing the number of IFN-γ (panel A) and IL-5 (panel B) producing cells (/$10^6$ cells), enumerated by ELISPOT in splenocytes of mice immunized subcutaneously with HRV16 VP0 protein (RV16 VP0) or buffer, with or without IFA/CpG adjuvant (IFA/Cpg), after stimulation of splenocytes with VP0 from HRV1B (VP0 RV1B) or from HRV14 (VP0 RV14) or with 3'Pol peptide pools from HRV1B (3'Pol RV1B) or from HRV14 (3'Pol RV14), the splenocytes being harvested 28 days post-immunization.

Stimulation with control viral polymerase peptides did not induce cytokine production. In both ELISPOT (FIG. 1) and cytometric bead array (FIG. 2) assays VP0 peptide pool stimulation induced IL-5, or both IL-5 and IFN-γ production respectively, in cells from mice immunized with VP0 protein alone, indicating a Th2 or mixed Th1/Th2 orientated response. The addition of IFA/CpG adjuvant to the immunogen caused a near complete suppression of IL-5 and substantial increase in IFN-γ responses. Importantly, splenocytes from major group HRV16 VP0 protein immunized mice produced cytokines when stimulated with a pool of VP0 peptides from a heterologous strain (HRV1B) of the same species (Type A rhinovirus) but belonging to the minor group and with a pool of VP0 peptides from a strain (HRV14) belonging to an another species (Type B rhinovirus), indicating cross-serotype and inter-group reactivity.

This example thus demonstrates the immunization induces a peptide specific, cross-serotype immune response.

Example 4: Outcome of HRV Challenge in Immunized Mice

This example demonstrates the potency of the immunogenic compositions of the invention to protect against rhinovirus infection in mice challenged with rhinovirus.

Materials and Methods

Rhinovirus Production

Rhinovirus (HRV) serotypes 1B and 29 (ATCC ref VR-1366 and VR-1139) were propagated in H1 HeLa cells (ATCC ref CRL-1958) that are highly permissive to rhinovirus infection. Cells were infected for 1 h at room temperature with shaking and incubated at 37° C. until approximately 90% cytopathic effect (CPE) was observed. Harvested cells were then washed, re-suspended in sterile PBS and lysed by repeated freeze-thawing. Cell debris was pelletted by centrifugation. Virus was precipitated with 0.5 M NaCl and 7% (w/v) polyethylene glycol 6000 (Fluka, Germany). After further PBS washes and filtration with a 0.2 μM syringe filter, virus was concentrated using Amicon ultra centrifugal filtration devices (Millipore, USA).

HRV stocks were originally obtained from the American Type Tissue Culture Collection (ATCC) and were periodically neutralised with ATCC reference antisera to confirm serotype.

A purified HeLa lysate preparation was generated as a control for virus binding ELISA assays. Purification was performed using the same protocol as described for RV stocks, but from uninfected H1 HeLa cells.

Virus was titrated in Ohio HeLa cells (UK Health Protection Agency catalogue ref 84121901) prior to use and tissue culture infectious dose 50% (TCID50) was calculated using the Spearman-Karber method.

In Vivo Protocols

Mice—

Wild type (w/t), specific pathogen free, female C57BL/6 mice were purchased from Harlan or Charles River UK and housed in individually ventilated cages.

C57BL/6 Immunisation and Infection Studies—

On days 0 and 21 w/t C57BL/6 mice were immunised subcutaneously with either 100 μl of emulsion containing: 10 μg HRV16 VP0 protein, 10 μl CpG oligonucleotide (100 μM ODN 1826; Invivogen, USA), and 40 μl incomplete freund's adjuvant (IFA) (Sigma-Aldrich) in sterile PBS (PAA laboratories), or IFA/CpG adjuvant alone, or PBS alone. On day 51, mice were challenged intranasally with $5\times10^6$ TCID50 of HRV1B or HRV29, or mock challenged with 50 μl PBS. The protocols carried out in the different groups of mice are summarised in Table 4.

TABLE 4

| Protocols | | | |
|---|---|---|---|
| Group | Immunisation 1 | Immunisation 2 | Challenge |
| RV-Immunised | HRV16 VPo + IFA/CpG | HRV16 VPo + IFA/CpG | HRV1B or HRV29 |
| RV-Adjuvant | IFA/CpG | IFA/CpG | HRV1B or HRV29 |
| RV-PBS | PBS | PBS | HRV1B or HRV29 |
| PBS-Immunised | HRV16 VPo + IFA/CpG | HRV16 VPo + IFA/CpG | PBS |

Mice were killed by terminal anaesthesia with pentobarbitone at various time-points during the 14 days following intranasal challenge. In an initial experiment, mice were 'immunised' with PBS as a control (RV-PBS group in table 4) to assess the effects of adjuvant treatment alone (RV-adjuvant in table 4). No differences in the results were observed between the RV-adjuvant and the RV-PBS groups in any endpoint analyses. The RV-PBS group was therefore not included in subsequent studies and no data are displayed for this group of mice.

Tissue Harvesting and Processing

Bronchoalveolar Lavage (BAL)—

Lungs were lavaged via the trachea with 1.5 ml BAL fluid (PBS, 55 mM disodium EDTA (Gibco), 12 mM lidocaine hydrochloride monohydrate (Sigma-Aldrich)) and cells were separated by centrifugation according to the method described by Bartlett & Walton (2008) *Nature Medicine* 14:199-204.

Red cells were lysed using ACK buffer (0.15 M $NH_4Cl$, 1.0 mM $KHCO_3$, 0.1 mM $Na_2EDTA$ in $dH_2O$) and cells stored in RPMI 1640 medium (PAA laboratories) (containing 10% FCS, 100 U/ml penicillin, 100 μg/ml streptomycin (P/S)).

Lung Tissue Cells for Flow Cytometry Assays—

Lung tissue was incorporated in a digestion buffer (RPMI 1640 medium, P/S, 1 mg/ml collagenase type XI (Sigma-Aldrich), 80 U/ml bovine pancreatic DNase type I (Sigma-Aldrich)), crudely homogenised using the gentleMACS tissue dissociator (Miltenyi Biotech) and incubated at 37° C. for 45 min. After homogenisation to generate a single cell suspension, red cells were lysed by addition of ACK buffer.

Cells were then filtered through a 100 μm cell strainer, washed with PBS and re-suspended in RPMI 1640 medium supplemented with 10% FCS, P/S.

Lung Tissue for RNA Extraction—

A small upper lobe of the right lung was excised and stored in "RNA later" RNA stabilisation buffer (Qiagen) at −80° C.

Blood—

Blood was collected from the carotid arteries into "microtainer" serum separation tubes (BD biosciences). Serum was separated by centrifugation and stored at −80° C. until analysis.

BAL Cell Cytospin Assay

BAL cells were spun onto slides using the cytospin 3 system (Shandon, USA) and stained with the Reastain Quick-diff kit (Reagena, Finland). At least 300 cells per slide were counted blind to experimental conditions.

Flow Cytometry

Surface Marker Staining—

Surface marker staining of lung and BAL lymphocytes was performed using standard protocols. Briefly, 1-10×$10^5$ lung or BAL cells were stained with "live/dead fixable dead cell stain kit" (Invitrogen) for 30 min at 4° C. Cells were then washed and incubated with 5 μg/ml anti-mouse CD16/CD32 to block non-specific binding to FC receptors. Directly fluorochrome-conjugated antibodies specific for CD3 (CD3-Pacific Blue; clone 500A2), CD4 (CD4-APC; clone RM4-5), CD8 (CD8-PE; clone 53-6.7), CD69 (CD69-FITC; clone H1.2F3), CD62L (CD62L-PE; clone MEL-14), CD44 (CD44-FITC; clone IM7) T cell markers, all purchased from BD biosciences, were added directly and cells incubated for a further 30 min period at 4° C. After several washes, cells were fixed with 2% formaldehyde for 20 min at room temperature, again washed, re-suspended in PBS 1% BSA and stored at 4° C.

Intracellular Cytokine Staining—

For intracellular cytokine staining, lung cells were stained for dead cells and surface markers, and fixed as described. After washing, cells were permeablised with 0.5% (w/v) saponin (Fluka) for 10 min at room temperature. Fluorochrome conjugated anti-cytokine antibodies in PBS 0.5% saponin were added directly and cells incubated for a further 30 min at 4° C. Cells were again washed, re-suspended in PBS 1% BSA and data acquired immediately.

Data Acquisition—

Flow cytometry data was acquired using CyanADP (Dako, USA) or FACSCanto (BD biosciences) cytometers and analysed using Summit v4.3 software (Dako, USA).

Enzyme Linked Immunospot (ELISPOT) Assay

IFN-γ and IL-4—

96 well Multiscreen HA ELISPOT plates (Millipore) were coated overnight at 4° C. with 5 μg/ml purified anti-mouse IFN-γ or IL-4 antibody (both BD biosciences) in PBS. The following day, plates were washed and blocked with RPMI 1640 medium supplemented with 10% FCS, P/S for 3 h at 37° C. 5×$10^4$ or 1×$10^5$ lung cells in 100 μl RPMI 1640 medium supplemented with 10% FCS, P/S were added to each well, followed by 100 μl medium containing various stimuli, as described in table 5.

TABLE 5

ELISPOT stimuli

| Stimulus | Details | Final concentration |
|---|---|---|
| PMA/Ionomycin | n/a | 50/500 ng/ml |
| Ovalbumin | n/a | 500 μg/ml |
| HRV1Bor HRV29 | Purified virus preparations as used for infections | 1 × $10^6$TCID$_{50}$/ml |
| Peptide pool C | RV1B VPO region overlapping peptides | 4 μg/ml |
| Peptide pool E | RV14 VPO region overlapping peptides | 4 μg/ml |
| RV16 VPO protein | Peptide as used for immunisation | 25 μg/ml |
| DMSO | Control for peptide pools | 0.8% (v/v) |
| Unstimulated | Control for virus, OVA and PMA/ionomycin stimuli | RPMI 1640 medium. 10% FCS P/S |

n/a: not applicable

Nates were incubated for 3 days at 37° C. Nates were then washed with PBS 0.05% Tween 20 (PBS-T; Sigma-Aldrich) and subsequently with sterile water to lyse cells. Biotinylated secondary antibodies, at 2 μg/ml in PBS 0.5% BSA, were then added and incubated for 2 h at 37° C. After washes, plates were incubated with Extravidin alkaline phosphatase (Sigma-Aldrich) for 45 min at room temperature and washed with PBS-T followed by sterile PBS. NBT/BCIP substrate (Sigma-Aldrich) was added and incubated for a further 5 min period. Reactions were stopped by extensive washing with tap water.

Data Acquisition—

All ELISPOT data were acquired using an AID version 3.5 EliSpot Reader (AID GmbH, Germany).

Enzyme Linked Immunosorbant (ELISA)

Cytokines—

All cytokine and chemokine proteins were assayed using protocols and reagents from Duoset ELISA kits (R&D systems) and Nunc Maxisorp Immunoplates (Thermo-Fisher). All samples were measured in duplicate and protein levels were quantified by comparison with an 8 point standard curve of recombinant protein.

RV-Specific Immunoglobulins—

RV-specific IgG's and IgA were measured using in-house assays. For all assays, Nunc Maxisorp Immunoplates (Thermo-Fisher) were coated with purified RV innoculum or HeLa lysate control to a protein concentration of 5 μg/ml and incubated overnight at 4° C. Nates were then washed with PBS and blocked by adding PBS containing 0.05% Tween 20 and 5% milk powder (PBST-milk). Serum or BAL, diluted in PBS 5% milk were then added and plates incubated overnight at 4° C. Each dilution was analysed in duplicate. Nates were washed with PBST and bound immunoglobulins were detected using biotinylated rat anti-mouse IgG1, IgG2a or IgA (all BD biosciences) diluted 1/1000 before the addition of streptavidin-peroxydase (Invitrogen, Paisley UK). Finally, TMB substrate (Invitrogen) was added and reactions were stopped by addition of an equal volume of $H_2SO_4$.

For analysis of IgA in BAL, samples were allowed to mix with protein G sepharose beads (Sigma-Aldrich) overnight at 4° C. After centrifugation to remove the sepharose beads and bound IgG, the unbound fraction containing IgA was retained and used in ELISA experiments. Depletion of IgG in the samples was confirmed by showing loss of binding to HRV by ELISA.

In all assays, antibody binding to a HeLa lysate control was assessed on the same plate as binding to virus innoculum. HeLa lysate values were subtracted during analysis to show virus-specific antibody binding.

Data Acquisition—

In all ELISA assays absorbance was measured at 450 nm using a Spectramax Nus plate reader and analysed with Softmax Pro v50.2 software (Molecular Devices).

Neutralisation Assays

Neutralisation of HRV serotypes was measured in infected HeLa cells. Sera of a given treatment group and time point post-challenge were pooled and serial dilutions in DMEM medium supplemented with 4% FCS, P/S were made. 50 μl of the serial dilutions to be tested were introduced (in duplicate) into wells of 96 well flat bottom cell culture plates, before the addition of 50 μl from the purified stock of HRV in DMEM medium. The appropriate titer of HRV serotype introduced in the wells was defined as the dilution of the stock of HRV which produced a cytopathic effect (CPE) of 90% in 3 days. Nates were incubated at room temperature with shaking to form Antibody-Antigen complexes. After 1 h, $1.5\times10^5$ Ohio HeLa cells were added to each well and plates were further incubated for 48-96 h at 37° C.

CPE of HRV was measured by crystal violet cell viability assay. Nates were washed with PBS and 100 μl of 0.1% crystal violet solution was added to each well and incubated for 10 min at room temperature. Nates were then washed with distilled $H_2O$ and air dried. 100 μl/well of 1% sodium dodecyl sulfate (SDS) was added and plates were incubated at room temperature with shaking for 15 min or until all crystal violet had dissolved. Optical Density was measured at 560 nm.

Taqman Quantitative PCR

RNA Extraction—

Lung tissue was placed in RLT buffer (Qiagen, USA) and homogenised using a rotor-stator homogenizer. RNA was then extracted using reagents and protocols from the RNeasy Mini Kit (Qiagen), including on-column Dnase digestion step.

Reverse Transcription— cDNA was generated in 20 μl reactions using the Omniscript RT kit (Qiagen) and random hexamer primers (Promega, USA). All reactions comprised 1 μM random primers, 0.5 mM (each) dNTPs and 0.2 U/μl reverse transcriptase. Reactions were performed at 37° C. for 1 h.

PCR—

Quantitative PCR (qPCR) reactions were carried out using Quantitect Probe PCR Mastermix (Qiagen) and primers and FAM/TAMRA labelled probes specific for the gene of interest, 18S ribosomal RNA, or the 5' untranslated region of RV. Primers and probes are described in table 6.

TABLE 6

Taqman qPCR primers and probes

| Assay | Primer | Sequence 5'-3' | SEQ ID | Concentration (nM) |
|---|---|---|---|---|
| IL-4 | IL-4 Forward | ACAGGAGAAGGGACGCCAT | 23 | 900 |
| | IL-4 Reverse | GAAGCCCTACAGACGAGCTCA | 24 | 900 |
| | IL-4 Probe | FAM-TCCTCACAGCAACGAAGA-TAMRA | 25 | 100 |

TABLE 6-continued

Taqman qPCR primers and probes

| Assay | Primer | Sequence 5'-3' | SEQ ID | Concentration (nM) |
|---|---|---|---|---|
| IFN-γ | IFN-γ Forward | TCAAGTGGCATAGATGTGGAAGAA | 26 | 900 |
| | IFN-γ Reverse | TGGCTCTGCAGGATTTTCATG | 27 | 900 |
| | IFN-γ Probe | FAM-TCACCATCCTTTTGCCAGTT-TAMRA | 28 | 100 |
| IL-17a | IL-17a Forward | TCAGACTACCTCAACCGTTCCA | 29 | 900 |
| | IL-17a Reverse | AGCTTCCCAGATCACAGAGGG | 30 | 900 |
| | IL-17a Probe | FAM-TCACCCTGGACTCTCCACCGCA-TAMRA | 31 | 100 |
| HRV | HRV Forward | GTGAAGAGCCSCRTGTGCT | 32 | 50 |
| | HRV Reverse | GCTSCAGGGTTAAGGTTAGCC | 33 | 300 |
| | HRV Probe | FAM-TGAGTCCTCCGGCCCCTGAATG-TAMRA | 34 | 100 |
| 18S | 18S Forward | CGCCGCTAGAGGTGAAATTCT | 35 | 300 |
| | 18S Reverse | CATTCTTGGCAAATGCTTTCG | 36 | 300 |
| | 18S Probe | FAM-ACCGGCGCAAGACGGACCAGA-TAMRA | 37 | 100 |

Cycling conditions were as follows: 2 min at 50° C., 10 min at 95° C. and 45 cycles of 95° C. for 15 seconds and 60° C. for 1 minute. For the 18S assay, cDNA was diluted 1 in 100 in nuclease free water before addition to the reaction.

Reactions were performed on a 7500 fast real time PCR system (ABI).

Results

Following immunogenicity experiments, the effect of immunization with HRV16 VP0 protein adjuvanted with IFA/CpG on HRV-induced disease was assessed in the mouse infection model. These experiments were carried out to determine if prior immunization could induce a similar Th1/Tc1 response in the airways of infected mice as found systemically and to determine the effect of this on disease markers and virus load.

Immunization Enhances Airway T Cell Responses to Infection with a Heterologous RV Strain The inventors assessed the impact of immunization with HRV16 VP0 in the presence of IFA/CpG on the immune responses observed after intranasal challenge with a heterologous serotype of HRV (HRV1B).

Differential staining of bronchoalveolar lavage (BAL) leukocytes by cytospin assay showed that immunization significantly increased the magnitude of the lymphocyte response to infection when compared to adjuvant treated and infected mice (group RV-Adjuvant) (FIG. 3).

To characterize this lymphocyte response further, T cells in BAL and lung were analyzed by flow cytometry. CD4+ T cell number was increased in both BAL and lung, and CD8+ T cell number was increased in BAL of mice immunized and infected (group RV-immunized) vs mice treated with adjuvant and infected (group RV-adjuvant) on day 6 post-infection (FIG. 4). This response was dominated by CD4+ T cells. In infected mice the proportion of BAL and lung T cells expressing the early activation marker CD69 was also significantly increased by immunization (FIG. 5). Enhanced levels of T cell chemokine CXCL10 in BAL were also observed in immunized and infected vs adjuvant treated and infected mice (FIG. 6).

Immunization Induces Antigen-Specific Lung Th1 Responses to Infection

The inventors also examined the effect of immunization on the polarity and antigen specificity of T cell responses after a heterologous challenge with the HRV1B serotype. Immunization significantly increased the levels of Th1 (IFN-γ), and Th2 (IL-4) cytokine mRNAs in lung tissue of HRV1B challenged mice (FIG. 7). Consistent with the use of the Th1-promoting adjuvants, this response was dominated by IFN-γ in the group of RV-immunized mice. At the protein level, IL-4 was undetectable in BAL of all groups whereas increased IFN-γ were detected at 24 and 48 h post-infection only in immunized and challenged mice (group RV-immunized) (FIG. 8).

Since immunization generated cross-reactive, VP0-specific cells in the spleen, the inventors determined if cross-reactive memory cells were recruited to the airways after infection by measuring IFN-γ production by lung cells stimulated with different stimuli using ELISPOT assays. The frequency of IFN-γ producing lung cells was greatest in mice which were both immunized and RV challenged (group RV-immunized) (FIG. 9). Stimulation with the same protein as the one used for immunization (HRV16 VP0), with a live heterologous serotype (HRV1B), or with heterologous HRV1B or HRV14 VP0 peptide pools induced similar IFN-γ responses. With the exception of HRV16 VP0 stimulation in RV-adjuvant treated mouse cells, IFN-γ producing cell frequency was not significant above unstimulated controls in other treatment groups. HRV16 VP0 immunization therefore induced cross-reactive Th1/Tc1 responses in the lung in response to HRV1B challenge that were of significantly greater magnitude than with HRV infection alone.

Immunization Increases T Cell Responses to Infection with a More Distantly Related HRV Serotype HRV16 and HRV1B belong to different receptor binding groups, but are highly related at the amino acid level within VP0. To establish if immunization induces more broadly cross-reactive responses among type A rhinoviruses, the inventors therefore determined the effects on responses to challenge with the more distantly related serotype, HRV29.

BAL cell analysis by cytospin assay revealed increased lymphocyte numbers in RV-immunized vs RV-adjuvant treated mice (Figure to). Total and activated CD4+ T cell number in lung tissue (FIG. 11) and BAL (FIG. 12) were also significantly increased compared to infection or immunization treatments alone. When lung leukocytes were stimulated with HRV antigens in ELISPOT assays, IFN-γ producing cell frequency was significantly greater after stimulation with the challenge serotype (HRV29) in RV-immunized vs RV-adjuvant treated mice (FIG. 13). Similar increases were apparent upon stimulation with heterologous HRV1B and HRV14 VP0 derived peptide pools, again indicating the presence of cross-serotype cell mediated immune responses. It was also shown by intracellular flow cytometry a significant increase of IFN-γ producing CD8+ T cells in the lungs of infected and immunized mice (1 day after infection) followed by an increase of IFN-γ producing CD4+ T cells (6 days after infection) while nothing significant was observed in the other groups of mice (RV-adjuvant or PBS-immunized groups) (FIG. 14). This suggests that the cell mediated immune response induced by the composition of the invention is dominated by a Th1 response but a Tc1 immune response is also involved to a lesser extent.

Immunization Enhances Generation of Lung Effector Memory T Cells

Activated CD4+ T cells persisted in the lungs of immunized and challenged mice on day 14 post-infection (FIG. 11). To determine if this represented enhanced generation of local memory T cells the inventors analyzed by flow cytometry the expression of memory markers on lung CD4+ T cells. The proportion of CD4+ T cells expressing the CD44+ $CD62L^{low}$ (effector memory marker) phenotype was significantly higher in the group of RV-immunized mice compared to the other groups (RV-adjuvant or PBS-immunized groups). On the other hand, the proportion of lung CD4+ T cells expressing a central memory phenotype, CD44+ $CD62L^{high}$, was not increased in the group of RV-immunized mice (FIGS. 15 and 16).

Immunization Enhances Neutralizing Antibody Responses to Heterologous Virus Infection The inventors also studied the effect of immunization on the generation of humoral immune responses by measuring the ability of serum and BAL immunoglobulins to bind and neutralize the activity of rhinovirus.

ELISA binding assays showed that immunization with HRV16 VP0 in the absence of challenge induced cross-reactive HRV29 and HRV1B binding antibodies observed in the serum but not in the BAL (FIGS. 17-20).

When followed by HRV1B or HRV29 challenge, immunization generated a faster and greater cross-reactive antibody response observed both in the serum and in the BAL.

While immunization with HRV16 VP0 without a rhinovirus challenge did not induce neutralizing antibodies, a faster and greater induction of neutralizing antibodies was observed when immunization with HRV16 VP0 was followed by a rhinovirus challenge. The induction of neutralizing antibodies against the infecting rhinovirus strain/serotype was consistently observed in the group of immunized mice (RV-immunized) while it was inconsistently observed in the group of adjuvant-treated mice (RV-adjuvant). Furthermore, the production of neutralizing antibodies was slower and of weaker magnitude in the RV-adjuvant group. (See FIGS. 21 and 22). The neutralizing antibodies titers in each group of mice (RV-immunized and RV-adjuvant) were measured in an in vitro neutralization assay on Ohio Hela cells using the same strain of rhinovirus that the one used in the challenge test (table 7).

TABLE 7

| ID50 values | | | | |
|---|---|---|---|---|
| Infection serotype | Day | RV-immunized | RV-adjuvant | PBS-immunized |
| HRV1B | 6 | 326.9 | — | — |
| | 14 | 3218 | 160.2 | — |
| HRV29 | 6 | 150.1 | — | — |
| | 14 | 309.2 | — | — |

As mentioned in table 7, the mean inverse dilution of sera from HRV1B-immunized group that produces a 50% reduction of CPE on Ohio hela cells is 1328 vs 160.2 in the HRV1B-adjuvant group.

Collectively, these data indicate that immunization with HRV16 VP0 in the presence of IFA/CpG is capable of substantially enhancing neutralizing antibody responses to infection with heterologous viruses.

Immunization Accelerates Virus Clearance

Finally, the inventors determined whether Th1 and neutralizing antibody responses induced by immunization conferred any benefit on control of virus replication. When immunized mice were challenged with HRV1B or HRV29 (RV-immunized), the clearance of the virus from the lung was observed on day 4 and on day 6 after the challenge respectively and was greatly accelerated by comparison to the one observed in the adjuvant-treated group (RV-Adjuvant) (see FIGS. 23 and 24).

Example 5: Immunogenicity of 3'Pol and VP-Pol Proteins in Mice 7 week-old C56BL/6 or BalB/cByJ mice were immunized with either the last 105 amino acids of the RNA polymerase of HRV16 (3'Pol RV16) or with the fusion protein comprising the first 135 amino acids of VP0 of HRV1B coupled to the last 105 amino acids of the RNA polymerase of HRV1B (VP-Pol RV1B) according to the protocol described in example 3.

The results displayed in FIGS. 25 to 27 show that the addition of IFA/CpG to the immunogen switched the cellular immune response towards a Th1 cellular immune response. As shown for HRV16 VP0 in the previous examples, the cell mediated immune response observed is a specific cross-reactive cell mediated immune response. In the case of immunization with 3'Pol RV16, IFN-γ responses were induced only against the peptide pool B of 3'Pol (this peptide pool encompasses the last 105 amino acids of the C-terminal end of the RNA polymerase protein) of heterologous serotypes of rhinoviruses (HRV1B and HRV14). In the case of immunization with VP-Pol RV1B, IFN-γ responses were induced only against the peptide pool B of 3'Pol (this peptide pool encompasses the last 105 amino acids of the C-terminal end of the RNA polymerase protein) and the peptide pool C of VP0 (this peptide pool encompasses the first 135 amino acids of VP0) of HRV1B.

Example 6: Immunization with DNA Constructs 7 week-old C56 BL/6 or BalB/cByJ mice were given by intramuscular route in the legs on days 0 and 21 100 μg of the pcDNA3.1 plasmid encoding either the last 105 amino acids of the RNA polymerase of HRV14 (3'Pol DNA RV14) or the VP0 amino acid sequence of HRV16 (VP0 DNA RV16). The splenocytes were harvested on day 28 and stimulated with different pools of peptides and analyzed for their IFN-γ responses.

The results presented in FIG. 28 show that DNA immunization with plasmids encoding the last 105 amino acids of the RNA polymerase of a rhinovirus or the VP0 protein of a rhinovirus are able to induce a specific cross-reactive cell mediated immune response.

SEQUENCE LISTING

```
<160> NUMBER OF SEQ ID NOS: 41

<210> SEQ ID NO 1
<211> LENGTH: 69
<212> TYPE: PRT
<213> ORGANISM: Artificial Sequence
<220> FEATURE:
<223> OTHER INFORMATION: Description of Artificial Sequence: Synthetic
      HRV16 VP4 peptide. This is an isolated HRV protein capsid, derived
      from the VPo polyprotein precursor, which lies at the
      interface between the capsid and the interior genomic RNA.
<220> FEATURE:
<223> OTHER INFORMATION: VPo is a protein precursor derived from the HRV
      P1 polyprotein and which consists of the amino acid
      sequence of VP4 and VP2 peptides

<400> SEQUENCE: 1

Met Gly Ala Gln Val Ser Arg Gln Asn Val Gly Thr His Ser Thr Gln
1               5                   10                  15

Asn Met Val Ser Asn Gly Ser Ser Leu Asn Tyr Phe Asn Ile Asn Tyr
            20                  25                  30

Phe Lys Asp Ala Ala Ser Ser Gly Ala Ser Arg Leu Asp Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln
65


<210> SEQ ID NO 2
<211> LENGTH: 69
<212> TYPE: PRT
<213> ORGANISM: Artificial Sequence
<220> FEATURE:
<223> OTHER INFORMATION: Description of Artificial Sequence: Synthetic
      HRV14 VP4 peptide. This is an isolated HRV protein capsid, derived
      from the VPo polyprotein precursor, which lies at the
      interface between the capsid and the interior genomic RNA.
```

```
<220> FEATURE:
<223> OTHER INFORMATION: VPo is a protein precursor derived from the HRV
      P1 polyprotein and which consists of the amino acid
      sequence of VP4 and VP2 peptides.

<400> SEQUENCE: 2

Met Gly Ala Gln Val Ser Thr Gln Lys Ser Gly Ser His Glu Asn Gln
1               5                   10                  15

Asn Ile Leu Thr Asn Gly Ser Asn Gln Thr Phe Thr Val Ile Asn Tyr
            20                  25                  30

Tyr Lys Asp Ala Ala Ser Thr Ser Ser Ala Gly Gln Ser Leu Ser Met
        35                  40                  45

Asp Pro Ser Lys Phe Thr Glu Pro Val Lys Asp Leu Met Leu Lys Gly
    50                  55                  60

Ala Pro Ala Leu Asn
65


<210> SEQ ID NO 3
<211> LENGTH: 260
<212> TYPE: PRT
<213> ORGANISM: Artificial Sequence
<220> FEATURE:
<223> OTHER INFORMATION: Description of Artificial Sequence: Synthetic
      HRV16 VP2 peptide. This is an isolated HRV protein capsid, derived
      from the VPo polyprotein precursor, which lies at the
      external side of the capsid.

<400> SEQUENCE: 3

Ser Pro Ser Val Glu Ala Cys Gly Tyr Ser Asp Arg Ile Ile Gln Ile
1               5                   10                  15

Thr Arg Gly Asp Ser Thr Ile Thr Ser Gln Asp Val Ala Asn Ala Val
            20                  25                  30

Val Gly Tyr Gly Val Trp Pro His Tyr Leu Thr Pro Gln Asp Ala Thr
        35                  40                  45

Ala Ile Asp Lys Pro Thr Gln Pro Asp Thr Ser Ser Asn Arg Phe Tyr
    50                  55                  60

Thr Leu Asp Ser Lys Met Trp Asn Ser Thr Ser Lys Gly Trp Trp Trp
65                  70                  75                  80

Lys Leu Pro Asp Ala Leu Lys Asp Met Gly Ile Phe Gly Glu Asn Met
                85                  90                  95

Phe Tyr His Phe Leu Gly Arg Ser Gly Tyr Thr Val His Val Gln Cys
            100                 105                 110

Asn Ala Ser Lys Phe His Gln Gly Thr Leu Leu Val Val Met Ile Pro
        115                 120                 125

Glu His Gln Leu Ala Thr Val Asn Lys Gly Asn Val Asn Ala Gly Tyr
    130                 135                 140

Lys Tyr Thr His Pro Gly Glu Ala Gly Arg Glu Val Gly Thr Gln Val
145                 150                 155                 160

Glu Asn Glu Lys Gln Pro Ser Asp Asp Asn Trp Leu Asn Phe Asp Gly
                165                 170                 175

Thr Leu Leu Gly Asn Leu Leu Ile Phe Pro His Gln Phe Ile Asn Leu
            180                 185                 190

Arg Ser Asn Asn Ser Ala Thr Leu Ile Val Pro Tyr Val Asn Ala Val
        195                 200                 205

Pro Met Asp Ser Met Val Arg His Asn Asn Trp Ser Leu Val Ile Ile
    210                 215                 220

Pro Val Cys Gln Leu Gln Ser Asn Asn Ile Ser Asn Ile Val Pro Ile
225                 230                 235                 240
```

Thr Val Ser Ile Ser Pro Met Cys Ala Glu Phe Ser Gly Ala Arg Ala
245 250 255

Lys Thr Val Val
260

<210> SEQ ID NO 4
<211> LENGTH: 260
<212> TYPE: PRT
<213> ORGANISM: Artificial Sequence
<220> FEATURE:
<223> OTHER INFORMATION: Description of Artificial Sequence: Synthetic HRV14 VP2 peptide. This is an isolated HRV protein capsid, derived from the VPo polyprotein precursor, which lies at the external side of the capsid.

<400> SEQUENCE: 4

Ser Pro Asn Val Glu Ala Cys Gly Tyr Ser Asp Arg Val Gln Gln Ile
1 5 10 15

Thr Leu Gly Asn Ser Thr Ile Thr Thr Gln Glu Ala Ala Asn Ala Val
20 25 30

Val Cys Tyr Ala Glu Trp Pro Glu Tyr Leu Pro Asp Val Asp Ala Ser
35 40 45

Asp Val Asn Lys Thr Ser Lys Pro Asp Thr Ser Val Cys Arg Phe Tyr
50 55 60

Thr Leu Asp Ser Lys Thr Trp Thr Thr Gly Ser Lys Gly Trp Cys Trp
65 70 75 80

Lys Leu Pro Asp Ala Leu Lys Asp Met Gly Val Phe Gly Gln Asn Met
85 90 95

Phe Phe His Ser Leu Gly Arg Ser Gly Tyr Thr Val His Val Gln Cys
100 105 110

Asn Ala Thr Lys Phe His Ser Gly Cys Leu Leu Val Val Val Ile Pro
115 120 125

Glu His Gln Leu Ala Ser His Glu Gly Gly Asn Val Ser Val Lys Tyr
130 135 140

Thr Phe Thr His Pro Gly Glu Arg Gly Ile Asp Leu Ser Ser Ala Asn
145 150 155 160

Glu Val Gly Gly Pro Val Lys Asp Val Ile Tyr Asn Met Asn Gly Thr
165 170 175

Leu Leu Gly Asn Leu Leu Ile Phe Pro His Gln Phe Ile Asn Leu Arg
180 185 190

Thr Asn Asn Thr Ala Thr Ile Val Ile Pro Tyr Ile Asn Ser Val Pro
195 200 205

Ile Asp Ser Met Thr Arg His Asn Asn Val Ser Leu Met Val Ile Pro
210 215 220

Ile Ala Pro Leu Thr Val Pro Thr Gly Ala Thr Pro Ser Leu Pro Ile
225 230 235 240

Thr Val Thr Ile Ala Pro Met Cys Thr Glu Phe Ser Gly Ile Arg Ser
245 250 255

Lys Ser Ile Val
260

<210> SEQ ID NO 5
<211> LENGTH: 135
<212> TYPE: PRT
<213> ORGANISM: Artificial Sequence
<220> FEATURE:
<223> OTHER INFORMATION: Description of Artificial Sequence: Synthetic HRV16 VP135 peptide. This is an isolated HRV protein capsid comprising the first 135 N-terminal amino acids of the VPo polyprotein of HRV16.

<400> SEQUENCE: 5

```
Met Gly Ala Gln Val Ser Arg Gln Asn Val Gly Thr His Ser Thr Gln
1               5                   10                  15

Asn Met Val Ser Asn Gly Ser Ser Leu Asn Tyr Phe Asn Ile Asn Tyr
            20                  25                  30

Phe Lys Asp Ala Ala Ser Ser Gly Ala Ser Arg Leu Asp Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln Ser Pro Ser Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Pro Gln Asp Ala Thr Ala Ile Asp Lys Pro Thr Gln Pro Asp Thr Ser
        115                 120                 125

Ser Asn Arg Phe Tyr Thr Leu
    130                 135
```

<210> SEQ ID NO 6
<211> LENGTH: 329
<212> TYPE: PRT
<213> ORGANISM: Artificial Sequence
<220> FEATURE:
<223> OTHER INFORMATION: Description of Artificial Sequence: Synthetic HRV16 VP0 polyprotein. This comprises nucleocapsid proteins VP2 and VP4.

<400> SEQUENCE: 6

```
Met Gly Ala Gln Val Ser Arg Gln Asn Val Gly Thr His Ser Thr Gln
1               5                   10                  15

Asn Met Val Ser Asn Gly Ser Ser Leu Asn Tyr Phe Asn Ile Asn Tyr
            20                  25                  30

Phe Lys Asp Ala Ala Ser Ser Gly Ala Ser Arg Leu Asp Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln Ser Pro Ser Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Pro Gln Asp Ala Thr Ala Ile Asp Lys Pro Thr Gln Pro Asp Thr Ser
        115                 120                 125

Ser Asn Arg Phe Tyr Thr Leu Asp Ser Lys Met Trp Asn Ser Thr Ser
    130                 135                 140

Lys Gly Trp Trp Trp Lys Leu Pro Asp Ala Leu Lys Asp Met Gly Ile
145                 150                 155                 160

Phe Gly Glu Asn Met Phe Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190
```

-continued

Val Val Met Ile Pro Glu His Gln Leu Ala Thr Val Asn Lys Gly Asn
195 200 205

Val Asn Ala Gly Tyr Lys Tyr Thr His Pro Gly Glu Ala Gly Arg Glu
210 215 220

Val Gly Thr Gln Val Glu Asn Glu Lys Gln Pro Ser Asp Asp Asn Trp
225 230 235 240

Leu Asn Phe Asp Gly Thr Leu Leu Gly Asn Leu Leu Ile Phe Pro His
245 250 255

Gln Phe Ile Asn Leu Arg Ser Asn Asn Ser Ala Thr Leu Ile Val Pro
260 265 270

Tyr Val Asn Ala Val Pro Met Asp Ser Met Val Arg His Asn Asn Trp
275 280 285

Ser Leu Val Ile Ile Pro Val Cys Gln Leu Gln Ser Asn Asn Ile Ser
290 295 300

Asn Ile Val Pro Ile Thr Val Ser Ile Ser Pro Met Cys Ala Glu Phe
305 310 315 320

Ser Gly Ala Arg Ala Lys Thr Val Val
325

<210> SEQ ID NO 7
<211> LENGTH: 135
<212> TYPE: PRT
<213> ORGANISM: Artificial Sequence
<220> FEATURE:
<223> OTHER INFORMATION: Description of Artificial Sequence: Synthetic HRV14 VP135 peptide. This is an isolated HRV protein capsid comprising the first 135 N-terminal amino acids of the VPo polyprotein of HRV14.

<400> SEQUENCE: 7

Met Gly Ala Gln Val Ser Thr Gln Lys Ser Gly Ser His Glu Asn Gln
1 5 10 15

Asn Ile Leu Thr Asn Gly Ser Asn Gln Thr Phe Thr Val Ile Asn Tyr
20 25 30

Tyr Lys Asp Ala Ala Ser Thr Ser Ser Ala Gly Gln Ser Leu Ser Met
35 40 45

Asp Pro Ser Lys Phe Thr Glu Pro Val Lys Asp Leu Met Leu Lys Gly
50 55 60

Ala Pro Ala Leu Asn Ser Pro Asn Val Glu Ala Cys Gly Tyr Ser Asp
65 70 75 80

Arg Val Gln Gln Ile Thr Leu Gly Asn Ser Thr Ile Thr Thr Gln Glu
85 90 95

Ala Ala Asn Ala Val Val Cys Tyr Ala Glu Trp Pro Glu Tyr Leu Pro
100 105 110

Asp Val Asp Ala Ser Asp Val Asn Lys Thr Ser Lys Pro Asp Thr Ser
115 120 125

Val Cys Arg Phe Tyr Thr Leu
130 135

<210> SEQ ID NO 8
<211> LENGTH: 329
<212> TYPE: PRT
<213> ORGANISM: Artificial Sequence
<220> FEATURE:
<223> OTHER INFORMATION: Description of Artificial Sequence: Synthetic HRV14 VP0 polyprotein. This comprises nucleocapsid proteins VP2 and VP4.
<220> FEATURE:
<221> NAME/KEY: SITE
<222> LOCATION: (1)..(171)
<223> OTHER INFORMATION: pool E - 15mer synthetic peptide used for splenocyte stimulation.

<400> SEQUENCE: 8

```
Met Gly Ala Gln Val Ser Thr Gln Lys Ser Gly Ser His Glu Asn Gln
1               5                   10                  15

Asn Ile Leu Thr Asn Gly Ser Asn Gln Thr Phe Thr Val Ile Asn Tyr
            20                  25                  30

Tyr Lys Asp Ala Ala Ser Thr Ser Ser Ala Gly Gln Ser Leu Ser Met
        35                  40                  45

Asp Pro Ser Lys Phe Thr Glu Pro Val Lys Asp Leu Met Leu Lys Gly
    50                  55                  60

Ala Pro Ala Leu Asn Ser Pro Asn Val Glu Ala Cys Gly Tyr Ser Asp
65                  70                  75                  80

Arg Val Gln Gln Ile Thr Leu Gly Asn Ser Thr Ile Thr Thr Gln Glu
                85                  90                  95

Ala Ala Asn Ala Val Val Cys Tyr Ala Glu Trp Pro Glu Tyr Leu Pro
            100                 105                 110

Asp Val Asp Ala Ser Asp Val Asn Lys Thr Ser Lys Pro Asp Thr Ser
        115                 120                 125

Val Cys Arg Phe Tyr Thr Leu Asp Ser Lys Thr Trp Thr Thr Gly Ser
    130                 135                 140

Lys Gly Trp Cys Trp Lys Leu Pro Asp Ala Leu Lys Asp Met Gly Val
145                 150                 155                 160

Phe Gly Gln Asn Met Phe Phe His Ser Leu Gly Arg Ser Gly Tyr Thr
                165                 170                 175

Val His Val Gln Cys Asn Ala Thr Lys Phe His Ser Gly Cys Leu Leu
            180                 185                 190

Val Val Val Ile Pro Glu His Gln Leu Ala Ser His Glu Gly Gly Asn
        195                 200                 205

Val Ser Val Lys Tyr Thr Phe Thr His Pro Gly Glu Arg Gly Ile Asp
    210                 215                 220

Leu Ser Ser Ala Asn Glu Val Gly Gly Pro Val Lys Asp Val Ile Tyr
225                 230                 235                 240

Asn Met Asn Gly Thr Leu Leu Gly Asn Leu Leu Ile Phe Pro His Gln
                245                 250                 255

Phe Ile Asn Leu Arg Thr Asn Asn Thr Ala Thr Ile Val Ile Pro Tyr
            260                 265                 270

Ile Asn Ser Val Pro Ile Asp Ser Met Thr Arg His Asn Asn Val Ser
        275                 280                 285

Leu Met Val Ile Pro Ile Ala Pro Leu Thr Val Pro Thr Gly Ala Thr
    290                 295                 300

Pro Ser Leu Pro Ile Thr Val Thr Ile Ala Pro Met Cys Thr Glu Phe
305                 310                 315                 320

Ser Gly Ile Arg Ser Lys Ser Ile Val
                325
```

<210> SEQ ID NO 9
<211> LENGTH: 105
<212> TYPE: PRT
<213> ORGANISM: Artificial Sequence
<220> FEATURE:
<223> OTHER INFORMATION: Description of Artificial Sequence: Synthetic Last 105 amino acids of HRV16 RNA polymerase.

<400> SEQUENCE: 9

```
Ala Asp Lys Ser Ser Glu Phe Lys Glu Leu Asp Tyr Gly Asn Val Thr
1               5                   10                  15

Phe Leu Lys Arg Gly Phe Arg Gln Asp Asp Lys Tyr Lys Phe Leu Ile
            20                  25                  30

His Pro Thr Phe Pro Val Glu Glu Ile Tyr Glu Ser Ile Arg Trp Thr
        35                  40                  45

Lys Lys Pro Ser Gln Met Gln Glu His Val Leu Ser Leu Cys His Leu
    50                  55                  60

Met Trp His Asn Gly Pro Glu Ile Tyr Lys Asp Phe Glu Thr Lys Ile
65                  70                  75                  80

Arg Ser Val Ser Ala Gly Arg Ala Leu Tyr Ile Pro Pro Tyr Glu Leu
                85                  90                  95

Leu Arg His Glu Trp Tyr Glu Lys Phe
            100                 105


<210> SEQ ID NO 10
<211> LENGTH: 105
<212> TYPE: PRT
<213> ORGANISM: Artificial Sequence
<220> FEATURE:
<223> OTHER INFORMATION: Description of Artificial Sequence: Synthetic
      Last 105 amino acids of HRV14 RNA polymerase.

<400> SEQUENCE: 10

Pro Asp Lys Ser Glu Thr Phe Thr Lys Met Thr Trp Glu Asn Leu Thr
1               5                   10                  15

Phe Leu Lys Arg Tyr Phe Lys Pro Asp Gln Gln Phe Pro Phe Leu Val
            20                  25                  30

His Pro Val Met Pro Met Lys Asp Ile His Glu Ser Ile Arg Trp Thr
        35                  40                  45

Lys Asp Pro Lys Asn Thr Gln Asp His Val Arg Ser Leu Cys Met Leu
    50                  55                  60

Ala Trp His Ser Gly Glu Lys Glu Tyr Asn Glu Phe Ile Gln Lys Ile
65                  70                  75                  80

Arg Thr Thr Asp Ile Gly Lys Cys Leu Ile Leu Pro Glu Tyr Ser Val
                85                  90                  95

Leu Arg Arg Arg Trp Leu Asp Leu Phe
            100                 105


<210> SEQ ID NO 11
<211> LENGTH: 240
<212> TYPE: PRT
<213> ORGANISM: Artificial Sequence
<220> FEATURE:
<223> OTHER INFORMATION: Description of Artificial Sequence: Synthetic
      HRV16 VP-pol fusion peptide. Synthetic peptide comprising HRV16
      VP135 and the last 105 amino acids of HRV16 RNA polymerase.

<400> SEQUENCE: 11

Met Gly Ala Gln Val Ser Arg Gln Asn Val Gly Thr His Ser Thr Gln
1               5                   10                  15

Asn Met Val Ser Asn Gly Ser Ser Leu Asn Tyr Phe Asn Ile Asn Tyr
            20                  25                  30

Phe Lys Asp Ala Ala Ser Ser Gly Ala Ser Arg Leu Asp Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln Ser Pro Ser Val Glu Ala Cys Gly Tyr Ser Asp
```

```
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Pro Gln Asp Ala Thr Ala Ile Asp Lys Pro Thr Gln Pro Asp Thr Ser
        115                 120                 125

Ser Asn Arg Phe Tyr Thr Leu Ala Asp Lys Ser Ser Glu Phe Lys Glu
    130                 135                 140

Leu Asp Tyr Gly Asn Val Thr Phe Leu Lys Arg Gly Phe Arg Gln Asp
145                 150                 155                 160

Asp Lys Tyr Lys Phe Leu Ile His Pro Thr Phe Pro Val Glu Glu Ile
                165                 170                 175

Tyr Glu Ser Ile Arg Trp Thr Lys Lys Pro Ser Gln Met Gln Glu His
            180                 185                 190

Val Leu Ser Leu Cys His Leu Met Trp His Asn Gly Pro Glu Ile Tyr
        195                 200                 205

Lys Asp Phe Glu Thr Lys Ile Arg Ser Val Ser Ala Gly Arg Ala Leu
    210                 215                 220

Tyr Ile Pro Pro Tyr Glu Leu Leu Arg His Glu Trp Tyr Glu Lys Phe
225                 230                 235                 240


<210> SEQ ID NO 12
<211> LENGTH: 240
<212> TYPE: PRT
<213> ORGANISM: Artificial Sequence
<220> FEATURE:
<223> OTHER INFORMATION: Description of Artificial Sequence: Synthetic
      HRV14 VP-Pol fusion peptide. Synthetic peptide comprising HRV14
      VP135 and the last 105 amino acids of HRV14 RNA polymerase.

<400> SEQUENCE: 12

Met Gly Ala Gln Val Ser Thr Gln Lys Ser Gly Ser His Glu Asn Gln
1               5                   10                  15

Asn Ile Leu Thr Asn Gly Ser Asn Gln Thr Phe Thr Val Ile Asn Tyr
            20                  25                  30

Tyr Lys Asp Ala Ala Ser Thr Ser Ser Ala Gly Gln Ser Leu Ser Met
        35                  40                  45

Asp Pro Ser Lys Phe Thr Glu Pro Val Lys Asp Leu Met Leu Lys Gly
    50                  55                  60

Ala Pro Ala Leu Asn Ser Pro Asn Val Glu Ala Cys Gly Tyr Ser Asp
65                  70                  75                  80

Arg Val Gln Gln Ile Thr Leu Gly Asn Ser Thr Ile Thr Thr Gln Glu
                85                  90                  95

Ala Ala Asn Ala Val Val Cys Tyr Ala Glu Trp Pro Glu Tyr Leu Pro
            100                 105                 110

Asp Val Asp Ala Ser Asp Val Asn Lys Thr Ser Lys Pro Asp Thr Ser
        115                 120                 125

Val Cys Arg Phe Tyr Thr Leu Pro Asp Lys Ser Glu Thr Phe Thr Lys
    130                 135                 140

Met Thr Trp Glu Asn Leu Thr Phe Leu Lys Arg Tyr Phe Lys Pro Asp
145                 150                 155                 160

Gln Gln Phe Pro Phe Leu Val His Pro Val Met Pro Met Lys Asp Ile
                165                 170                 175

His Glu Ser Ile Arg Trp Thr Lys Asp Pro Lys Asn Thr Gln Asp His
            180                 185                 190
```

```
Val Arg Ser Leu Cys Met Leu Ala Trp His Ser Gly Glu Lys Glu Tyr
        195                 200                 205

Asn Glu Phe Ile Gln Lys Ile Arg Thr Thr Asp Ile Gly Lys Cys Leu
    210                 215                 220

Ile Leu Pro Glu Tyr Ser Val Leu Arg Arg Arg Trp Leu Asp Leu Phe
225                 230                 235                 240


<210> SEQ ID NO 13
<211> LENGTH: 363
<212> TYPE: PRT
<213> ORGANISM: Artificial Sequence
<220> FEATURE:
<223> OTHER INFORMATION: Description of Artificial Sequence: Synthetic
      Amino acid sequence of the C-terminal domain of HRV16 RNA
      polymerase.

<400> SEQUENCE: 13

Glu Asp Ser Val Phe Gly Met Asp Gly Leu Glu Ala Leu Asp Leu Asn
1               5                   10                  15

Thr Ser Ala Gly Tyr Pro Tyr Val Thr Leu Gly Ile Lys Lys Lys Asp
            20                  25                  30

Leu Ile Asn Asn Lys Thr Lys Asp Ile Ser Lys Leu Lys Leu Ala Leu
        35                  40                  45

Asp Lys Tyr Asp Val Asp Leu Pro Met Ile Thr Phe Leu Lys Asp Glu
    50                  55                  60

Leu Arg Lys Lys Asp Lys Ile Ala Ala Gly Lys Thr Arg Val Ile Glu
65                  70                  75                  80

Ala Ser Ser Ile Asn Asp Thr Ile Leu Phe Arg Thr Val Tyr Gly Asn
                85                  90                  95

Leu Phe Ser Lys Phe His Leu Asn Pro Gly Val Val Thr Gly Cys Ala
            100                 105                 110

Val Gly Cys Asp Pro Glu Thr Phe Trp Ser Lys Ile Pro Leu Met Leu
        115                 120                 125

Asp Gly Asp Cys Ile Met Ala Phe Asp Tyr Thr Asn Tyr Asp Gly Ser
    130                 135                 140

Ile His Pro Ile Trp Phe Lys Ala Leu Gly Met Val Leu Asp Asn Leu
145                 150                 155                 160

Ser Phe Asn Pro Thr Leu Ile Asn Arg Leu Cys Asn Ser Lys His Ile
                165                 170                 175

Phe Lys Ser Thr Tyr Tyr Glu Val Glu Gly Gly Val Pro Ser Gly Cys
            180                 185                 190

Ser Gly Thr Ser Ile Phe Asn Ser Met Ile Asn Asn Ile Ile Ile Arg
        195                 200                 205

Thr Leu Val Leu Asp Ala Tyr Lys His Ile Asp Leu Asp Lys Leu Lys
    210                 215                 220

Ile Ile Ala Tyr Gly Asp Asp Val Ile Phe Ser Tyr Lys Tyr Lys Leu
225                 230                 235                 240

Asp Met Glu Ala Ile Ala Lys Glu Gly Gln Lys Tyr Gly Leu Thr Ile
                245                 250                 255

Thr Pro Ala Asp Lys Ser Ser Glu Phe Lys Glu Leu Asp Tyr Gly Asn
            260                 265                 270

Val Thr Phe Leu Lys Arg Gly Phe Arg Gln Asp Asp Lys Tyr Lys Phe
        275                 280                 285

Leu Ile His Pro Thr Phe Pro Val Glu Glu Ile Tyr Glu Ser Ile Arg
    290                 295                 300
```

-continued

Trp Thr Lys Lys Pro Ser Gln Met Gln Glu His Val Leu Ser Leu Cys
305 310 315 320

His Leu Met Trp His Asn Gly Pro Glu Ile Tyr Lys Asp Phe Glu Thr
325 330 335

Lys Ile Arg Ser Val Ser Ala Gly Arg Ala Leu Tyr Ile Pro Pro Tyr
340 345 350

Glu Leu Leu Arg His Glu Trp Tyr Glu Lys Phe
355 360

<210> SEQ ID NO 14
<211> LENGTH: 363
<212> TYPE: PRT
<213> ORGANISM: Artificial Sequence
<220> FEATURE:
<223> OTHER INFORMATION: Description of Artificial Sequence: Synthetic Amino acid sequence of the C-terminal domain of HRV14 RNA polymerase.
<220> FEATURE:
<221> NAME/KEY: SITE
<222> LOCATION: (186)..(363)
<223> OTHER INFORMATION: Pool F - 15mer synthetic peptide used for splenocyte stimulation.

<400> SEQUENCE: 14

Lys Glu Ala Leu Tyr Gly Val Asp Gly Leu Glu Pro Ile Asp Ile Thr
1 5 10 15

Thr Ser Ala Gly Phe Pro Tyr Val Ser Leu Gly Ile Lys Lys Arg Asp
20 25 30

Ile Leu Asn Lys Glu Thr Gln Asp Thr Glu Lys Met Lys Phe Tyr Leu
35 40 45

Asp Lys Tyr Gly Ile Asp Leu Pro Leu Val Thr Tyr Ile Lys Asp Glu
50 55 60

Leu Arg Ser Val Asp Lys Val Arg Leu Gly Lys Ser Arg Leu Ile Glu
65 70 75 80

Ala Ser Ser Leu Asn Asp Ser Val Asn Met Arg Met Lys Leu Gly Asn
85 90 95

Leu Tyr Lys Ala Phe His Gln Asn Pro Gly Val Leu Thr Gly Ser Ala
100 105 110

Val Gly Cys Asp Pro Asp Val Phe Trp Ser Val Ile Pro Cys Leu Met
115 120 125

Asp Gly His Leu Met Ala Phe Asp Tyr Ser Asn Phe Asp Ala Ser Leu
130 135 140

Ser Pro Val Trp Phe Val Cys Leu Glu Lys Val Leu Thr Lys Leu Gly
145 150 155 160

Phe Ala Gly Ser Ser Leu Ile Gln Ser Ile Cys Asn Thr His His Ile
165 170 175

Phe Arg Asp Glu Ile Tyr Val Val Glu Gly Gly Met Pro Ser Gly Cys
180 185 190

Ser Gly Thr Ser Ile Phe Asn Ser Met Ile Asn Asn Ile Ile Ile Arg
195 200 205

Thr Leu Ile Leu Asp Ala Tyr Lys Gly Ile Asp Leu Asp Lys Leu Lys
210 215 220

Ile Leu Ala Tyr Gly Asp Asp Leu Ile Val Ser Tyr Pro Tyr Glu Leu
225 230 235 240

Asp Pro Gln Val Leu Ala Thr Leu Gly Lys Asn Tyr Gly Leu Thr Ile
245 250 255

Thr Pro Pro Asp Lys Ser Glu Thr Phe Thr Lys Met Thr Trp Glu Asn
260 265 270

```
Leu Thr Phe Leu Lys Arg Tyr Phe Lys Pro Asp Gln Gln Phe Pro Phe
        275                 280                 285

Leu Val His Pro Val Met Pro Met Lys Asp Ile His Glu Ser Ile Arg
    290                 295                 300

Trp Thr Lys Asp Pro Lys Asn Thr Gln Asp His Val Arg Ser Leu Cys
305                 310                 315                 320

Met Leu Ala Trp His Ser Gly Glu Lys Glu Tyr Asn Glu Phe Ile Gln
                325                 330                 335

Lys Ile Arg Thr Thr Asp Ile Gly Lys Cys Leu Ile Leu Pro Glu Tyr
            340                 345                 350

Ser Val Leu Arg Arg Arg Trp Leu Asp Leu Phe
        355                 360


<210> SEQ ID NO 15
<211> LENGTH: 460
<212> TYPE: PRT
<213> ORGANISM: Artificial Sequence
<220> FEATURE:
<223> OTHER INFORMATION: Description of Artificial Sequence: Synthetic
      Amino acid sequence of HRV16 RNA polymerase.

<400> SEQUENCE: 15

Gly Gln Ile Gln Ile Ser Lys His Val Lys Asp Val Gly Leu Pro Ser
1               5                   10                  15

Ile His Thr Pro Thr Lys Thr Lys Leu Gln Pro Ser Val Phe Tyr Asp
            20                  25                  30

Ile Phe Pro Gly Ser Lys Glu Pro Ala Val Leu Thr Glu Lys Asp Pro
        35                  40                  45

Arg Leu Lys Val Asp Phe Asp Ser Ala Leu Phe Ser Lys Tyr Lys Gly
    50                  55                  60

Asn Thr Glu Cys Ser Leu Asn Glu His Ile Gln Val Ala Val Ala His
65                  70                  75                  80

Tyr Ser Ala Gln Leu Ala Thr Leu Asp Ile Asp Pro Gln Pro Ile Ala
                85                  90                  95

Met Glu Asp Ser Val Phe Gly Met Asp Gly Leu Glu Ala Leu Asp Leu
            100                 105                 110

Asn Thr Ser Ala Gly Tyr Pro Tyr Val Thr Leu Gly Ile Lys Lys Lys
        115                 120                 125

Asp Leu Ile Asn Asn Lys Thr Lys Asp Ile Ser Lys Leu Lys Leu Ala
    130                 135                 140

Leu Asp Lys Tyr Asp Val Asp Leu Pro Met Ile Thr Phe Leu Lys Asp
145                 150                 155                 160

Glu Leu Arg Lys Lys Asp Lys Ile Ala Ala Gly Lys Thr Arg Val Ile
                165                 170                 175

Glu Ala Ser Ser Ile Asn Asp Thr Ile Leu Phe Arg Thr Val Tyr Gly
            180                 185                 190

Asn Leu Phe Ser Lys Phe His Leu Asn Pro Gly Val Val Thr Gly Cys
        195                 200                 205

Ala Val Gly Cys Asp Pro Glu Thr Phe Trp Ser Lys Ile Pro Leu Met
    210                 215                 220

Leu Asp Gly Asp Cys Ile Met Ala Phe Asp Tyr Thr Asn Tyr Asp Gly
225                 230                 235                 240

Ser Ile His Pro Ile Trp Phe Lys Ala Leu Gly Met Val Leu Asp Asn
                245                 250                 255

Leu Ser Phe Asn Pro Thr Leu Ile Asn Arg Leu Cys Asn Ser Lys His
```

```
            260                 265                 270

Ile Phe Lys Ser Thr Tyr Tyr Glu Val Glu Gly Gly Val Pro Ser Gly
        275                 280                 285

Cys Ser Gly Thr Ser Ile Phe Asn Ser Met Ile Asn Asn Ile Ile Ile
    290                 295                 300

Arg Thr Leu Val Leu Asp Ala Tyr Lys His Ile Asp Leu Asp Lys Leu
305                 310                 315                 320

Lys Ile Ile Ala Tyr Gly Asp Asp Val Ile Phe Ser Tyr Lys Tyr Lys
                325                 330                 335

Leu Asp Met Glu Ala Ile Ala Lys Glu Gly Gln Lys Tyr Gly Leu Thr
            340                 345                 350

Ile Thr Pro Ala Asp Lys Ser Ser Glu Phe Lys Glu Leu Asp Tyr Gly
        355                 360                 365

Asn Val Thr Phe Leu Lys Arg Gly Phe Arg Gln Asp Asp Lys Tyr Lys
    370                 375                 380

Phe Leu Ile His Pro Thr Phe Pro Val Glu Glu Ile Tyr Glu Ser Ile
385                 390                 395                 400

Arg Trp Thr Lys Lys Pro Ser Gln Met Gln Glu His Val Leu Ser Leu
                405                 410                 415

Cys His Leu Met Trp His Asn Gly Pro Glu Ile Tyr Lys Asp Phe Glu
            420                 425                 430

Thr Lys Ile Arg Ser Val Ser Ala Gly Arg Ala Leu Tyr Ile Pro Pro
        435                 440                 445

Tyr Glu Leu Leu Arg His Glu Trp Tyr Glu Lys Phe
    450                 455                 460


<210> SEQ ID NO 16
<211> LENGTH: 460
<212> TYPE: PRT
<213> ORGANISM: Artificial Sequence
<220> FEATURE:
<223> OTHER INFORMATION: Description of Artificial Sequence: Synthetic
      Amino acid sequence of HRV14 RNA polymerase.

<400> SEQUENCE: 16

Gly Gln Val Ile Ala Arg His Lys Val Arg Glu Phe Asn Ile Asn Pro
1               5                   10                  15

Val Asn Thr Pro Thr Lys Ser Lys Leu His Pro Ser Val Phe Tyr Asp
            20                  25                  30

Val Phe Pro Gly Asp Lys Glu Pro Ala Val Leu Ser Asp Asn Asp Pro
        35                  40                  45

Arg Leu Glu Val Lys Leu Thr Glu Ser Leu Phe Ser Lys Tyr Lys Gly
    50                  55                  60

Asn Val Asn Thr Glu Pro Thr Glu Asn Met Leu Val Ala Val Asp His
65                  70                  75                  80

Tyr Ala Gly Gln Leu Leu Ser Leu Asp Ile Pro Thr Ser Glu Leu Thr
                85                  90                  95

Leu Lys Glu Ala Leu Tyr Gly Val Asp Gly Leu Glu Pro Ile Asp Ile
            100                 105                 110

Thr Thr Ser Ala Gly Phe Pro Tyr Val Ser Leu Gly Ile Lys Lys Arg
        115                 120                 125

Asp Ile Leu Asn Lys Glu Thr Gln Asp Thr Glu Lys Met Lys Phe Tyr
    130                 135                 140

Leu Asp Lys Tyr Gly Ile Asp Leu Pro Leu Val Thr Tyr Ile Lys Asp
145                 150                 155                 160
```

-continued

```
Glu Leu Arg Ser Val Asp Lys Val Arg Leu Gly Lys Ser Arg Leu Ile
                165                 170                 175

Glu Ala Ser Ser Leu Asn Asp Ser Val Asn Met Arg Met Lys Leu Gly
            180                 185                 190

Asn Leu Tyr Lys Ala Phe His Gln Asn Pro Gly Val Leu Thr Gly Ser
        195                 200                 205

Ala Val Gly Cys Asp Pro Asp Val Phe Trp Ser Val Ile Pro Cys Leu
    210                 215                 220

Met Asp Gly His Leu Met Ala Phe Asp Tyr Ser Asn Phe Asp Ala Ser
225                 230                 235                 240

Leu Ser Pro Val Trp Phe Val Cys Leu Glu Lys Val Leu Thr Lys Leu
                245                 250                 255

Gly Phe Ala Gly Ser Ser Leu Ile Gln Ser Ile Cys Asn Thr His His
            260                 265                 270

Ile Phe Arg Asp Glu Ile Tyr Val Val Glu Gly Gly Met Pro Ser Gly
        275                 280                 285

Cys Ser Gly Thr Ser Ile Phe Asn Ser Met Ile Asn Asn Ile Ile Ile
    290                 295                 300

Arg Thr Leu Ile Leu Asp Ala Tyr Lys Gly Ile Asp Leu Asp Lys Leu
305                 310                 315                 320

Lys Ile Leu Ala Tyr Gly Asp Asp Leu Ile Val Ser Tyr Pro Tyr Glu
                325                 330                 335

Leu Asp Pro Gln Val Leu Ala Thr Leu Gly Lys Asn Tyr Gly Leu Thr
            340                 345                 350

Ile Thr Pro Pro Asp Lys Ser Glu Thr Phe Thr Lys Met Thr Trp Glu
        355                 360                 365

Asn Leu Thr Phe Leu Lys Arg Tyr Phe Lys Pro Asp Gln Gln Phe Pro
    370                 375                 380

Phe Leu Val His Pro Val Met Pro Met Lys Asp Ile His Glu Ser Ile
385                 390                 395                 400

Arg Trp Thr Lys Asp Pro Lys Asn Thr Gln Asp His Val Arg Ser Leu
                405                 410                 415

Cys Met Leu Ala Trp His Ser Gly Glu Lys Glu Tyr Asn Glu Phe Ile
            420                 425                 430

Gln Lys Ile Arg Thr Thr Asp Ile Gly Lys Cys Leu Ile Leu Pro Glu
        435                 440                 445

Tyr Ser Val Leu Arg Arg Arg Trp Leu Asp Leu Phe
    450                 455                 460
```

<210> SEQ ID NO 17
<211> LENGTH: 332
<212> TYPE: PRT
<213> ORGANISM: Artificial Sequence
<220> FEATURE:
<223> OTHER INFORMATION: Description of Artificial Sequence: Synthetic HRV1B VP0 polyprotein. This comprises nucleocapsid proteins VP2 and VP4.
<220> FEATURE:
<221> NAME/KEY: SITE
<222> LOCATION: (1)..(171)
<223> OTHER INFORMATION: Pool C - 15mer synthetic peptide used for splenocyte stimulation.
<220> FEATURE:
<221> NAME/KEY: SITE
<222> LOCATION: (172)..(332)
<223> OTHER INFORMATION: Pool D - 15mer synthetic peptide used for splenocyte stimulation.

<400> SEQUENCE: 17

-continued

```
Met Gly Ala Gln Val Ser Arg Gln Asn Val Gly Thr His Ser Thr Gln
1               5                   10                  15

Asn Ser Val Ser Asn Gly Ser Ser Leu Asn Tyr Phe Asn Ile Asn Tyr
            20                  25                  30

Phe Lys Asp Ala Ala Ser Ser Gly Ala Ser Arg Leu Asp Phe Ser Gln
        35                  40                  45

Asp Pro Ser Lys Phe Thr Asp Pro Val Lys Asp Val Leu Glu Lys Gly
    50                  55                  60

Ile Pro Thr Leu Gln Ser Pro Ser Val Glu Ala Cys Gly Tyr Ser Asp
65                  70                  75                  80

Arg Ile Ile Gln Ile Thr Arg Gly Asp Ser Thr Ile Thr Ser Gln Asp
                85                  90                  95

Val Ala Asn Ala Val Val Gly Tyr Gly Val Trp Pro His Tyr Leu Thr
            100                 105                 110

Pro Gln Asp Ala Thr Ala Ile Asp Lys Pro Thr Gln Pro Asp Thr Ser
        115                 120                 125

Ser Asn Arg Phe Tyr Thr Leu Glu Ser Lys His Trp Asn Gly Asp Ser
    130                 135                 140

Lys Gly Trp Trp Trp Lys Leu Pro Asp Ala Leu Lys Glu Met Gly Ile
145                 150                 155                 160

Phe Gly Glu Asn Met Tyr Tyr His Phe Leu Gly Arg Ser Gly Tyr Thr
                165                 170                 175

Val His Val Gln Cys Asn Ala Ser Lys Phe His Gln Gly Thr Leu Leu
            180                 185                 190

Val Ala Met Ile Pro Glu His Gln Leu Ala Ser Ala Lys Asn Gly Ser
        195                 200                 205

Val Thr Ala Gly Tyr Asn Leu Thr His Pro Gly Glu Ala Gly Arg Val
    210                 215                 220

Val Gly Gln Gln Arg Asp Ala Asn Leu Arg Gln Pro Ser Asp Asp Ser
225                 230                 235                 240

Trp Leu Asn Phe Asp Gly Thr Leu Leu Gly Asn Leu Leu Ile Phe Pro
                245                 250                 255

His Gln Phe Ile Asn Leu Arg Ser Asn Asn Ser Ala Thr Leu Ile Val
            260                 265                 270

Pro Tyr Val Asn Ala Val Pro Met Asp Ser Met Leu Arg His Asn Asn
        275                 280                 285

Trp Ser Leu Val Ile Ile Pro Ile Ser Pro Leu Arg Ser Glu Thr Thr
    290                 295                 300

Ser Ser Asn Ile Arg Pro Ile Thr Val Ser Ile Ser Pro Met Cys Ala
305                 310                 315                 320

Glu Phe Ser Gly Ala Arg Ala Lys Asn Val Arg Gln
                325                 330


<210> SEQ ID NO 18
<211> LENGTH: 365
<212> TYPE: PRT
<213> ORGANISM: Artificial Sequence
<220> FEATURE:
<223> OTHER INFORMATION: Description of Artificial Sequence: Synthetic
      HRV1B RNA polymerase amino acid sequence. This comprises
      nucleocapsid proteins VP2 and VP4.
<220> FEATURE:
<221> NAME/KEY: SITE
<222> LOCATION: (1)..(187)
<223> OTHER INFORMATION: Pool A - 15mer synthetic peptide used for
      splenocyte stimulation.
<220> FEATURE:
<221> NAME/KEY: SITE
```

-continued

<222> LOCATION: (188)..(365)
<223> OTHER INFORMATION: Pool B - 15mer synthetic peptide used for splenocyte stimulation.

<400> SEQUENCE: 18

```
Met Leu Glu Asp Ser Val Phe Gly Ile Glu Gly Leu Glu Ala Leu Asp
1               5                   10                  15

Leu Asn Thr Ser Ala Gly Phe Pro Tyr Val Thr Met Gly Ile Lys Lys
            20                  25                  30

Arg Asp Leu Ile Asn Asn Lys Thr Lys Asp Ile Ser Arg Leu Lys Glu
        35                  40                  45

Ala Leu Asp Lys Tyr Gly Val Asp Leu Pro Met Ile Thr Phe Leu Lys
    50                  55                  60

Asp Glu Leu Arg Lys Lys Glu Lys Ile Ser Ala Gly Lys Thr Arg Val
65                  70                  75                  80

Ile Glu Ala Ser Ser Ile Asn Asp Thr Ile Leu Phe Arg Thr Thr Phe
                85                  90                  95

Gly Asn Leu Phe Ser Lys Phe His Leu Asn Pro Gly Val Val Thr Gly
            100                 105                 110

Ser Ala Val Gly Cys Asp Pro Glu Thr Phe Trp Ser Lys Ile Pro Val
        115                 120                 125

Met Leu Asp Gly Asp Cys Ile Met Ala Phe Asp Tyr Thr Asn Tyr Asp
    130                 135                 140

Gly Ser Ile His Pro Val Trp Phe Gln Ala Leu Lys Lys Val Leu Glu
145                 150                 155                 160

Asn Leu Ser Phe Gln Ser Asn Leu Ile Asp Arg Leu Cys Tyr Ser Lys
                165                 170                 175

His Leu Phe Lys Ser Thr Tyr Tyr Glu Val Ala Gly Gly Val Pro Ser
            180                 185                 190

Gly Cys Ser Gly Thr Ser Ile Phe Asn Thr Met Ile Asn Asn Ile Ile
        195                 200                 205

Ile Arg Thr Leu Val Leu Asp Ala Tyr Lys Asn Ile Asp Leu Asp Lys
    210                 215                 220

Leu Lys Ile Ile Ala Tyr Gly Asp Asp Val Ile Phe Ser Tyr Lys Tyr
225                 230                 235                 240

Thr Leu Asp Met Glu Ala Ile Ala Asn Glu Gly Lys Lys Tyr Gly Leu
                245                 250                 255

Thr Ile Thr Pro Ala Asp Lys Ser Thr Glu Phe Lys Lys Leu Asp Tyr
            260                 265                 270

Asn Asn Val Thr Phe Leu Lys Arg Gly Phe Lys Gln Asp Glu Lys His
        275                 280                 285

Thr Phe Leu Ile His Pro Thr Phe Pro Val Glu Glu Ile Tyr Glu Ser
    290                 295                 300

Ile Arg Trp Thr Lys Lys Pro Ser Gln Met Gln Glu His Val Leu Ser
305                 310                 315                 320

Leu Cys His Leu Met Trp His Asn Gly Arg Lys Val Tyr Glu Asp Phe
                325                 330                 335

Ser Ser Lys Ile Arg Ser Val Ser Ala Gly Arg Ala Leu Tyr Ile Pro
            340                 345                 350

Pro Tyr Asp Leu Leu Lys His Glu Trp Tyr Glu Lys Phe
        355                 360                 365
```

<210> SEQ ID NO 19
<211> LENGTH: 239
<212> TYPE: PRT

<213> ORGANISM: Artificial Sequence
<220> FEATURE:
<223> OTHER INFORMATION: Description of Artificial Sequence: Synthetic
HRV1 VP-Pol fusion protein. This (N-terminal) amino acids 2 to 135
of the VPo polyprotein of HRV1B and the last 105 amino acids
of HRV1B RNA polymerase.

<400> SEQUENCE: 19

```
Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Arg Leu Asp Phe Ser Gln Asp
        35                  40                  45

Pro Ser Lys Phe Thr Asp Pro Val Lys Asp Val Leu Glu Lys Gly Ile
    50                  55                  60

Pro Thr Leu Gln Ser Pro Ser Val Glu Ala Cys Gly Tyr Ser Asp Arg
65                  70                  75                  80

Ile Ile Gln Ile Thr Arg Gly Asp Ser Thr Ile Thr Ser Gln Asp Val
                85                  90                  95

Ala Asn Ala Val Val Gly Tyr Gly Val Trp Pro His Tyr Leu Thr Pro
            100                 105                 110

Gln Asp Ala Thr Ala Ile Asp Lys Pro Thr Gln Pro Asp Thr Ser Ser
        115                 120                 125

Asn Arg Phe Tyr Thr Leu Ala Asp Lys Ser Thr Glu Phe Lys Lys Leu
    130                 135                 140

Asp Tyr Asn Asn Val Thr Phe Leu Lys Arg Gly Phe Lys Gln Asp Glu
145                 150                 155                 160

Lys His Thr Phe Leu Ile His Pro Thr Phe Pro Val Glu Glu Ile Tyr
                165                 170                 175

Glu Ser Ile Arg Trp Thr Lys Lys Pro Ser Gln Met Gln Glu His Val
            180                 185                 190

Leu Ser Leu Cys His Leu Met Trp His Asn Gly Arg Lys Val Tyr Glu
        195                 200                 205

Asp Phe Ser Ser Lys Ile Arg Ser Val Ser Ala Gly Arg Ala Leu Tyr
    210                 215                 220

Ile Pro Pro Tyr Asp Leu Leu Lys His Glu Trp Tyr Glu Lys Phe
225                 230                 235
```

<210> SEQ ID NO 20
<211> LENGTH: 331
<212> TYPE: PRT
<213> ORGANISM: Artificial Sequence
<220> FEATURE:
<223> OTHER INFORMATION: Description of Artificial Sequence: Synthetic
HRV29 VP0 polyprotein. This comprises nucleocapsid proteins VP2
and VP4.

<400> SEQUENCE: 20

```
Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser Lys Phe Thr Asp Pro Val Lys Asp Val Leu Glu Lys Gly Ile
    50                  55                  60

Pro Thr Leu Gln Ser Pro Thr Val Glu Ala Cys Gly Tyr Ser Asp Arg
```

```
65                  70                  75                  80

Ile Met Gln Ile Thr Arg Gly Asp Ser Thr Ile Thr Ser Gln Asp Val
                85                  90                  95

Ala Asn Ala Val Ile Gly Tyr Gly Val Trp Pro His Tyr Leu Ser Ala
            100                 105                 110

Glu Asp Ala Thr Ala Ile Asp Lys Pro Thr Gln Pro Asp Thr Ser Ser
        115                 120                 125

Asn Arg Phe Tyr Thr Leu Glu Ser Lys Thr Trp Asp Arg Gln Ser Lys
    130                 135                 140

Gly Trp Trp Trp Lys Leu Pro Asp Ala Leu Lys Asp Met Gly Ile Phe
145                 150                 155                 160

Gly Glu Asn Met Tyr Tyr His Tyr Leu Gly Arg Ser Gly Tyr Thr Val
                165                 170                 175

His Val Gln Cys Asn Ala Ser Lys Phe His Gln Gly Thr Leu Leu Val
            180                 185                 190

Val Met Ile Leu Glu His Gln Leu Ala Ser Val Gly Thr Glu Lys Val
        195                 200                 205

Gly Pro Gly Tyr Asn Phe Thr His Pro Gly Glu Ala Gly Arg Gln Ile
    210                 215                 220

Gly Asn Val Ser Asp Arg Thr Ser Lys His Pro Ser Asp Asp Asn Trp
225                 230                 235                 240

Leu Asn Phe Asp Gly Thr Leu Leu Gly Asn Val Leu Ile Phe Pro His
                245                 250                 255

Gln Phe Ile Asn Leu Arg Ser Asn Asn Ser Ala Thr Ile Ile Val Pro
            260                 265                 270

Tyr Val Asn Ala Val Pro Met Asp Ser Met Leu Arg His Asn Asn Trp
        275                 280                 285

Ser Leu Val Ile Ile Pro Ile Ser Glu Leu Gln Thr Glu Asn Ala Thr
    290                 295                 300

Asn Leu Thr Val Pro Ile Thr Val Ser Ile Ser Pro Met Phe Ala Glu
305                 310                 315                 320

Phe Ser Gly Ala Arg Ala Arg Pro Ala Arg Ala
                325                 330


<210> SEQ ID NO 21
<211> LENGTH: 362
<212> TYPE: PRT
<213> ORGANISM: Artificial Sequence
<220> FEATURE:
<223> OTHER INFORMATION: Description of Artificial Sequence: Synthetic
      Amino acid sequence of HRV29 RNA polymerase.

<400> SEQUENCE: 21

Glu Ser Val Phe Gly Ile Glu Gly Leu Glu Ala Leu Asp Leu Asn Thr
1               5                   10                  15

Ser Ala Gly Phe Pro Tyr Ile Ser Met Gly Ile Lys Lys Arg Asp Leu
            20                  25                  30

Ile Asn Lys Gln Thr Lys Asp Val Thr Lys Leu Lys Met Ala Leu Asp
        35                  40                  45

Lys Tyr Gly Val Asp Leu Pro Met Val Thr Phe Leu Lys Asp Glu Leu
    50                  55                  60

Arg Lys Arg Glu Lys Ile Cys Ala Gly Lys Thr Arg Val Ile Glu Ala
65                  70                  75                  80

Ser Ser Val Asn Asp Thr Ile Leu Phe Arg Thr Thr Phe Gly Asn Leu
                85                  90                  95
```

-continued

```
Phe Ser Lys Phe His Leu Asn Pro Gly Val Val Thr Gly Ser Ala Val
            100                 105                 110

Gly Cys Asp Pro Glu Thr Phe Trp Ser Lys Ile Pro Val Met Leu Asp
        115                 120                 125

Gly Glu Cys Ile Met Ala Phe Asp Tyr Thr Asn Tyr Asp Gly Ser Ile
    130                 135                 140

His Pro Ile Trp Phe Gln Ala Leu Lys Glu Val Leu Ala Asn Leu Ser
145                 150                 155                 160

Phe Glu Pro Ala Leu Ile Asp Arg Leu Cys Arg Ser Lys His Ile Phe
                165                 170                 175

Lys Asn Thr Tyr Tyr Glu Val Glu Gly Gly Ile Pro Ser Gly Cys Ser
            180                 185                 190

Gly Thr Ser Ile Phe Asn Thr Met Ile Asn Asn Val Ile Ile Arg Thr
        195                 200                 205

Leu Val Leu Asp Ala Tyr Lys Asn Ile Asp Leu Asp Lys Leu Lys Ile
    210                 215                 220

Leu Ala Tyr Gly Asp Asp Val Ile Phe Ser Tyr Lys Tyr Gln Leu Asp
225                 230                 235                 240

Met Glu Ala Ile Ala Lys Glu Gly Thr Lys Tyr Gly Leu Thr Ile Thr
                245                 250                 255

Pro Ala Asp Lys Ser Asp Cys Phe Lys Gln Leu Asn Tyr Asn Asn Val
            260                 265                 270

Thr Phe Leu Lys Arg Gly Phe Arg Gln Asp Glu Lys His Asn Phe Leu
        275                 280                 285

Ile His Pro Thr Phe Pro Val Glu Glu Ile Gln Glu Ser Ile Arg Trp
    290                 295                 300

Thr Lys Lys Pro Ser Gln Met Gln Glu His Val Leu Ser Leu Cys His
305                 310                 315                 320

Leu Met Trp His Asn Gly Arg Asp Val Tyr Lys Gln Phe Glu Asp Arg
                325                 330                 335

Ile Arg Ser Val Ser Ala Gly Arg Ala Leu Tyr Ile Pro Pro Tyr Asp
            340                 345                 350

Leu Leu Leu His Glu Trp Tyr Glu Lys Phe
        355                 360


<210> SEQ ID NO 22
<211> LENGTH: 239
<212> TYPE: PRT
<213> ORGANISM: Artificial Sequence
<220> FEATURE:
<223> OTHER INFORMATION: Description of Artificial Sequence: Synthetic
      HRV29 VP-Pol fusion peptide. This peptide comprises the first 134
      N-terminal amino acids of the VPo polyprotein of HRV29
      and the last 105 amino acids of HRV29 RNA polymerase.

<400> SEQUENCE: 22

Gly Ala Gln Val Ser Arg Gln Asn Val Gly Thr His Ser Thr Gln Asn
1               5                   10                  15

Ser Val Ser Asn Gly Ser Ser Leu Asn Tyr Phe Asn Ile Asn Tyr Phe
            20                  25                  30

Lys Asp Ala Ala Ser Ser Gly Ala Ser Lys Leu Glu Phe Ser Gln Asp
        35                  40                  45

Pro Ser Lys Phe Thr Asp Pro Val Lys Asp Val Leu Glu Lys Gly Ile
    50                  55                  60

Pro Thr Leu Gln Ser Pro Thr Val Glu Ala Cys Gly Tyr Ser Asp Arg
65                  70                  75                  80
```

-continued

```
Ile Met Gln Ile Thr Arg Gly Asp Ser Thr Ile Thr Ser Gln Asp Val
                85                  90                  95

Ala Asn Ala Val Ile Gly Tyr Gly Val Trp Pro His Tyr Leu Ser Ala
            100                 105                 110

Glu Asp Ala Thr Ala Ile Asp Lys Pro Thr Gln Pro Asp Thr Ser Ser
        115                 120                 125

Asn Arg Phe Tyr Thr Leu Ala Asp Lys Ser Asp Cys Phe Lys Gln Leu
    130                 135                 140

Asn Tyr Asn Asn Val Thr Phe Leu Lys Arg Gly Phe Arg Gln Asp Glu
145                 150                 155                 160

Lys His Asn Phe Leu Ile His Pro Thr Phe Pro Val Glu Glu Ile Gln
                165                 170                 175

Glu Ser Ile Arg Trp Thr Lys Lys Pro Ser Gln Met Gln Glu His Val
            180                 185                 190

Leu Ser Leu Cys His Leu Met Trp His Asn Gly Arg Asp Val Tyr Lys
        195                 200                 205

Gln Phe Glu Asp Arg Ile Arg Ser Val Ser Ala Gly Arg Ala Leu Tyr
    210                 215                 220

Ile Pro Pro Tyr Asp Leu Leu Leu His Glu Trp Tyr Glu Lys Phe
225                 230                 235


<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      DNA sequence of IL-4 forward primer.

<400> SEQUENCE: 23

acaggagaag ggacgccat                                                  19


<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA sequence of IL-4 reverse primer.

<400> SEQUENCE: 24

gaagccctac agacgagctc a                                               21


<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      Nucleotide sequence of IL-4 probe.

<400> SEQUENCE: 25

tcctcacagc aacgaaga                                                   18


<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA sequence of IFN-g forward primer.

<400> SEQUENCE: 26
```

tcaagtggca tagatgtgga agaa 24

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
DNA sequence of IFN-g reverse primer.

<400> SEQUENCE: 27
tggctctgca ggattttcat g 21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
DNA sequence of IFN-g probe.

<400> SEQUENCE: 28
tcaccatcct tttgccagtt 20

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
DNA sequence of IL-17a forward primer.

<400> SEQUENCE: 29
tcagactacc tcaaccgttc ca 22

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
DNA sequence of IL-17a reverse primer.

<400> SEQUENCE: 30
agcttcccag atcacagagg g 21

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
DNA sequence of IL-17a probe.

<400> SEQUENCE: 31
tcaccctgga ctctccaccg ca 22

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
DNA sequence of HRV forward primer.

<400> SEQUENCE: 32
gtgaagagcc scrtgtgct 19

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic DNA sequence of HRV reverse primer.

<400> SEQUENCE: 33
gctscagggt taaggttagc c 21

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic DNA sequence of HRV probe.

<400> SEQUENCE: 34
tgagtcctcc ggcccctgaa tg 22

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic DNA sequence of 18S forward primer.

<400> SEQUENCE: 35
cgccgctaga ggtgaaattc t 21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic DNA sequence of 18S reverse primer.

<400> SEQUENCE: 36
cattcttggc aaatgctttc g 21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic DNA sequence of 18S probe.

<400> SEQUENCE: 37
accggcgcaa gacggaccag a 21

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic CpG ODN 1826 oligonucleotide (DNA) sequence. Used as a Th1 immune response adjuvant.

<400> SEQUENCE: 38

```
tccatgacgt tcctgacgtt                                               20

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      CpG ODN 2216 oligonucleotide (DNA) sequence. Used as a Th1 immune
      response adjuvant.

<400> SEQUENCE: 39

gggggacgat cgtcggggg                                                19

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      CpG 2336 oligonucleotide (DNA) sequence. Used as a Th1 immune
      response adjuvant.

<400> SEQUENCE: 40

ggggacgacg tcgtgggggg g                                             21

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      CpG 7909 oligonucleotide (DNA) sequence. Used as a Th1 immune
      response adjuvant.

<400> SEQUENCE: 41

tcgtcgtttt gtcgttttgt cgtt                                          24
```

The invention claimed is:

1. An immunogenic composition comprising:
   a) an isolated peptide consisting of an amino acid sequence which is at least 90% identical to SEQ ID NO: 1 or SEQ ID NO: 2 or is at least 80% identical to an amino acid sequence located in SEQ ID NO: 5, 6, 8, 17, or 20, or an isolated polynucleotide comprising a nucleic acid sequence encoding said peptide, placed under the control of the elements necessary for its expression in a mammalian cell; and/or
   b) an isolated peptide comprising an amino acid sequence of at least 100 amino acids which is at least 90% identical to SEQ ID NO: 13 or SEQ ID NO: 14, or an isolated polynucleotide comprising a nucleic acid sequence encoding said peptide, placed under the control of the elements necessary for its expression in a mammalian cell;
   c) a pharmaceutically acceptable Th1 adjuvant when said immunogenic composition comprises one or more of said isolated peptides; and
   a pharmaceutically acceptable vehicle comprising one or more buffering agents.

2. The immunogenic composition according to claim 1, wherein the isolated peptide a) is a fusion peptide consisting of the amino acid sequence that is at least 90% identical to SEQ ID NO: 1 or SEQ ID NO: 2 further linked by a covalent linkage to an amino acid sequence which is at least 90% identical to an amino acid sequence located in SEQ ID NO: 3 or SEQ ID NO: 4.

3. The immunogenic composition according to claim 1, wherein the isolated peptide is a fusion peptide consisting of the amino acid sequence that is at least 90% identical to SEQ ID NO: 1 or SEQ ID NO: 2 or is at least 80% identical to an amino acid sequence located in SEQ ID NO: 5, 6, 8, 17, or 20, as defined in claim 1 or claim 2, further linked by covalent linkage to an amino acid sequence which is at least 90% identical to SEQ ID NO: 13 or SEQ ID NO: 14.

4. The immunogenic composition according to claim 3, wherein the amino acid sequence is within the last 105 C-terminal amino acids of SEQ ID NO: 13 or SEQ ID NO: 14.

5. The immunogenic composition according to claim 1, wherein the pharmaceutically acceptable Th1 adjuvant comprises a TLR9 agonist.

6. A method for inducing a specific cross-reactive cell-mediated immune response against at least two serotypes of rhinoviruses in a mammal, the method comprising administering the immunogenic composition according to claim 1 to a mammal in need of such treatment.

7. The method according to claim 6, wherein the at least two serotypes of rhinoviruses belong to type A and/or B rhinoviruses, or wherein said cell-mediated immune response is Th1-oriented, or wherein said cell-mediated immune response is boosted after infection by a rhinovirus, or wherein a specific neutralizing antibody response is further induced when said mammal is infected by a rhinovirus.

8. A method for:

(a) inducing a specific neutralizing antibody response in a mammal infected by a rhinovirus; or (b) shortening or preventing an infection in a mammal by a rhinovirus and/or reducing or preventing the clinical symptoms associated with an infection by a rhinovirus;

the method comprising administering the immunogenic composition according to claim 1 to a mammal in need of such treatment.

9. An immunogenic composition according to claim 1 for use as a vaccine.

10. The composition of claim 1, further comprising one or more tonicity adjusting agents.

11. The composition of claim 1, further comprising one or more wetting agents.

12. The composition of claim 1, further comprising one or more detergents.

13. The composition of claim 1, further comprising one or more pH adjusting agents.

14. A vaccine composition comprising:

a) an isolated peptide consisting of an immunogenic amino acid sequence which is at least 90% identical to SEQ ID NO: 1 or SEQ ID NO: 2 or is at least 80% identical to an amino acid sequence located in SEQ ID NO: 5, 6, 8, 17, or 20; and/or b) an isolated peptide consisting of an immunogenic amino acid sequence of at least 100 amino acids which is at least 90% identical to SEQ ID NO: 13 or SEQ ID NO: 14; and c) a pharmaceutically acceptable Th1 adjuvant; and d) a pharmaceutically acceptable vehicle comprising one or more buffering agents.

15. A composition comprising:

a) an isolated polynucleotide consisting of a deoxyribonucleic acid sequence encoding an isolated peptide comprising an immunogenic amino acid sequence which is at least 90% identical to SEQ ID NO: 1 or SEQ ID NO: 2 or is at least 80% identical to an amino acid sequence located in SEQ ID NO: 5, 6, 8, 17, or 20, placed under the control of elements necessary for its expression in a mammalian cell; and/or b) an isolated polynucleotide comprising a deoxyribonucleic acid sequence encoding an isolated peptide comprising an immunogenic amino acid sequence of at least 100 amino acids which is at least 90% identical to SEQ ID NO: 13 or SEQ ID NO: 14, placed under the control of elements necessary for its expression in a mammalian cell; and c) a pharmaceutically acceptable vehicle comprising one or more buffering agents.

* * * * *